(12) United States Patent
Helm

(10) Patent No.: US 10,682,507 B2
(45) Date of Patent: Jun. 16, 2020

(54) CATHETER EXTENSION WITH INTEGRATED CIRCUMFERENTIALLY SEALING SECUREMENT DRESSING

(71) Applicant: Robert E. Helm, Rye Beach, NH (US)

(72) Inventor: Robert E. Helm, Rye Beach, NH (US)

(73) Assignee: One IV Solutions, LLC, Dunnellon, FL (US)

( * ) Notice: Subject to any disclaimer, the term of this patent is extended or adjusted under 35 U.S.C. 154(b) by 0 days.

(21) Appl. No.: 15/044,945

(22) Filed: Feb. 16, 2016

(65) Prior Publication Data

US 2016/0158523 A1 Jun. 9, 2016

Related U.S. Application Data

(60) Continuation-in-part of application No. 14/741,596, filed on Jun. 17, 2015, which is a division of
(Continued)

(51) Int. Cl.
*A61M 25/02* (2006.01)
*A61M 39/10* (2006.01)
(Continued)

(52) U.S. Cl.
CPC .......... *A61M 39/162* (2013.01); *A61M 25/02* (2013.01); *A61M 39/10* (2013.01);
(Continued)

(58) Field of Classification Search
CPC .. A61M 2025/0253; A61M 2025/0266; A61M 2025/028; A61M 2039/1033;
(Continued)

(56) References Cited

U.S. PATENT DOCUMENTS 2,461,891 A 2/1949 Giles
3,198,385 A 8/1965 Maxwell
(Continued)

FOREIGN PATENT DOCUMENTS

DE 3140192 A1 4/1983
EP 1344539 A2 9/2003
(Continued)

OTHER PUBLICATIONS

[No Author Listed] Alibaba.com Product Literature—IV Catheter Dressing (accessed Nov. 17, 2010).
(Continued)

*Primary Examiner* — Quynh-Nhu H. Vu
(74) *Attorney, Agent, or Firm* — Stoel Rives LLP

(57) ABSTRACT

Devices and methods are provided for sealing a catheter insertion site to maintain sterility. In one aspect of the invention, mounting handle/dressing assemblies and kits are disclosed for creating a sterile sealed environment around a catheter insertion site. For example the dressings of the present invention can be pre-disposed around a mounting handle and connector. The connector is joined to the proximal end of the catheter and then the dressing can be slid along the mounting handle until it surrounds the insertion site. Once the dressing is adhesively applied to the skin and locked into place by an annular fitting between the dressing and the connector, the handle can be removed and discarded, leaving only the dressing, and catheter connector in place. The catheter connector preferably has a needle-free connector port at its proximal end for connection to IV lines or other infusion devices.

13 Claims, 52 Drawing Sheets

Related U.S. Application Data application No. 13/613,509, filed on Sep. 13, 2012, now Pat. No. 9,180,275, which is a continuation-in-part of application No. 13/349,909, filed on Jan. 13, 2012, now Pat. No. 9,815,242, application No. 15/044,945, filed on Feb. 16, 2016, which is a continuation-in-part of application No. 12/914,160, filed on Oct. 28, 2010, now Pat. No. 9,808,601.

(60) Provisional application No. 61/534,981, filed on Sep. 15, 2011, provisional application No. 61/437,862, filed on Jan. 31, 2011, provisional application No. 61/482,124, filed on May 3, 2011, provisional application No. 61/482,564, filed on May 4, 2011, provisional application No. 61/255,927, filed on Oct. 29, 2009, provisional application No. 62/116,249, filed on Feb. 13, 2015, provisional application No. 62/267,155, filed on Dec. 14, 2015.

(51) Int. Cl.
*A61M 39/18* (2006.01)
*A61M 25/06* (2006.01)
*A61M 39/16* (2006.01)

(52) U.S. Cl.
CPC ......... *A61M 39/18* (2013.01); *A61M 25/0631* (2013.01); *A61M 2025/028* (2013.01); *A61M 2025/0253* (2013.01); *A61M 2025/0266* (2013.01); *A61M 2039/1033* (2013.01)

(58) Field of Classification Search
CPC .. A61M 25/02; A61M 25/0631; A61M 39/10; A61M 39/162; A61M 39/18
See application file for complete search history.

(56) References Cited

U.S. PATENT DOCUMENTS

| | | | |
|---|---|---|---|
| 3,683,911 A | 8/1972 | McCormick | |
| 3,900,026 A * | 8/1975 | Wagner | A61M 25/02 128/888 |
| 3,918,446 A | 11/1975 | Buttaravoli | |
| 4,016,879 A | 4/1977 | Mellor | |
| 4,079,738 A * | 3/1978 | Dunn | A61M 25/0111 604/164.05 |
| 4,327,723 A | 5/1982 | Frankhouser | |
| 4,380,234 A * | 4/1983 | Kamen | A61M 25/02 604/180 |
| 4,392,853 A | 7/1983 | Muto | |
| 4,464,178 A | 8/1984 | Dalton | |
| 4,515,592 A | 5/1985 | Frankhouser | |
| 4,551,136 A | 11/1985 | Mandl | |
| 4,551,137 A | 11/1985 | Osborne | |
| 4,563,177 A | 1/1986 | Kamen | |
| 4,633,863 A * | 1/1987 | Filips | A61M 25/02 128/846 |
| 4,634,433 A | 1/1987 | Osborne | |
| 4,767,411 A | 8/1988 | Edmunds | |
| 4,781,695 A | 11/1988 | Dalton | |
| 4,840,613 A | 6/1989 | Balbierz | |
| 4,898,587 A * | 2/1990 | Mera | A61M 25/02 128/DIG. 26 |
| 4,966,590 A | 10/1990 | Kait | |
| 4,997,421 A | 3/1991 | Plasrok et al. | |
| 5,007,901 A | 4/1991 | Shields | |
| 5,074,847 A | 12/1991 | Greenwell | |
| 5,112,313 A * | 5/1992 | Sallee | A61M 25/0612 604/180 |
| 5,116,324 A | 5/1992 | Brierley et al. | |
| 5,215,532 A | 6/1993 | Atkinson | |
| 5,232,453 A | 8/1993 | Plass et al. | |
| 5,238,010 A | 8/1993 | Grabenkort et al. | |
| 5,330,438 A * | 7/1994 | Gollobin | A61M 25/0637 604/110 |
| 5,336,195 A | 8/1994 | Daneshvar | |
| 5,344,415 A | 9/1994 | DeBusk et al. | |
| 5,372,589 A | 12/1994 | Davis | |
| 5,380,294 A | 1/1995 | Persson | |
| 5,415,642 A | 5/1995 | Shepard | |
| D359,120 S | 6/1995 | Sallee et al. | |
| 5,478,326 A | 12/1995 | Shiu | |
| 5,527,277 A | 6/1996 | Ensingmer | |
| 5,531,695 A * | 7/1996 | Swisher | A61M 39/1011 285/45 |
| 5,577,516 A | 11/1996 | Schaeffer | |
| 5,662,616 A | 9/1997 | Bousquet | |
| 5,685,865 A | 11/1997 | Cosgrove et al. | |
| 5,686,096 A | 11/1997 | Khan et al. | |
| 5,690,612 A | 11/1997 | Lopez et al. | |
| 5,694,686 A | 12/1997 | Lopez | |
| 5,702,371 A | 12/1997 | Bierman | |
| 5,707,348 A | 1/1998 | Krogh | |
| 5,715,815 A | 2/1998 | Lorenzen et al. | |
| 5,722,959 A | 3/1998 | Bierman | |
| 5,758,660 A | 6/1998 | Lokken | |
| 5,769,807 A | 6/1998 | Haddock et al. | |
| 5,772,636 A | 6/1998 | Brimhall et al. | |
| 5,776,106 A * | 7/1998 | Matyas | A61M 25/02 128/DIG. 26 |
| 5,807,341 A | 9/1998 | Heim | |
| 5,820,607 A | 10/1998 | Tcholakian | |
| 5,885,254 A | 3/1999 | Matyas | |
| 5,989,220 A | 11/1999 | Shaw et al. | |
| 6,080,138 A | 6/2000 | Lemke et al. | |
| 6,099,509 A | 8/2000 | Brown, Jr. et al. | |
| 6,132,399 A | 10/2000 | Schultz | |
| 6,302,867 B1 | 10/2001 | Brown, Jr. et al. | |
| 6,375,639 B1 | 4/2002 | Duplessie et al. | |
| 6,413,240 B1 | 7/2002 | Bierman et al. | |
| 6,569,121 B1 | 5/2003 | Purow et al. | |
| 6,571,395 B1 | 6/2003 | Korkor | |
| 6,809,230 B2 | 10/2004 | Hancock et al. | |
| 6,827,707 B2 * | 12/2004 | Wright | A61M 25/02 604/174 |
| 7,083,598 B2 | 8/2006 | Liska | |
| 7,153,291 B2 | 12/2006 | Bierman | |
| 7,244,245 B2 | 7/2007 | Purow et al. | |
| 7,247,150 B2 | 7/2007 | Bierman | |
| 7,544,166 B2 | 6/2009 | Davis et al. | |
| 7,578,804 B2 | 8/2009 | Bierman | |
| 7,723,561 B2 | 5/2010 | Propp | |
| 7,744,572 B2 | 6/2010 | Bierman | |
| D622,376 S | 8/2010 | McFalls | |
| 7,799,001 B2 | 9/2010 | Bierman | |
| 7,806,873 B2 | 10/2010 | Dikeman et al. | |
| 8,435,216 B2 | 5/2013 | Spinoza | |
| 2002/0082559 A1 | 6/2002 | Chang et al. | |
| 2002/0092529 A1 | 7/2002 | Rozier et al. | |
| 2003/0073540 A1 | 4/2003 | Saulenas et al. | |
| 2003/0201639 A1 | 10/2003 | Korkor | |
| 2005/0011568 A1 * | 1/2005 | Kagenow | A61M 25/02 138/110 |
| 2005/0065479 A1 | 3/2005 | Schiller et al. | |
| 2005/0113798 A1 | 5/2005 | Slater et al. | |
| 2005/0119619 A1 | 6/2005 | Haining | |
| 2005/0209584 A1 | 9/2005 | Rome | |
| 2005/0256461 A1 | 11/2005 | DiFiore | |
| 2005/0261623 A1 | 11/2005 | Propp | |
| 2005/0267400 A1 | 12/2005 | Haarala et al. | |
| 2006/0030820 A1 | 2/2006 | Alheidt et al. | |
| 2006/0189910 A1 * | 8/2006 | Johnson | A61F 13/0203 602/42 |
| 2006/0211994 A1 | 9/2006 | Roman et al. | |
| 2006/0247577 A1 | 11/2006 | Wright | |
| 2006/0247582 A1 | 11/2006 | Alheidt et al. | |
| 2006/0264836 A1 | 11/2006 | Bierman | |
| 2007/0027429 A1 | 2/2007 | Kuracina et al. | |
| 2007/0055205 A1 | 3/2007 | Wright et al. | |
| 2007/0060892 A1 | 3/2007 | Propp | |
| 2007/0106222 A1 * | 5/2007 | Bennett | A61M 5/158 604/174 |

(56) References Cited

U.S. PATENT DOCUMENTS

| | | | |
|---|---|---|---|
| 2008/0058692 A1 | 3/2008 | Propp et al. | |
| 2008/0063695 A1* | 3/2008 | Vitaris | A61F 13/023 424/443 |
| 2008/0125750 A1 | 5/2008 | Gaissert | |
| 2008/0221531 A1 | 9/2008 | Alheidt et al. | |
| 2008/0262439 A1 | 10/2008 | Alheidt | |
| 2009/0118696 A1 | 5/2009 | Nyhart, Jr. | |
| 2009/0192470 A1 | 5/2009 | Propp | |
| 2009/0149814 A1* | 6/2009 | Bailey | A61M 25/02 604/180 |
| 2009/0306602 A1 | 12/2009 | Elwell et al. | |
| 2010/0100049 A1* | 4/2010 | Godfrey | A61M 25/02 604/180 |
| 2010/0106103 A1 | 4/2010 | Ziebol et al. | |
| 2010/0106106 A1 | 4/2010 | Ziebol et al. | |
| 2010/0179482 A1 | 7/2010 | Wright et al. | |
| 2011/0106014 A1 | 5/2011 | Helm, Jr. | |
| 2012/0197204 A1 | 8/2012 | Helm, Jr. | |
| 2012/0232489 A1 | 9/2012 | Helm, Jr. | |
| 2013/0178825 A1 | 7/2013 | Helm, Jr. | |

FOREIGN PATENT DOCUMENTS

| | | |
|---|---|---|
| WO | 94/05239 A1 | 3/1994 |
| WO | 9702848 A1 | 1/1997 |
| WO | 2008117078 A1 | 10/2008 |

OTHER PUBLICATIONS

[No Author Listed] Become.com Product Literature—3m Catheter Dressing (accessed Nov. 17, 2010).
[No Author Listed] IV Team, BD Announces UK Launch of new BD Nexiva(TM) Closed IV Catheter System Designed to Help Protect Healthcare Workers, PR Newswire.com Jul. 29, 2009.
[No Author Listed] Seattle Treatment Education Project, The Body, The Facts About Intravenous Catheter Lines, thebody.com, Oct. 1992.
[No Author Listed] Silverlon® "Lifesaver™ Ag" 7 Day Antimicrobial IV/ Catheter Dressing product Literature, Silverlon.com (accessed Nov. 17, 2010).
[No Author Listed] Smith & Nephew Product Literature—I.V. and Catheter Sites, smith-nephew.com (accessed Nov. 17, 2010).
[No Author Listed] Sorbaview Shield Product Literature, centurionmp.com (accesed Nov. 17, 2010).
[No Author Listed] Walgreens.com Product Literature—Medline Suresite I.V. Transparent Cathter Dressing 2x3 (acccessed Nov. 17, 2010).
[Austrailian Office Action dated Jun. 20, 2012 for application No. 2010319924 (5 pages).
Clemens, Mary, New IV Dressing Benefits Both the Patient and Clinician, Reuters.com, Feb. 2, 2009.
International Search Report and Written Opinion dated Jul. 20, 2011 for Application No. PCT/US2010/054427.
International Search Preliminary Report on Patentability for Application No. PCT/US2010/054427 dated May 10, 2012 (7 pages).
Inernational Search Report and Written Opinion dated Aug. 17, 2012 for Application No. PCT/US2012/021196 (12 pages).
Johnson, Maree, M.D., Systematic Review Central Line Dressing Type and Frequency, Joanne Briggs Institute, Jan. 20, 1998.
Maki DG, and Ringer M,, Evaluation of dressing regimens for prevention of infection with peripheral intravenous catheters. Gauze, a transparent polyurethane dressing, and an idophor-transparent dressing., JAMA. Nov. 6, 1987;258(17): 2396-403., pubmed.gov.
McGee David C., M.D. and Michael K. Gould, M.D., Preventing Complcations of Central Venous Catheterizations, N Engl J Med 2003; 348; 1123-1133.
Australian Office Action dated Nov. 1, 2012 for Application No. 2010319924 (3 pages).
Supplemental European Search Report dated Apr. 18, 2013 for Application No. 1-830440.3 (7 pages).
Examiner Report received in CA Application No. 2,779,137 dated Sep. 1, 2016; 4 pages.
Office Action received in CA Application No. 2,779,137 dated Mar. 24, 2017; 4 pages.
Office Action received in CN Application No. 2010800601501 dated May 11, 2015; 8 pages.
Extended European Search Report received in EP Application No. 12741663.4 dated Sep. 21, 2017; 12 pages.
Office Action for related U.S. Appl. No. 15/044,994; dated Feb. 13, 2018, 19 pages.
Office Action dated Jan. 17, 2018 for U.S. Appl. No. 15/044,945.
Office Action dated Apr. 9, 2019 for U.S. Appl. No. 15/044,994.

* cited by examiner

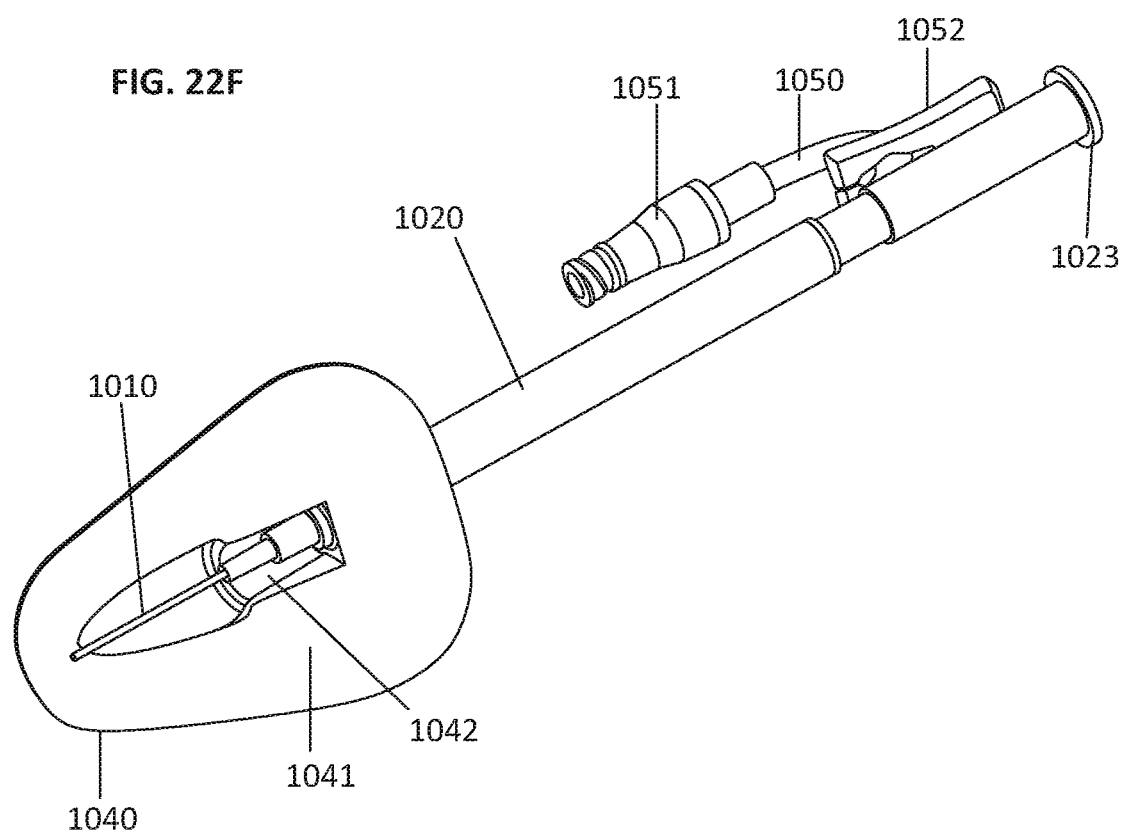

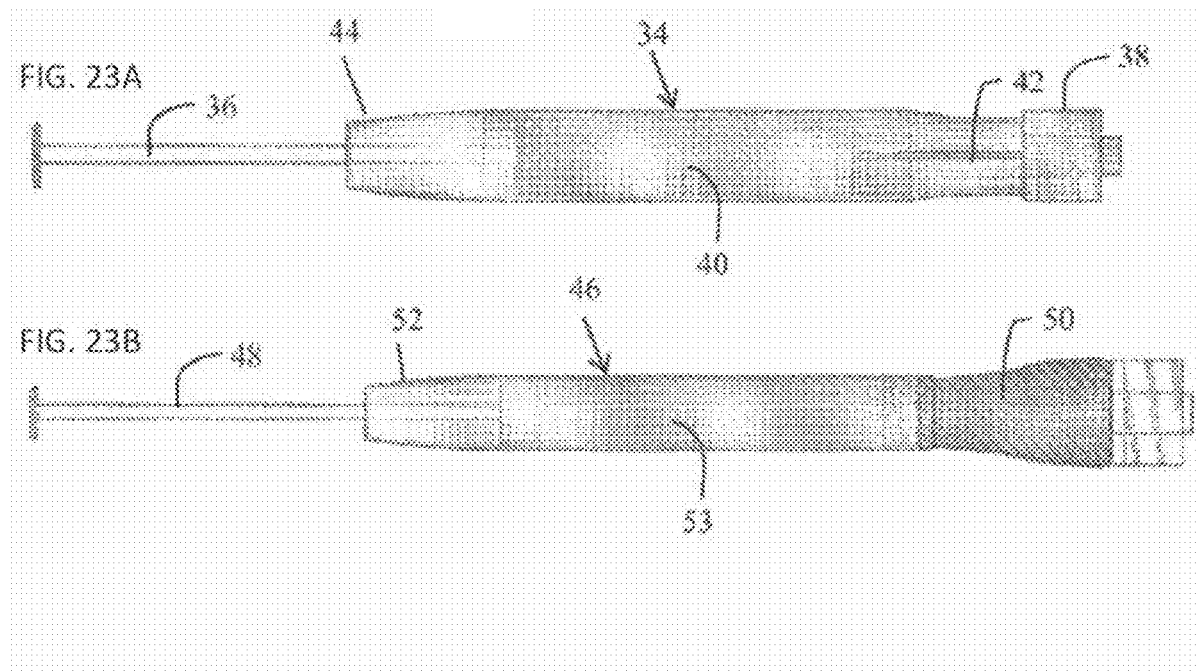

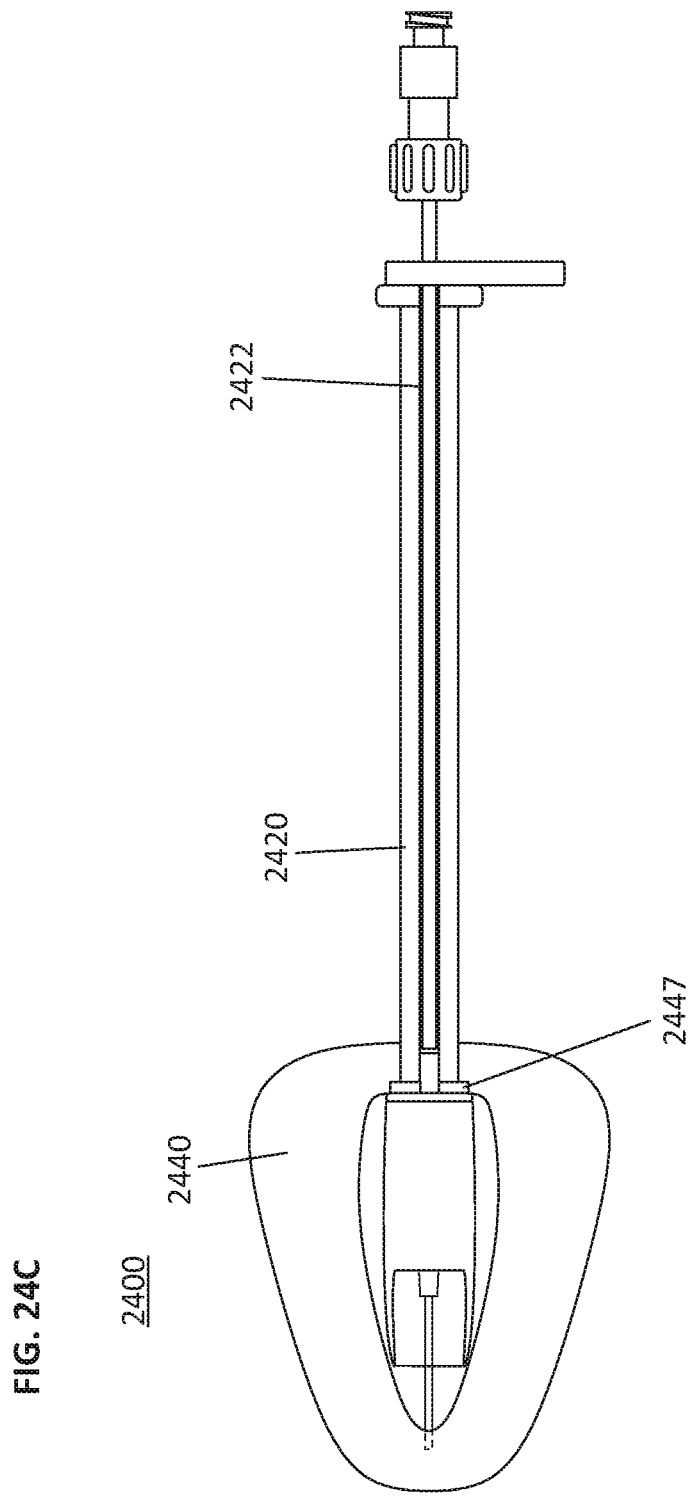

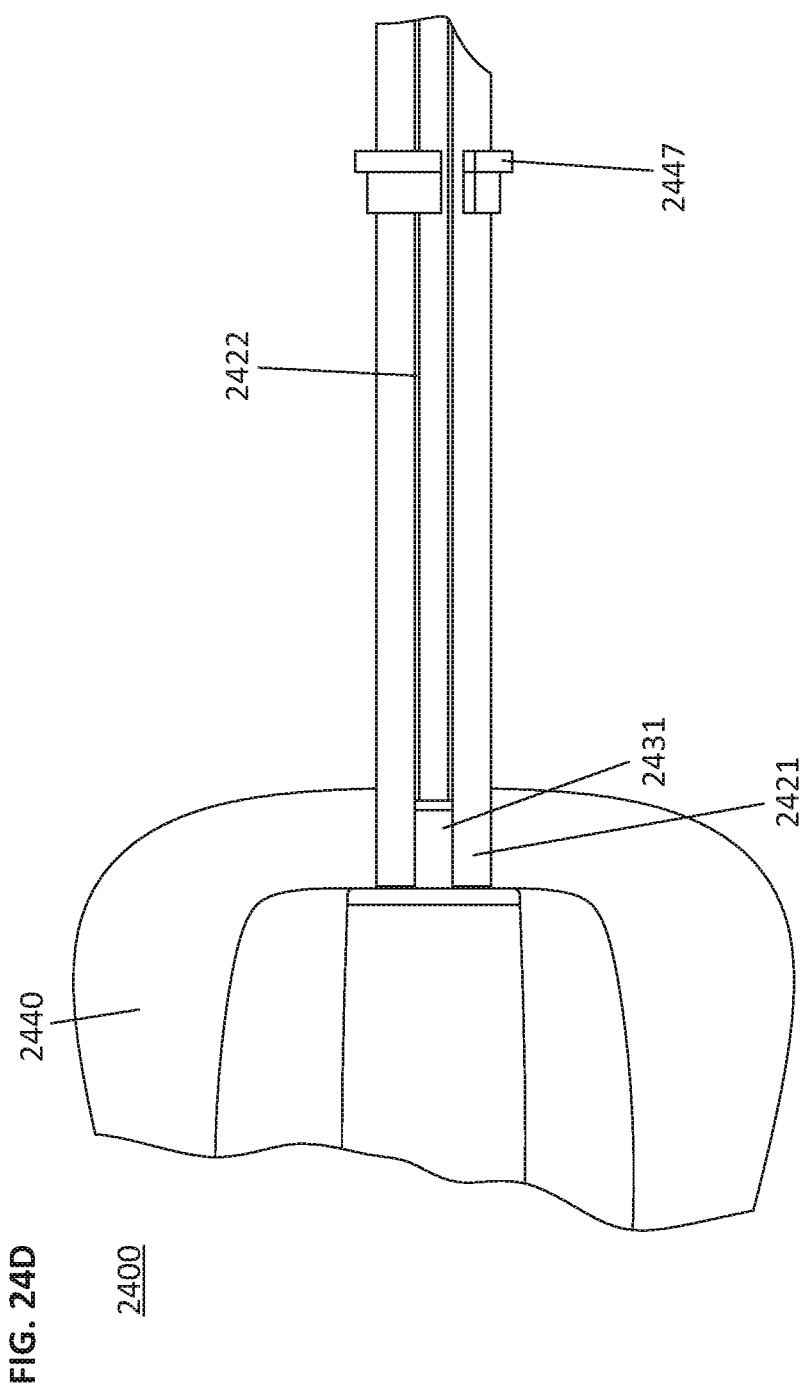

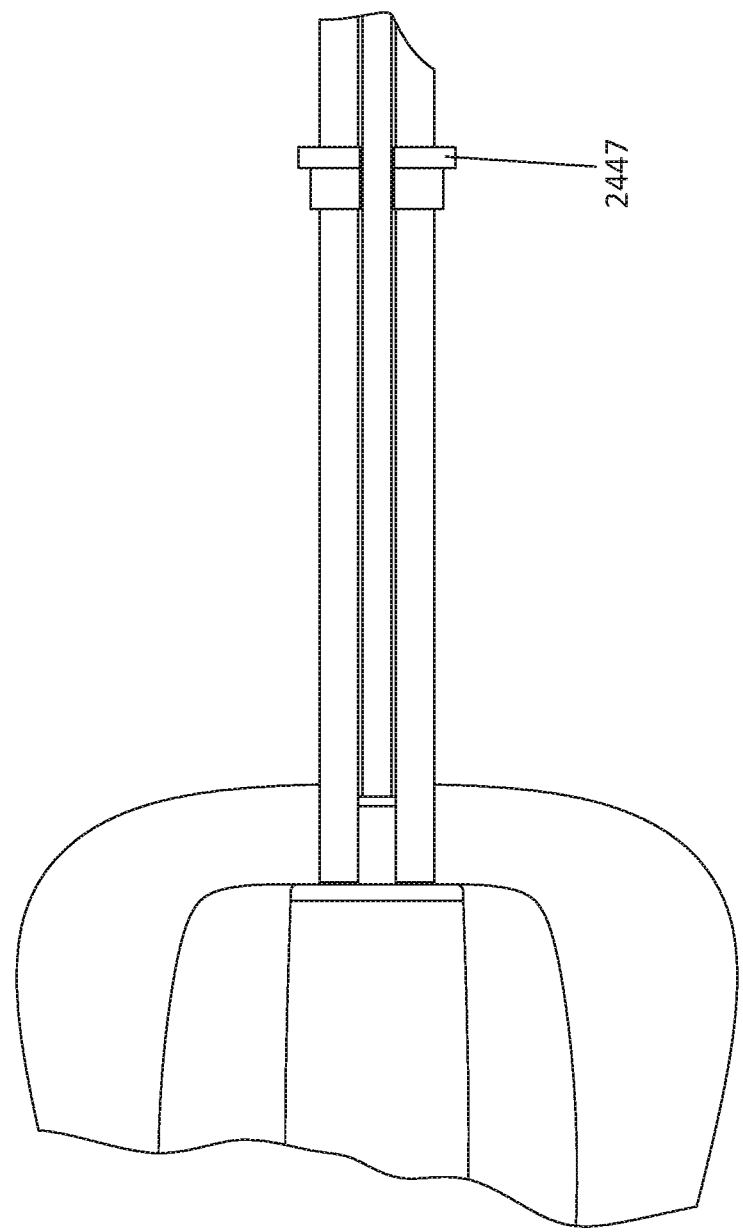

CATHETER EXTENSION WITH INTEGRATED CIRCUMFERENTIALLY SEALING SECUREMENT DRESSING

RELATED APPLICATIONS

This application is a continuation-in-part of U.S. patent application Ser. No. 14/741,596 filed Jun. 17, 2015, which is a divisional of U.S. patent application Ser. No. 13/613,509 filed Sep. 13, 2012, (now U.S. Pat. No. 9,180,275 issued Nov. 10, 2015) entitled "Catheter Dressing Systems with Integrated Flushing Mechanisms," which claims priority to U.S. Provisional Patent Application No. 61/534,981 filed Sep. 15, 2011, each of which is incorporated herein in its entirety. U.S. patent application Ser. No. 14/613,509 is also a continuation-in-part of U.S. patent application Ser. No. 13/349,909 filed Jan. 13, 2012 (now U.S. Pat. No. 8,715,242 issued May 6, 2014) entitled "Snap-Seal, Sterile, Intravascular Catheter System," which claims priority to U.S. Provisional Patent Application No. 61/437,862 filed Jan. 31, 2011, U.S. Provisional Patent Application No. 61/482,124 filed May 3, 2011, and U.S. Provisional Patent Application No. 61/482,564 filed May 4, 2011, each of which is also incorporated herein in its entirety.

This application is also a continuation-in-part of U.S. patent application Ser. No. 12/914,160 filed Oct. 28, 2010 entitled "Sealed Sterile Catheter Dressings," which claims priority to U.S. Provisional Patent Application No. 61/255,927 filed Oct. 29, 2009, each of which is also incorporated herein by reference in its entirety.

This application also claims priority to U.S. Provisional Patent Applications No. 62/116,249 filed Feb. 13, 2015 and U.S. Provisional Patent Application No. 62/267,155 filed Dec. 14, 2015, likewise incorporated by reference in their entireties.

FIELD OF THE INVENTION

The present invention relates to methods and devices for sealing medical devices, and in particular to methods and devices for sealing and maintaining sterility at a catheter insertion site.

BACKGROUND OF THE INVENTION

The insertion of a catheter into a body cavity, duct, or vessel to allow drainage, injection of fluids, and/or access by surgical instruments is a common procedure in the practice of medicine. Catheters come in a variety of shapes and forms and can be used for a variety of tasks, including chemotherapy, fluid drainage, hemodialysis, and administering intravenous fluids, anesthesia, or other medications. A peripheral intravascular catheter can be used to administer medication, nutrition, and various other intravenous fluids via peripheral blood vessels, to perform hemodynamic measurements, and to provide access for procedures and devices affecting the cardiovascular system. A central venous catheter can be used to deliver medications or fluids to vessels near the heart or into the heart itself. It is estimated that more than 100 million peripheral venous catheters and more than 250,000 central venous catheters are placed in patients in the United States each year. Other intravascular catheters include those used for hemodialysis, peripheral central access (PIC), interventional procedure access, cardiac ventricular assist device access, and other long term vascular access support. These can be both arterial and venous in respect to the type of vessel in which they are inserted. For these many intravascular catheter uses, the catheter insertion site is traditionally and universally dressed by pressing the round, tubular catheter against the skin of the patient with a sterile adhesive patch-type dressing or with sterile gauze and adhesive tape, which are the two dressing types recommended by the United States Centers for Disease Control and Prevention ("CDC").

One major problem with intravascular catheterization methods is the risk of infection. For example, infections related to central venous catheters alone occur up to 80,000 times per year in the U.S., leading to 28,000 deaths and costing as much as 2.3 billion dollars per year. The rise of multi-drug resistant organisms has further compounded the magnitude of the problem of intravascular catheter infection, and the lay press and medical literature have paid increasing attention to this problem. As a very significant marker of this concern, the Centers for Medicare and Medicaid recently ruled that costs associated with catheter-related infection will no longer be reimbursed. Because of this, there has been a very strong push by clinicians, hospitals, and insurers to address the problem of catheter related infection. Several improved strategies for catheter care have been introduced, such as using rigorous interval dressing change protocols, applying optimal catheter care techniques, using antibiotic impregnated catheters, using improved dressing materials, and/or supplying antimicrobial additives to the dressing composition.

All of these strategies, however, still have the fundamental drawback of working within the mechanical constraints of the "traditional" patch-type covering dressing. This dressing strategy, which has been used since the first intravascular catheter was placed more than 100 years ago, acts, as stated above, by pressing the tubular catheter against the skin with a flat adhesive dressing that serves to cover both the catheter-skin insertion site and a portion of the catheter external to the body. The fundamental shortcoming of this traditional dressing strategy is that it precludes the creation of a sterile seal at the catheter-skin insertion site, as a gap between the round contour of the catheter and the skin is always left. The size of this gap is larger if the dressing is attached to wider diameter points of the catheter device, such as a catheter hub or an intermediate connector. Inflow of contaminants to the catheter insertion site along these open channels is always a possibility with such methods and devices, and therefore true sterility can never be achieved. In addition, over time, movement of the skin and catheter relative to one another and relative to the dressing can increase the size of the catheter-dressing gap. Furthermore, these dressings cannot be exposed to water or other liquids as these liquids will flow directly to the catheter-skin insertion site, thereby further contaminating this site.

Accordingly, there is a need for catheter dressing methods and devices that provide for improved sealing at the catheter-dressing junction and/or improved sterility at the catheter insertion site. The devices and methods disclosed herein represent a paradigm shift in intravascular catheter care from a non-sterile, non-sealing dressing to a fully sealed and durably-sterile solution.

SUMMARY OF THE INVENTION

Methods and devices are disclosed for dressing and/or sealing a catheter insertion site.

In one aspect, a catheter dressing is provided that can include an adhesive plate configured for attachment to the skin of a patient and a flexible sheath having a proximal end and a distal end and extending proximally from the adhesive plate. The sheath is capable of longitudinal extension from a compressed to an extended state and configured in its extended state to surround an external segment of a catheter implanted in the patient and circumferentially seal to a portion of the external segment at a distance from the adhesive plate. The sheath can define a sealed chamber around the external segment of the catheter and a portion of the patient. In one embodiment, movement of the catheter with respect to the patient does not disrupt a seal formed between the sheath and the catheter. The sheath can optionally be coupled to the catheter. The sheath can include a splitable seam formed therein and can be capable of being opened along the seam such that the catheter dressing can be removed from a catheter around which the dressing is installed. In one embodiment, the seam can include a non-full-thickness perforation.

The sheath can include an attachment mechanism, such as a friction coupler, a threaded coupler, an inflation coupler, an electromagnetic coupler, and/or an adhesive. In one embodiment, the attachment mechanism can be attached to the adhesive plate. The sheath can also include a stretchable gasket ring at its proximal end for sealing to the portion of the external segment of the catheter and the portion of the external segment of the catheter can include an annular groove for receiving the stretchable gasket ring. At least a portion of the sheath can be transparent and the sheath can include an access portal and/or an absorbent member disposed therein. In one embodiment, the sealed chamber can be sterile. In certain embodiments, the sheath can be formed integrally with the catheter. In one embodiment, the external segment of the catheter can include one or more of a catheter body, a catheter hub, a MicroCLAVE-type needleless connector, and/or a Luer-type connector. The sheath can be formed of at least one of an antibiotic-impregnated material and an antimicrobial-impregnated material and/or at least one of an antibiotic secreting member and an antimicrobial secreting member can be disposed within the sheath.

In another exemplary embodiment, the catheter dressing can include a clamp configured to secure at least one of the sheath and the external segment of the catheter to the patient. The clamp can also be configured to apply a compressive force to the gasket ring of the sheath and/or to increase the integrity of a seal formed between the sheath and the external segment of the catheter.

In another embodiment, the dressing can include a coupling member configured for coupling to a terminal end of the external segment of the catheter, the coupling member having at least one lumen to provide a fluid flow path to or from the catheter. The sheath can be extendable between the adhesive plate and the coupling member to surround a longitudinal segment of the catheter. In one embodiment, the sheath is configured to restrict longitudinal movement of the external segment of the catheter relative to the patient while permitting non-longitudinal movement of the external segment of the catheter relative to the patient. The sheath can also be formed integrally with the coupling member, and/or the coupling member can be directly attached to the adhesive plate. The coupling member can be any of a valve, a catheter body, a catheter hub, a Luer-type connector, a MicroCLAVE-type connector, a threaded fitting, and/or a friction fitting. In one embodiment, a kit is provided that includes the catheter dressing and a catheter having a mating feature for attachment of the catheter to the catheter dressing.

In another aspect, a catheter dressing assembly is provided that can include an adhesive plate configured for attachment to the skin of a patient, a coupling member configured for coupling to an external end of a catheter implanted in the patient, the coupling member having at least one lumen to provide a fluid flow path to or from the catheter, and a flexible sheath extendable between the adhesive plate and the coupling member to surround a longitudinal segment of the catheter. The sheath can include an attachment mechanism for attaching the sheath to the coupling member, such as a friction coupler, a threaded coupler, an inflation coupler, an electromagnetic coupler, and/or an adhesive. In one embodiment, the attachment mechanism can be attached to the adhesive plate. The sheath can also include a stretchable gasket ring at its proximal end for sealing to the coupling member and the coupling member can include an annular groove for receiving the stretchable gasket ring. At least a portion of the sheath can be transparent and the sheath can include an access portal. The dressing assembly can also include an absorbent member disposed within the sheath. The sheath can define a sealed chamber around the end of the catheter and a portion of the patient. In one embodiment, the sealed chamber can be sterile. The sheath can be formed integrally with the coupling member and/or the coupling member can be directly attached to the adhesive plate. In such embodiments, movement of the catheter with respect to the patient does not disrupt a seal formed between the sheath and the coupling member.

The sheath can be formed of at least one of an antibiotic-impregnated material or an antimicrobial-impregnated material capable of secreting an antibiotic or antimicrobial agent.

In another embodiment, the dressing assembly can include a clamp configured to secure at least one of the sheath and the coupling member to the patient. The clamp can also be configured to apply a compressive force to the gasket ring of the sheath and/or to increase the integrity of a seal formed between the sheath and the external segment of the catheter.

In another exemplary embodiment, the coupling member can include a valve, a catheter body, a catheter hub, a Luer-type connector, a MicroCLAVE-type connector, a threaded fitting, and/or a friction fitting.

In another aspect, a method for circumferentially sealing a catheter insertion site is provided. The method can include inserting a distal end of a catheter into a patient at an insertion site, connecting a proximal end of the catheter to a coupling member having a flexible sheath extendable therefrom, extending the sheath along an external segment of the catheter to the patient, and adhesively sealing a distal end of the sheath circumferentially around the catheter insertion site. The method can also include unsealing the distal end of the sheath and disconnecting the proximal end of the catheter from the coupling member.

The method can further include moving the catheter with respect to the patient without disrupting a seal formed between the sheath and the catheter or coupling member. The method can also include effecting and maintaining a sterile seal around the insertion site and/or securing at least one of the sheath and the external segment of the catheter to the patient. The method can include moving the catheter with respect to the patient without disrupting a seal formed between the sheath and the coupling member, applying a sterilizing agent to an interior volume of the sheath through an access portal formed in a sidewall of the sheath, and/or applying sterilizing radiation to an internal volume of the sheath. The sterilizing agent can include at least one of an antibiotic solution, an antimicrobial solution, and a sterilization gas. The method can also include removing a sample from the internal volume of the sheath through an access portal formed in a sidewall of the sheath and testing the sample. The method can also include separating the dressing along a non-full-thickness perforation formed in a sidewall of the dressing.

In another aspect, a method is provided for circumferentially sealing a catheter insertion site. The method includes inserting a distal end of a catheter into a patient at an insertion site, the catheter having a flexible sheath extendable therefrom, extending the sheath along an external segment of the catheter to the patient, and sealing a distal end of the sheath circumferentially around the catheter insertion site.

In yet another aspect, a catheter and dressing assembly is provided that includes a catheter and an integrated dressing comprising an adhesive plate and a flexible sheath having a proximal end joined to the catheter and a distal end joined to the adhesive plate. The sheath is capable of longitudinal extension from a compressed to an extended state and configured in its extended state to surround an external segment of the catheter when implanted in the patient and the adhesive plate is configured for attachment to the patient's skin to provide a circumferential seal.

In one embodiment, movement of the catheter with respect to the patient does not disrupt a seal formed between the sheath and the catheter. The sheath can also include a stretchable gasket ring at its proximal end for sealing to the portion of the external segment of the catheter. The sheath can also include an attachment mechanism, such as a friction coupler, a snap-fit coupler, a threaded coupler, an inflation coupler, an electromagnetic coupler, or an adhesive. The external segment of the catheter can be any of a catheter body, a catheter hub, a MicroCLAVE-type connector, and a Luer-type connector, and can include an annular groove for receiving the stretchable gasket ring. At least a portion of the sheath can be transparent, and an absorbent member can be disposed within the sheath. The sheath can define a sealed chamber around the external segment of the catheter and a portion of the patient and the sealed chamber can be sterile. The sheath can include an access portal and can be formed integrally with the catheter. The assembly can also include a clamp configured to secure at least one of the sheath and the external segment of the catheter to the patient. The clamp can be configured to increase the integrity of a seal formed between the sheath and the external segment of the catheter. The sheath can also include a stretchable gasket ring at its proximal end for sealing to the portion of the external segment of the catheter and the clamp can be configured to apply a compressive force to the gasket ring. In one embodiment, the attachment mechanism is attached to the adhesive plate.

In another aspect, a removable catheter dressing is provided that includes an adhesive plate configured for attachment to the skin of a patient and a flexible sheath having a proximal end and a distal end and extending proximally from the adhesive plate, the flexible sheath having a longitudinal seam formed therein. The sheath is capable of being opened along the seam such that the catheter dressing can be removed from a catheter around which the dressing is installed. In one embodiment, the seam can be a non-full-thickness perforation.

In yet another aspect, a method is provided for removing a catheter dressing from a catheter that is at least partially inserted into a patient. The method includes separating the dressing from the tether, e.g., along a longitudinal non-full-thickness perforation formed in a sidewall of the dressing.

In another aspect, a catheter dressing is provided that includes an adhesive plate configured for attachment to the skin of a patient and a flexible sheath having a proximal end and a distal end and extending proximally from the adhesive plate, the flexible sheath having a longitudinal opening formed therein. The sheath is capable of being placed around an installed catheter and closed along the opening to circumferentially seal an external portion of the installed catheter at a distance from the adhesive plate. The dressing can also include a mating mechanism configured to selectively mate first and second free edges of the sheath to one another along the opening. The mating mechanism can include any of a friction-based closure, an adhesive closure, a latch-type closure, and a male-female closure.

In yet another aspect, a method is provided for replacing a catheter dressing. The method includes removing a first catheter dressing circumferentially sealed around an external portion of a catheter that is at least partially inserted into a patient, placing a second catheter dressing having a longitudinal opening around the external portion of the catheter, and sealing the opening of the second catheter dressing to circumferentially seal the external portion of the catheter. The method can also include securing the external portion of the catheter to the patient with the second catheter dressing such that longitudinal movement of the external portion of the catheter relative to the patient is restricted and non-longitudinal movement of the external segment of the catheter relative to the patient is permitted. The method can also include at least one of sterilizing and cleaning a site at which the catheter is inserted into the patient after removing the first catheter dressing and before placing the second catheter dressing. In one embodiment, sealing the opening includes joining first and second free edges of the second catheter dressing, which can optionally include mating at least one of a friction-based closure, an adhesive closure, a latch-type closure, and a male-female closure formed thereon. The method can also include clamping a sheath portion of the second catheter dressing to an exterior surface of a catheter hub with a circumferential support ring and/or reinforcing a seal between an adhesive plate portion of the second catheter dressing and a skin of the patient by applying a circular adhesive ring, the circular adhesive ring having an outer diameter that is greater than an outer diameter of the adhesive plate portion.

In another aspect, a catheter dressing is provided that includes a unitary body having a planar distal adhesive surface defining a distal opening, a proximal portion defining a proximal opening, and an interior chamber extending from the proximal opening to the distal opening. The proximal opening is configured to form a circumferential seal around a catheter that is at least partially inserted into a patient and the distal adhesive surface is configured to adhere to the patient's skin to form a circumferential seal around a skin site at which the catheter is inserted. The body includes a splitable seam along which the body can be selectively opened and resealed. The body can be rigid or semi-rigid such that the body restricts movement of the catheter relative to the patient and the body can include an access portal. The proximal opening can be formed perpendicular to the planar distal adhesive surface.

In yet another aspect, a catheter is provided that includes an elongate tubular body having proximal and distal ends and defining a central lumen. The body includes a mating feature for mating to a catheter dressing such that a sheath portion of the dressing can be coupled to the mating feature and extended towards a patient to create a circumferential sterile seal around an opening in the patient through which at least a portion of the body is inserted.

In another aspect, the methods and devices can be used to achieve a sterile seal when placing a catheter using a Seldinger technique. For example, the dressing can be placed over a catheter tip, and the proximal end of the dressing can be attached to the catheter hub prior to insertion of the catheter over a guide wire. Once the catheter is positioned, the dressing can be unfurled and an adhesive plate at the distal end of the dressing can be attached to the skin around the catheter insertion site to provide a circumferential seal. The dressing can also be either pre-attached to the catheter or can be formed integrally therewith.

In another aspect, the sealed chamber can be accessed via one or more sheath access portals to introduce cleaning, sanitizing and/or antimicrobial agents. In one embodiment, a sterilizing agent such as an antibiotic solution or a sterilization gas can be applied to an interior volume of the sheath through an access portal formed in a sidewall of the sheath.

In yet another embodiment, the sheath can be transparent to sterilizing radiation, such as UV radiation, and the method can further comprise sterilizing or maintaining the sterility of the dressing's sealed chamber before, during, or after deployment of the dressing.

In a further embodiment a method for circumferentially sealing a catheter insertion site is provided that can include inserting a distal end of a catheter into a patient at an insertion site, the catheter having a flexible sheath extendable therefrom and extending the sheath along an external segment of the catheter to the patient. The method can also include adhesively sealing a distal end of the sheath circumferentially around the catheter insertion site.

In another aspect of the invention, mounting handle/dressing assemblies and kits are disclosed for creating a sterile sealed environment around a catheter insertion site. For example, the dressings of the present invention can be pre-disposed around a releasable mounting handle and connector. The connector is joined to the proximal end of the catheter and then the dressing can be slid along the mounting handle until it surrounds the catheter and catheter insertion site. Once the dressing is adhesively applied to the skin and locked into place by an annular fitting between the dressing and the connector, the handle can be removed and discarded, leaving only the dressing, and catheter connector in place. Various designs are disclosed to implement the releasable mounting handle that allow over-the catheter hub or hub connector mounting of the circumferential dressing. The handle release mechanism can including but is not restricted to: a groove, a peel-away strip, a break-away tab, slit, etc. The catheter connector preferably has a needle-free connector port at its proximal end for connection to IV lines or other infusion devices.

BRIEF DESCRIPTION OF THE DRAWINGS

The invention will be more fully understood from the following detailed description taken in conjunction with the accompanying drawings, in which:

FIGS. 22A-22F are different views of another embodiment of catheter extension and integrated dressing assembly according to the present invention;

FIG. 23A is a flush assembly according to the present invention;

FIG. 23B is another embodiment of a flush assembly according to the present invention;

FIGS. 24A-24G are different views of yet another embodiment of a catheter extension and integrated dressing assembly according to the invention;

FIG. 24A shows the catheter extension and dressing aligned with an conventional IV needle or catheter prior to connection;

FIG. 24B schematically shows an initial step of joining the catheter interconnector and its mounting handle to the IV needle;

FIG. 24C schematically shows the step of applying a dressing according to the invention;

FIG. 24D is a detailed view of a collar element for use in the catheter extension and integrated dressing assembly of FIGS. 24A-24G;

FIG. 24E is another detailed view of the collar element of FIG. 24D, rotated such that the collar groove is aligned with the groove of the mounting handle;

FIG. 24F is a schematic illustration of the catheter extension and dressing assembly with the mounting handle and collar element removed detached from the catheter extension and dressing;

FIG. 24G is another illustration of the catheter extension and dressing assembly of FIGS. 24A-24F, showing each of the elements.

DETAILED DESCRIPTION OF THE INVENTION

Figure 1:
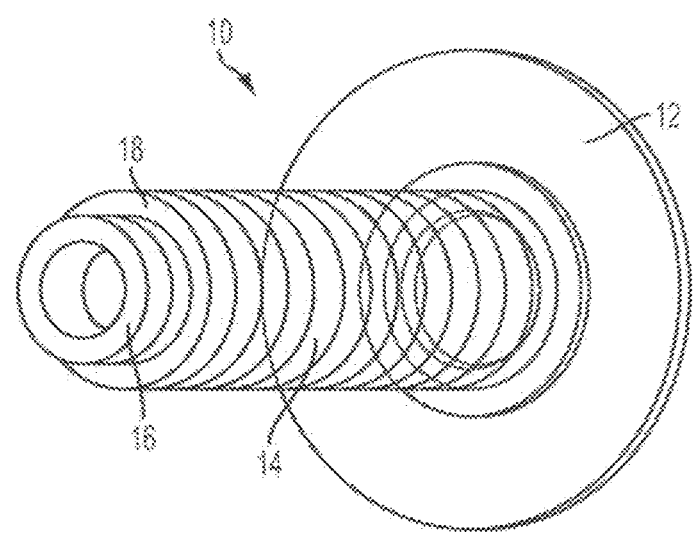
FIG. 1 is a perspective view of one embodiment of a catheter dressing according to the invention.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A person skilled in the art will appreciate that, while methods and devices are described herein in connection with catheters implantable in humans, the methods and devices can also be used in any instance in which a seal is desired around an elongate device implanted into or otherwise extending from a plant, an animal, and/or any non-living machine, structure, or system.

In general, devices and methods are provided for circumferentially sealing a catheter insertion site with improved sterility. The devices and methods can also involve securing a catheter in various ways. For example, a dressing can be provided to restrict longitudinal movement (e.g. inward or outward migration) of a catheter relative to a patient while at the same time permitting free non-longitudinal movement of the catheter (e.g., up, down, left, right, lateral, and/or rotational), all without disrupting or disturbing the sterile circumferential seal. In other words, once sealed, the catheter can be restricted or prevented by the dressing from being further withdrawn from, or inserted into, the patient but can remain otherwise freely movable. Alternatively, the dressing can be configured to completely secure the catheter such that all movement of the catheter relative to the patient is restricted. A catheter dressing is provided in one embodiment that includes an adhesive plate configured for attachment to the skin of a patient and a dressing body or sheath that extends proximally from the adhesive plate. For example, dressing body can be a flexible sheath is capable of longitudinal extension from a compressed to an extended state and configured in its extended state to surround an external segment of a catheter implanted in the patient and circumferentially seal thereto at a distance from the adhesive plate. When installed, the catheter dressing can define a sterile sealed chamber around the catheter insertion site. The catheter dressing can restrict longitudinal movement of the catheter relative to the patient (e.g., prevent such movement altogether or restrict such movement to a range commensurate with the range over which the sheath can be compressed and extended). At the same time, the catheter can be moved left, right, up, down, etc. relevant to the patient without disrupting the sterile sealed chamber.

Figure 2A:
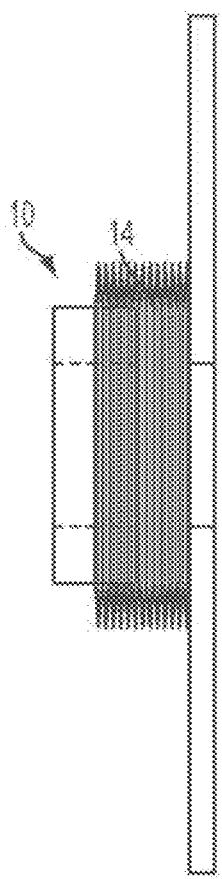
FIG. 2A is a plan view of the catheter dressing of FIG. 1 in a compressed state.
Figure 2B:
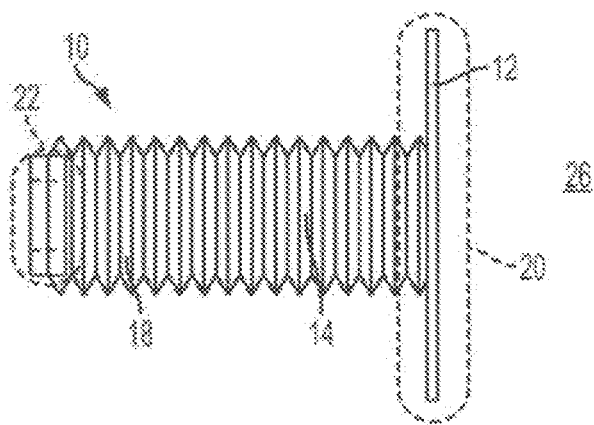
FIG. 2B is a plan view of the catheter dressing of FIG. 1 in an extended state.

FIG. 1 illustrates one exemplary embodiment of a catheter dressing 10. As shown, the dressing 10 is generally in the form of a plate 12 configured to be attached to the skin of a patient around a catheter insertion site and a dressing body 14 extending proximally from the plate 12. As used herein "proximal" refers to a direction or location away from a patient and "distal" refers to a direction or location towards or into the patient. A sealing element 16 can be provided at the proximal end 18 of the dressing body or sheath 14 for sealing to a catheter inserted through the sheath 14. As used herein, "catheter" refers not only to a catheter body itself, but also includes, without limitation, peripheral IV catheters, central line catheters, intra-arterial catheters, intra-arterial access sheaths, catheter hubs, catheter connection and/or coupling devices, catheters having a specially modified connection point, and/or any other associated structures or devices. The plate 12 is configured to provide a sterile, 360 degree seal with a surface to which it is attached, for example a skin surface of a patient. Thus, the plate 12 can provide a seal that completely surrounds a catheter insertion site. As shown in FIGS. 2A and 2B, the dressing body/sheath 14 is capable of longitudinal extension from a compressed state (FIG. 2A) to an extended state (FIG. 2B). In either state, and anywhere in between, the dressing 10 provides at least two distinct seal regions 20, 22. A first seal region 20 is formed between the plate 12 and a patient 26. A second seal region 22 exists at the proximal end 18 of the dressing body/sheath 14, where the dressing body/sheath can be sealed to a catheter. Thus, the dressing body/sheath 14 is extendable proximally from the plate 12 and is configured to surround and circumferentially seal to a catheter, thereby defining a sealed, sterile chamber around the catheter and the catheter insertion site.

As used herein, the terms "circumferential seal," "circumferentially sealed", and any related terms or variations thereof should not be construed as being limited only to a seal formed around a round or circular object. Rather, these terms refer also, without limitation, to a seal formed all the way around or substantially all the way around the perimeter of any object, regardless of shape.

Figure 3:
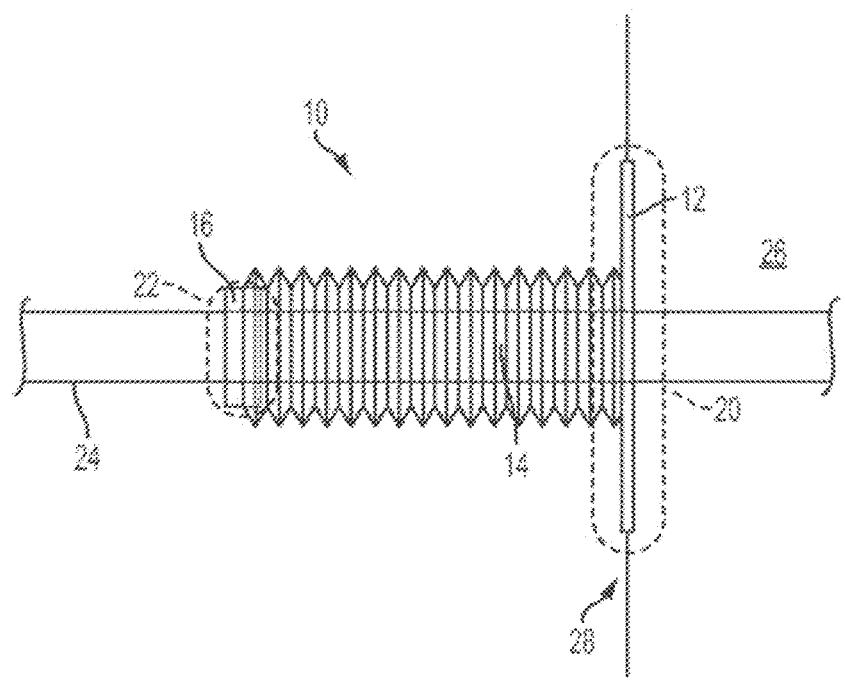
FIG. 3 is a plan view of a catheter implanted in a patient and sealed using the catheter dressing of FIG. 1.

As shown in FIG. 3, a catheter 24 can be inserted into a patient 26 through a skin surface 28. The dressing 10 can be installed over the catheter 24 such that the two are substantially coaxial. The plate 12 can be adhered to the skin surface 28, thereby forming a first seal region 20 that surrounds the catheter insertion site. The dressing body/sheath 14 can be extended a distance longitudinally along the catheter 24 to a second seal region 22, where the sealing element 16 can create a sterile seal between the dressing body/sheath 14 and the catheter 24. Once installed, the dressing 10 is effective to define a sealed, sterile region around the catheter insertion site and at least a portion of the catheter.

Figure 4A:
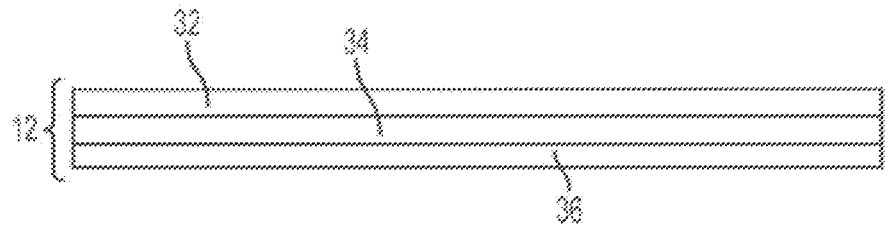
FIG. 4A is a cross-sectional profile view of one embodiment of an attachment plate according to the invention.

The plate 12 can have a variety of configurations. In one embodiment, as shown in FIG. 4A, the plate includes a flexible structural layer 32, an adhesive layer 34, and a peel-away backing layer 36. The backing layer 36 covers and protects the adhesive layer 34 until just before the dressing 10 is to be installed. During installation, the backing layer 36 can be removed, thereby exposing the adhesive layer 34 for attachment to the patient's skin. Any of a variety of adhesives known in the art can be used for attaching the plate 12 to the patient's skin and the adhesive can be chosen based on a variety of factors, including for example the quality, sterility, and durability of the seal created, the biocompatibility of the adhesive with human skin or with a particular skin type, and/or cost.

Although illustrated as being an adhesive plate, the plate 12 can be attached to the patient in a variety of ways. For example, the plate can include hooks, tabs, and/or apertures through which a suture or other tie-down mechanism can be received, or a suture can be threaded directly through the plate material. The plate can also be attached using an adhesive tape such that the tape partially overlaps the proximal surface of the plate 12 and partially overlaps the patient's skin. Various combinations of the attachment techniques described herein can also be employed. In addition, as discussed in further detail below, a secondary plate seal support device can be employed to augment the plate-skin seal.

The plate 12 can be made from a variety of materials known in the art such as various semi-rigid/flexible materials, including polyurethanes such as Pellethane (available from The Dow Chemical Company of Midland, Mich., USA), thermoplastic elastomers such as Santoprene (available from ExxonMobil Chemical of Houston, Tex., USA), polyisoprene elastomers, medium to high durometer silicone elastomers, and/or any combination thereof. The plate can also be formed of various polymers, including polycarbonates and polyetheretherketone (PEEK), metals such as titanium or stainless steel, composites such as carbon-fiber reinforced PEEK, various ceramic materials, and/or any combination thereof. The plate can also be formed from any other suitable fabrics, foams, plastics, and/or metals known in the art.

Figure 4B:
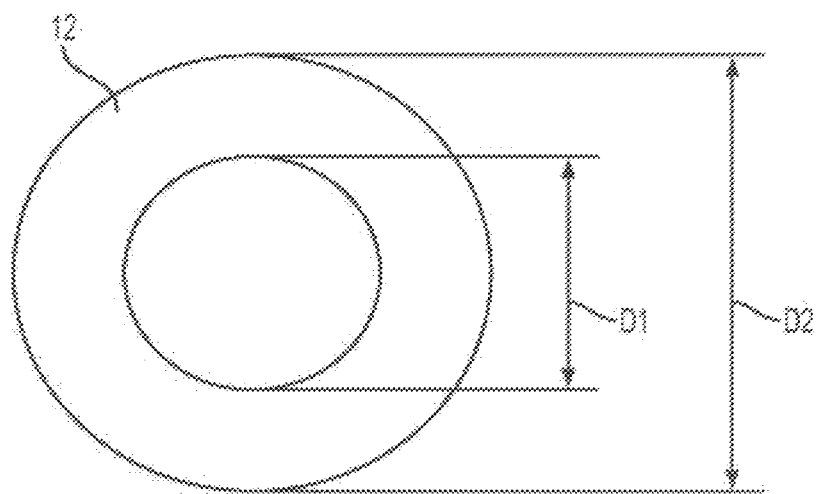
FIG. 4B is a plan view of the attachment plate of FIG. 4A.

As illustrated in FIG. 4B, the plate is generally in the form of a thin annular ring having an inner diameter D1 and an outer diameter D2. Although the illustrated embodiment is of a generally circular shape, the plate 12 can also be constructed in virtually any other shape, such as rectangular or elliptical. In general, the plate 12 is sized in accordance with the catheter to which it will be applied. Specifically, the inner diameter D1 of the plate 12 can be sized such that it is slightly larger than the diameter of the catheter. In the case of an adhesive attachment means, the outside diameter D2 of the plate 12 can be chosen based in part on the strength of the adhesive used to ensure that an adequate surface area of the plate 12 is adhered to the patient to maintain a strong and stable seal. In one exemplary embodiment, the plate can be in the form of an annular ring having an inner diameter of approximately 0.5 mm to approximately 20 mm and an outer diameter of approximately 2 mm to approximately 100 mm.

The dressing body/sheath 14 can be formed integrally with the plate 12 or it can be attached thereto using a variety of techniques, so long as a sterile seal exists therebetween. For example, the distal end of the dressing body/sheath 14 can be sandwiched between multiple layers of the plate 12, or it can be attached to the plate 12 using an adhesive. A variety of other methods known in the art can also be employed, such as sonic welding, frictional engagement, etc.

Figure 5A:
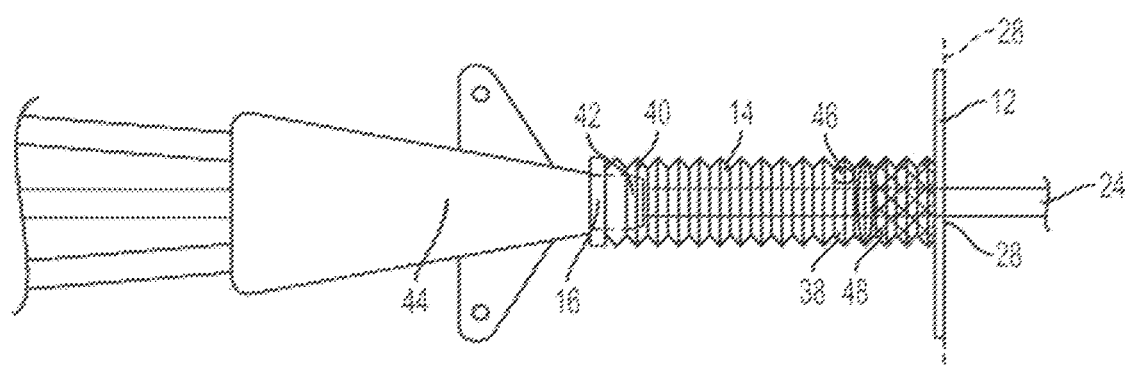
FIG. 5A is a plan view of one embodiment of a catheter dressing according to the invention sealed to a catheter hub.

As shown in FIG. 5A, the dressing body/sheath 14 is generally in the form of an elongate flexible tube. While the illustrated dressing body/sheath 14 is flexible, the dressing body/sheath 14 and/or dressing 10 can also be rigid or semi-rigid, which can advantageously permit longitudinal or other movement of the catheter relative to the patient to be further restricted by the dressing. The surface of the sheath can be pleated or folded in an accordion-like fashion such that the sheath 14 is extendible from a compressed state to an expanded state (see FIGS. 2A-2B). Alternatively, or in addition, the sheath can be formed from a stretchable material to facilitate longitudinal extension. Exemplary materials from which the sheath can be formed include a clear flexible plastic, similar to that used for other medical-surgical grade materials and devices. Many options for this plastic material are available and that chosen for the sheath can have a combination of optimal attributes such as flexibility, strength, durability, breathability, microbial resistance, etc. Other exemplary sheath materials include silicone, polyisoprene, other elastomers or rubbers, and/or any combination thereof. Any other suitable material known in the art can also be used. The terms "dressing body" and "sheath" are used interchangeably throughout this description.

The distal end 38 of the sheath 14 is configured to sealably attach to the plate 12, as described above. The proximal end 40 of the sheath 14 is configured to seal around a catheter and can optionally include a sealing element 16. In the illustrated embodiment, the sealing element 16 is in the form of a flexible gasket ring. The sheath 14 can be molded around the sealing element 16, can be bonded thereto using an adhesive, or can be attached thereto using any other suitable method known in the art. The sealing element 16 and the sheath 14 can sealably mate to a catheter. In the illustrated embodiment, the sheath 14 is shown advanced proximally along a catheter 24 and over a portion of the nose 42 of a 3-into-1 catheter hub 44. As shown, the nose 42 of the catheter hub 44 has a generally conical tapered surface. The sealing element 16 is stretched over the nose 42 such that the resilient properties of the sealing element 16 cause it to exert a radially inward force against the nose 42. When advanced far enough along the nose 42, this force can create a sealing engagement between the hub 44 and the sheath 14 and/or the sealing element 16. Although a sealing element 16 in the form of a stretchable gasket ring is illustrated, such structure is not necessarily required. For example, the sheath 14 itself can have flexible and resilient properties that would facilitate sealing engagement with a catheter. Furthermore, a seal between the sheath 14 and a catheter can be effected in a variety of other ways, including for example adhesive bonding, clamping, balloon pressure inflation, and/or magnetic coupling.

The catheter dressing 10 can also include an absorbent element 48 disposed within the sheath 14. In one embodiment the absorbent element 48 can be a strip of sterile gauze material positioned adjacent to the skin surface 28 of the patient. In such embodiments, the absorbent element 48 can absorb any moisture, condensation, or fluid seepage emanating from the catheter insertion site, from the patient's skin, or otherwise present within the sealed catheter dressing 10. An antimicrobial-containing or antibiotic-containing element can also be disposed within the sheath 14 and can optionally be configured to release one or more cleansing/sterilizing agents over time. Alternatively, or in addition, the sheath 14 or dressing 10 itself can be formed from an antibiotic or antimicrobial impregnated material and can release said antibiotic or antimicrobial over time.

The sheath can also optionally include an access portal 46 for accessing and manipulating the internal volume and contents of the sheath 14. For example, the access portal 46 can permit infusion of cleansing, sanitizing, and/or antimicrobial type solutions, to clean or replace the absorbent element 48, or to permit the infusion of sterilizing gas or use of another sterilizing material. When appropriate, the access portal 46 can also be used to expose the sealed volume of the dressing and the catheter insertion site to ultraviolet or other sanitizing radiation, or to remove a sample or specimen from the dressing 10 for testing. The access portal 46 can also be used to alter various conditions within the sealed dressing 10, such as pH, temperature, humidity, sterility, etc.

In one embodiment, at least a portion of the sheath 14 can be transparent to allow for visualization and monitoring of the internal condition and contents of the sealed volume and the catheter insertion site. For example, the entire sheath 14 can be formed of a transparent material as illustrated in FIG. 5A, or the sheath can include one or more transparent windows at various points along an outer surface thereof.

Figure 5B:
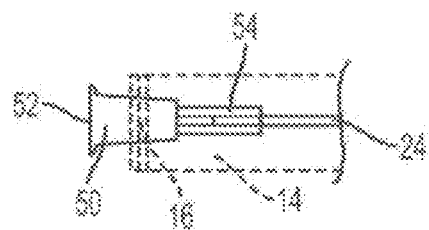
FIG. 5B is a plan view of another catheter hub showing a catheter dressing according to the invention in phantom.
Figure 5C:
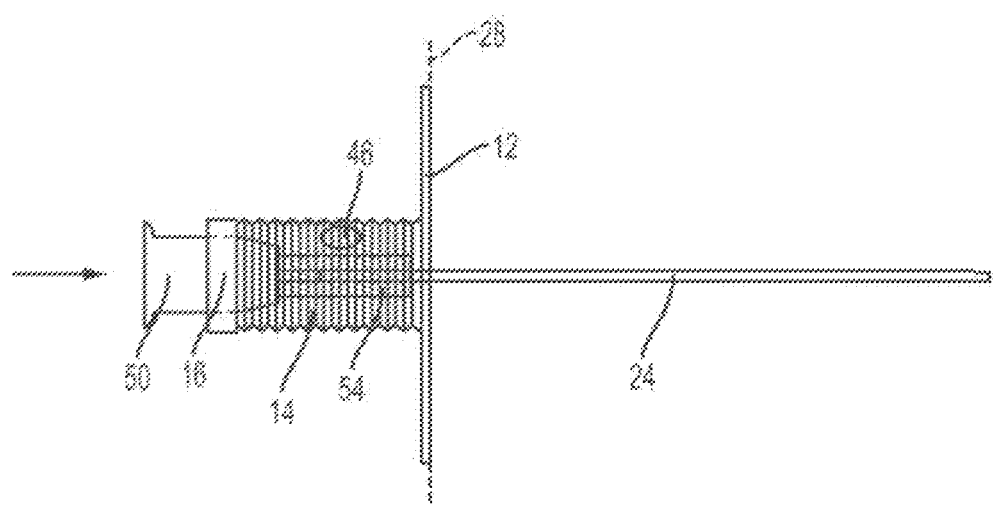
FIG. 5C is a plan view of the catheter dressing and catheter hub of FIG. 5B.

In addition to central line catheter hubs like the one illustrated in FIG. 5A, the sheath 14 and/or the sealing element 16 can also be effective to circumferentially seal around an external surface of various other catheter components. For example, FIGS. 5B and 5C illustrate a standard catheter hub 50. As shown, the hub 50 includes a first, proximal end 52 for coupling to a fluid conveying device such as a syringe or IV line. The hub further includes a second, distal end 54 that is in fluid communication with the proximal end 52 and that is configured to couple to an implantable catheter 24. Much like the central line catheter hub 44 discussed above, the standard catheter hub 50 can be circumferentially sealed by advancing the sheath 14 and/or sealing element 16 proximally along a tapered outer surface of the hub 50.

Figure 5D:
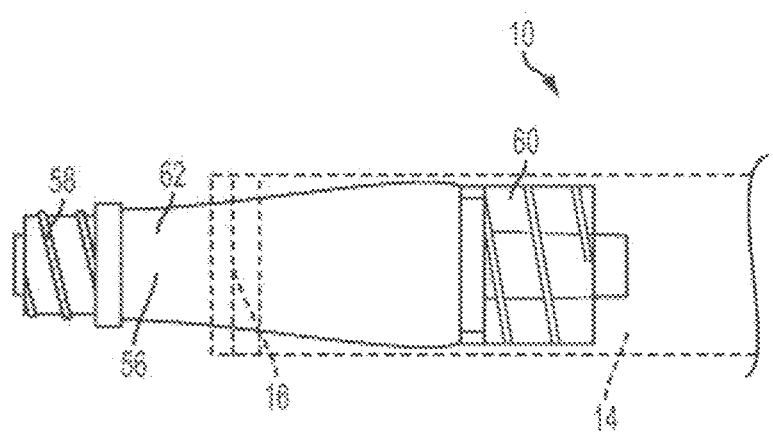
FIG. 5D is a plan view of a MicroCLAVE-type connector showing a catheter dressing according to the invention in phantom.
Figure 5E:
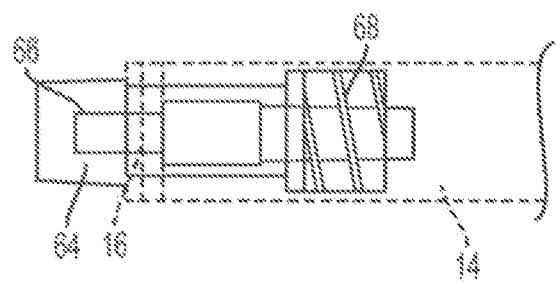
FIG. 5E is a plan view of a Luer-type connector likewise showing a catheter dressing according to the invention in phantom.

As shown in FIGS. 5D-5E, the catheter dressing 10 can be part of a catheter dressing assembly that can further include an intermediate coupling member. In general, the coupling member has a distal end that is in fluid communication with an implantable catheter. The proximal end of the coupling member can include a valve such as a Luer-type connector, a MicroCLAVE-type connector, a threaded fitting, and/or a friction fitting. The valve can also be a blunt injection site or can be configured to couple to a variety of fluid conveying devices, such as syringes, IV lines, catheter extensions, and the like. FIG. 5D illustrates one embodiment of a coupling member in the form of a MicroCLAVE-type connector 56. The connector 56 includes fittings 58, 60 at either end configured to couple the connector to various fluid conveying devices known in the art, including for example implantable catheters. The main body of the connector 56 includes a tapered outer surface 62 over which the sheath 14 and/or sealing element 16 can be advanced to form a sterile seal. FIG. 5E shows another embodiment of a coupling member in the form of a Luer-type connector 64. The Luer-type connector includes fittings 66, 68 at either end configured to couple the connector 64 to various fluid conveying devices known in the art, including for example implantable catheters. The main body of the connector 64 includes an outer surface over which the sheath 14 and/or sealing element 16 can be advanced to form a sterile seal. While MicroCLAVE-type and Luer-type connectors are specifically illustrated and described herein, a person having ordinary skill in the art will appreciate that any suitable fluid conveying structure can be used as a coupling member.

Figure 5F:
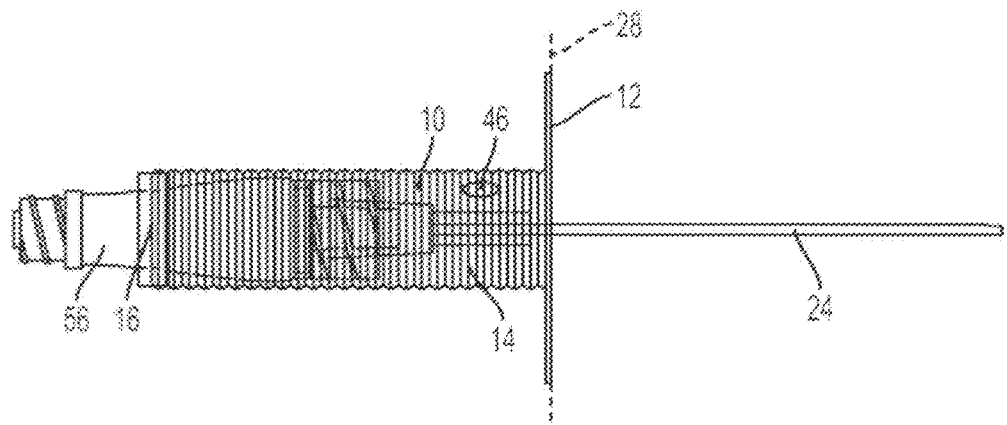
FIG. 5F is a plan view of the catheter dressing and connector of FIG. 5D.
Figure 5G:
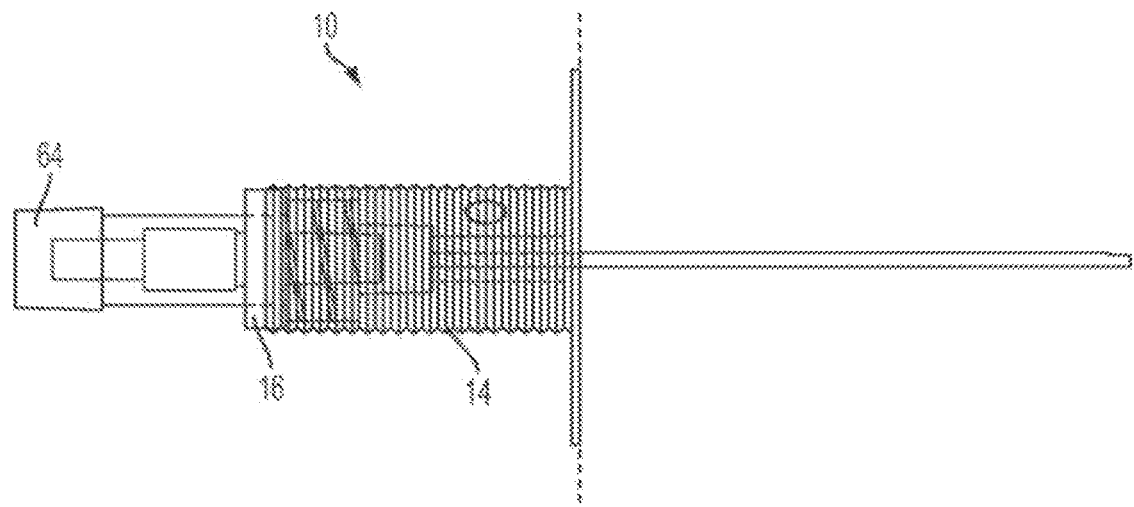
FIG. 5G is a plan view of the catheter dressing and connector of FIG. 5E.
Figure 6A:
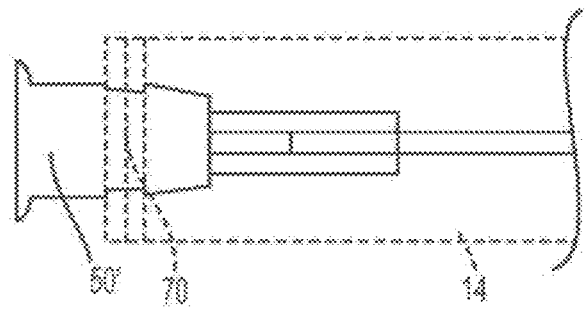
FIG. 6A is a partial cross-sectional plan view of a catheter dressing sealed to a catheter hub having an integral attachment mechanism according to the invention.
Figure 6B:
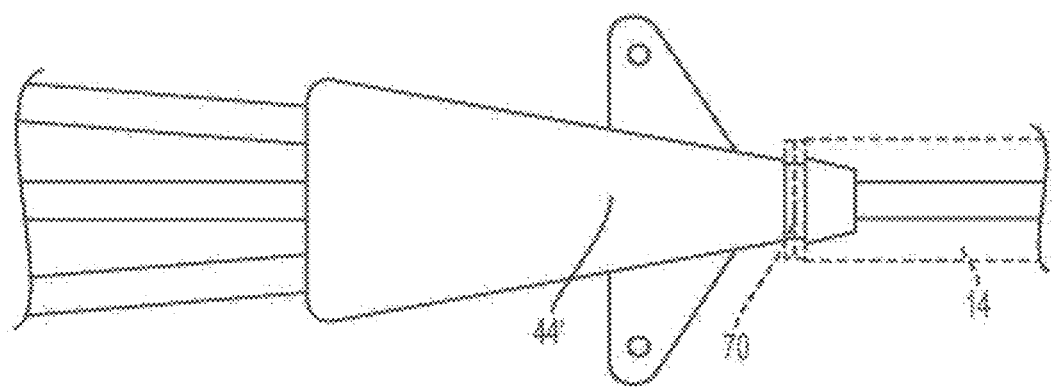
FIG. 6B is a partial cross-sectional plan view of a catheter dressing sealed to another catheter hub likewise having an integral attachment mechanism according to the invention.
Figure 6C:
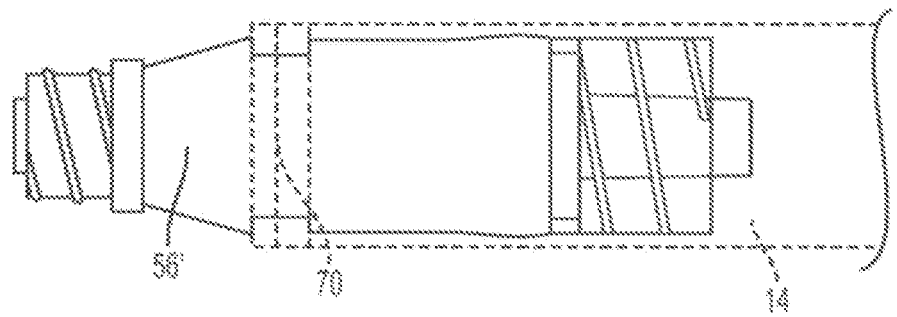
FIG. 6C is a phantom view of a catheter dressing sealed to a MicroCLAVE-type connector having an integral attachment mechanism according to the invention.
Figure 6D:
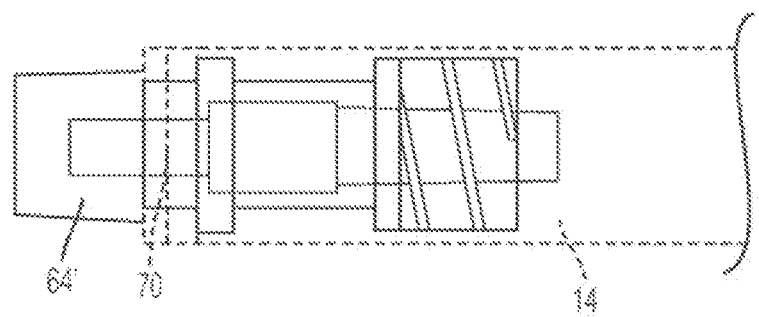
FIG. 6D is a phantom view of a catheter dressing sealed to a Luer-type connector having an integral attachment mechanism according to the invention.

FIG. 5F illustrates a catheter dressing 10 sealed around an implanted catheter 24 that is coupled to a MicroCLAVE-type connector 56. As shown, an adhesive plate 12 circumferentially surrounds a catheter insertion site and is adhered to the skin 28 of a patient. A sheath 14 extends proximally from the adhesive plate 12 to the connector 56. A sealing element 16 at the proximal end of the sheath 14 is drawn distally against the tapered surface of the connector 56, resulting in a sterile seal between the sheath 14 and the connector 56. FIG. 5G shows a similar catheter dressing 10 sealed around a Luer-type connector 64. As shown, the sealing element 16 at the proximal end of the sheath 14 frictionally engages the central body of the connector 64, forming a sterile seal therewith.

The catheter dressing assembly can also include a variety of catheter components that are specifically tailored for receiving the sheath 14 and/or the sealing element 16 of the catheter dressing 10. By way of non-limiting example, catheter bodies, catheter hubs, MicroCLAVE-type connectors, Luer-type connectors, and/or any intermediate-type connector directly attached in luminal continuity with the catheter can all be modified to include an attachment mechanism to enhance the integrity and stability of the dressing seal. For example, as shown in FIGS. 6A-6D, a catheter hub 50', a catheter hub 44', a MicroCLAVE-type connector 56', and/or a Luer-type connector 64' can each be modified to include an annular groove 70 formed in an outer surface thereof configured to receive the sealing element 16 and/or a portion of the sheath 14 therein. As will be appreciated by a person having ordinary skill in the art, inclusion of such a groove can provide for a more durable and tighter seal between the catheter components 50', 44', 56', 64' and the sheath 14.

In order to achieve optimal patient comfort, optimal catheter stability, and minimal damage to internal patient vessels and structures, it can be desirable to orient the catheter such that it lies substantially flat against the patient's skin. In one embodiment, the dressing can be configured to secure the catheter in such a position, and to prevent inadvertent movement of the catheter relative to the patient. Alternatively, or in addition, securement devices can be provided that are configured to further secure the catheter and/or the catheter dressings and dressing assemblies described herein to the patient. In certain embodiments, the securement device can also provide additional strength and stability to the seal between the sheath and the catheter.

As shown in FIGS. 7A-7D, a securement device in the form of a clamp 72 can be used to anchor the catheter 24 and/or catheter dressing 10 to the patient 26. As particularly shown in FIG. 7D, the clamp 72 includes a planar base portion 78 and an upright clamping portion 88. The clamping portion 88 includes first and second levers 80, 82 and a ratchet and pawl mechanism 84, 86. Squeezing the first and second levers 80, 82 towards each other causes the inner diameter of the clamping portion 88 to decrease as the pawl 86 rides over one or more ratchet teeth 84. As the first and second levers 80, 82 are advanced toward one another, the ratchet and pawl mechanism 84, 86 is effective to prevent movement of the first and second levers 80, 82 away from each other and thus to prevent diametrical expansion of the upright clamping portion 88. When necessary to release or open the clamp, the first lever 80 can be actuated to disengage the pawl 86 from the ratchet teeth 84, thereby permitting the inner diameter of the clamping portion 88 to expand and ultimately open. To ensure optimal operation of the clamp 72, it can be formed from any flexible yet semi-rigid material known in the art.

Figure 7A:
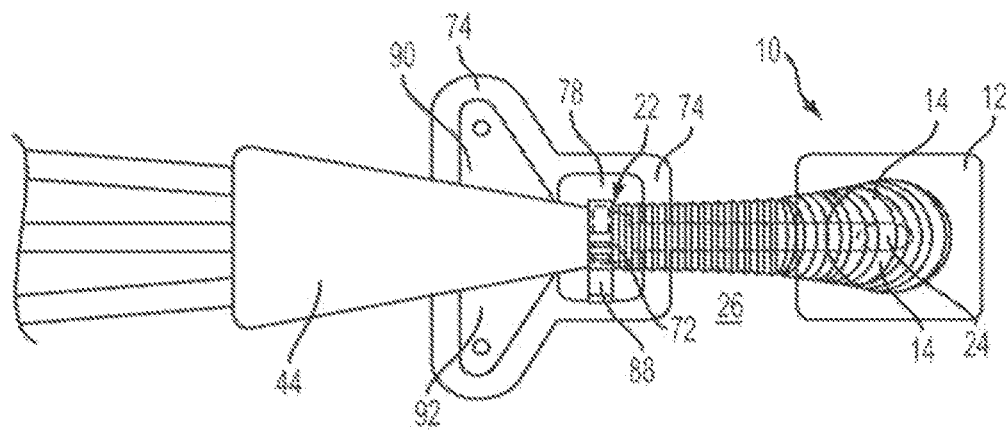
FIG. 7A is a top view of an implanted catheter dressed with a catheter dressing and a catheter hub secured to a patient with one embodiment of a securement device.
Figure 7B:
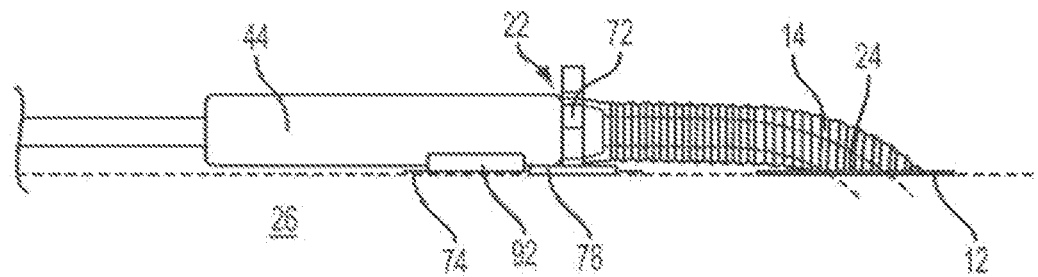
FIG. 7B is a side view of the implanted catheter and catheter dressing of FIG. 7A.
Figure 7C:
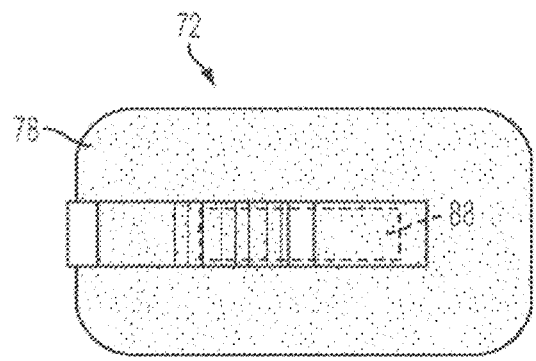
FIG. 7C is a plan view of the securement device of FIGS. 7A-7B.

Referring now to FIGS. 7A and 7B, an implanted catheter 24 is shown lying substantially flat against the patient 26 and dressed with a catheter dressing 10 as described herein. An adhesive pad 74, which can have a construction similar or identical to that of the adhesive plate 12, is used to attach the central line catheter hub 44 and the clamp 72 to the patient. The planar base portion 78 of the clamp and the lateral ears 90, 92 of the hub 44 can be affixed to the adhesive pad 74 using a variety of techniques known in the art. As shown, the clamp 72 can be positioned with respect to the hub 44 such that the upright clamping portion 88 is substantially aligned with the seal region 22 defined by the sheath 14, hub 44, and/or sealing element 16. Thus, squeezing the first and second levers 80, 82 of the clamp 72 towards each other and locking the levers 80, 82 using the ratchet and pawl mechanism 84, 86 is effective to apply a force radially inward against the seal region 22, resulting in a tighter and more secure seal.

Figure 7D:
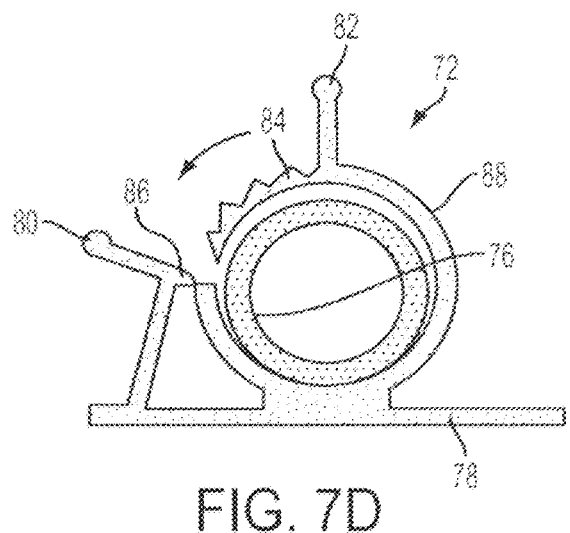
FIG. 7D is a profile view of the securement device of FIGS. 7A-7C.

As shown particularly in FIG. 7D, the clamp 72 can further include a inner gasket ring 76 configured to prevent abrasion of the sheath 14 and/or sealing element 16 by the clamp 72. The gasket ring 76 can also ensure that the radial force applied by the clamp 72 is substantially uniform about the circumference of the seal region 22.

While the catheter dressing 10, clamp 72, and/or catheter 24 are generally described herein as being attached directly to the skin of a patient, other indirect attachment means are also possible. For example, any of these structures could instead be attached first to a wrap, pad, bandage, or the like which can then in turn be attached to the patient. In addition, the clamp 72 can optionally be free floating (e.g., can be provided without the base portion 78) and can be applied to the dressing after it is installed around a catheter, as discussed in greater detail below.

Figure 8A:
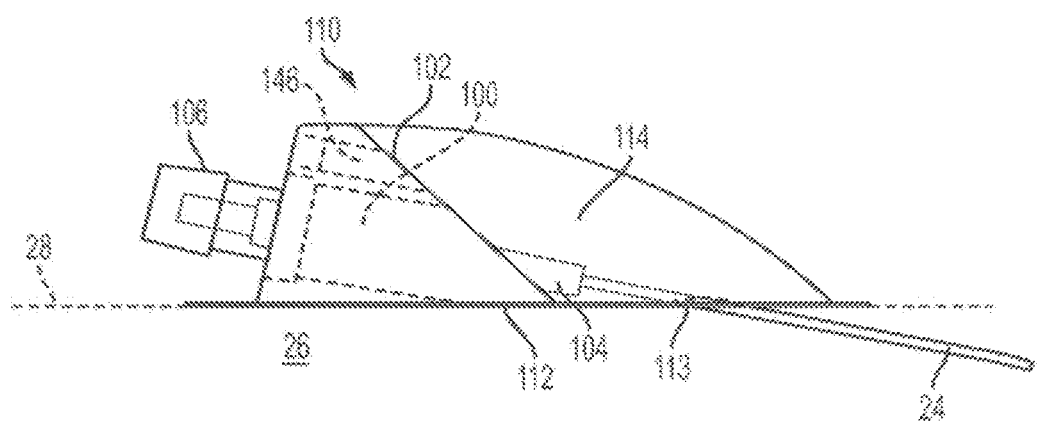
FIG. 8A is a partial cross-sectional profile view of a catheter implanted in a patient and dressed with another embodiment of a dressing device according to the invention.
Figure 8B:
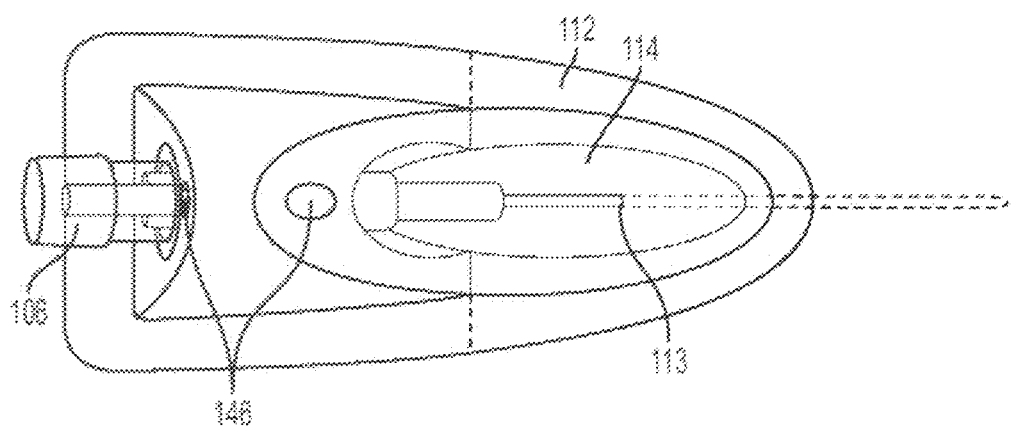
FIG. 8B is a partial cross-sectional plan view of the catheter and dressing device of FIG. 8A.
Figure 8C:
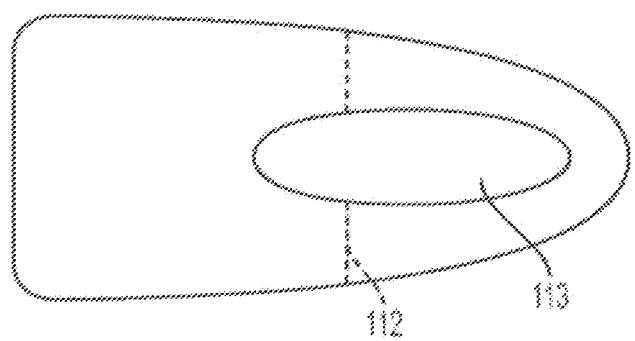
FIG. 8C is a plan view of one embodiment of a folding plate for use in a catheter dressing according to the invention.

In another exemplary embodiment, the plate, sheath, coupling member, and clamp can be provided as a single unitary dressing device 110. As illustrated in FIG. 8A, the device 110 generally includes a folding adhesive plate 112, a coupling member or coupling body 100, and a flexible sheath 114. The folding adhesive plate 112 is configured to attach to the skin 28 of a patient 26 and includes an aperture 113 formed therein for receiving an implantable catheter 24 therethrough. The coupling body 100 can be fixedly attached to the adhesive plate 112 such that the flexible sheath 114 can extend from a ramped surface 102 of the coupling body 100 to a proximal surface of the folding plate 112 to form a sealed volume around the aperture 113. Thus, by placing the folding plate 112 such that the aperture 113 surrounds a catheter insertion site, a sterile sealed volume is created around the site.

The coupling body 100 can include an access portal 146 for accessing the sealed volume of the device. The coupling body 100 can also include a first fitting 104 disposed within the sealed volume and configured to couple to an implanted catheter 24. A second fitting 106 can also be provided to facilitate insertion or removal of fluids from the implanted catheter 24.

Figure 8D:
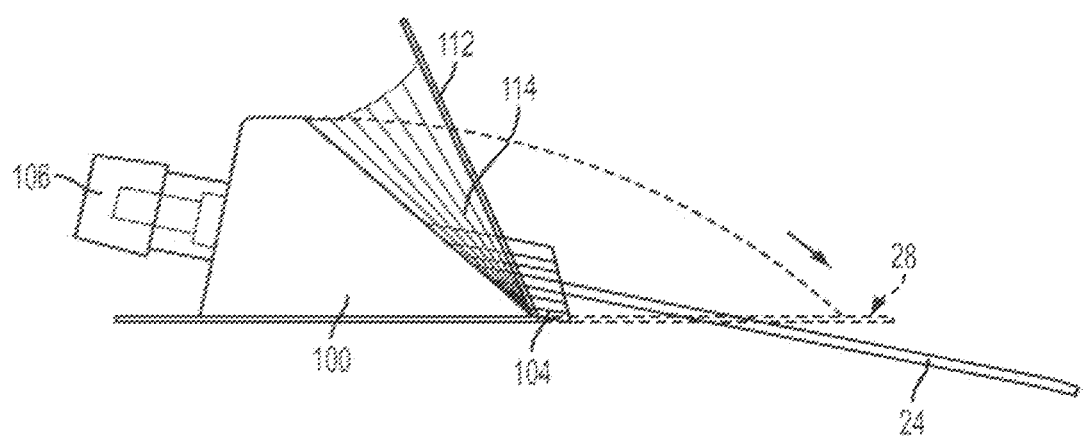
FIG. 8D is a partial cross-sectional profile view of one embodiment of a dressing device that includes the folding plate of FIG. 8C.

In use, the dressing device 110 is effective to create a circumferential seal around a catheter insertion site and an implanted catheter 24 and to prevent movement (e.g., longitudinal, lateral, and/or rotational) of the implanted catheter 24. As shown in FIG. 8D, the device can be placed on a skin surface 28 adjacent to a catheter insertion side with the adhesive plate 112 in a folded position. Using appropriate sterile procedures, the external portion of the implanted catheter 24 can be coupled to the first fitting 104 of the coupling body 100. The adhesive plate can then be lowered to an unfolded position in which it lies substantially flat against the patient's skin surface 28 and is adhered thereto, thereby surrounding the catheter insertion site and enclosing it within the aperture 113. When installed, the dressing device 110 defines a sealed volume around the implanted catheter 24 and the catheter insertion site beneath the sheath 114. The sealed volume is accessible via the access port 146 and the catheter is accessible via the second fitting 106 of the coupling body 100.

Figure 9A:
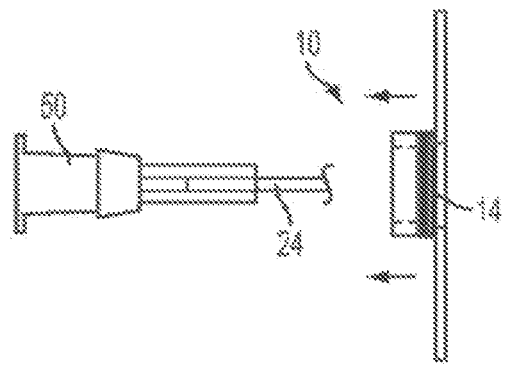
FIG. 9A is a plan view of a catheter, a catheter hub, and one embodiment of a catheter dressing according to the invention.
Figure 9B:
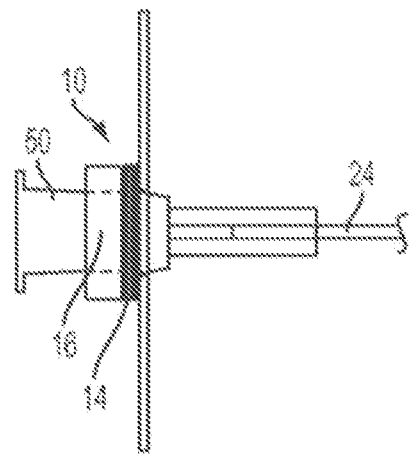
FIG. 9B is a plan view of the catheter dressing of FIG. 9A sealed to the catheter hub of FIG. 9A.
Figure 9C:
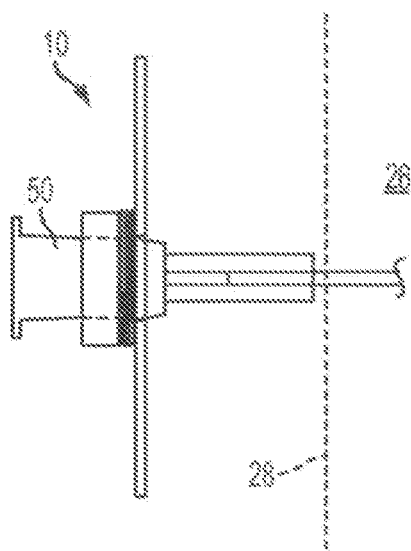
FIG. 9C is a plan view of the catheter, catheter dressing, and catheter hub of FIGS. 9A-9B after the catheter has been partially implanted in a patient.
Figure 9D:
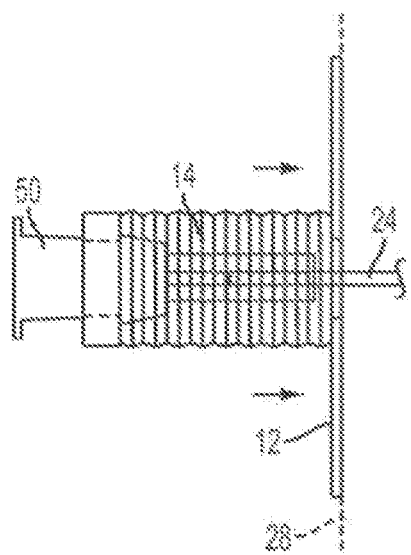
FIG. 9D is a plan view of the catheter dressing of FIGS. 9A-9C sealed to a patient's skin.
Figure 10A:
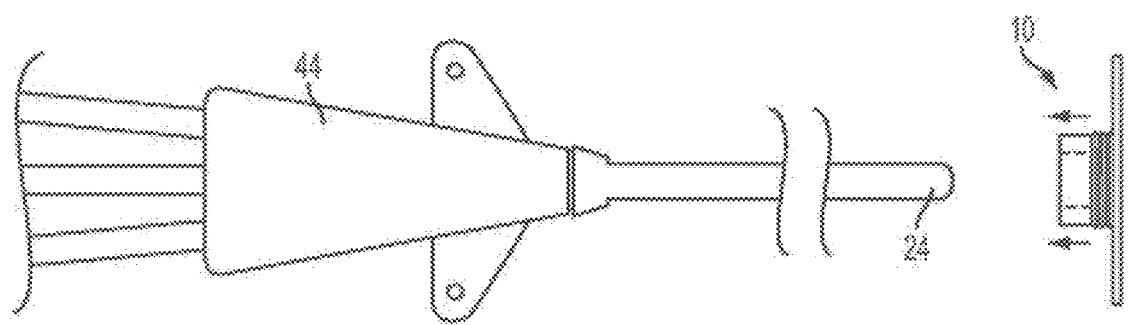
FIG. 10A is a plan view of a catheter, a catheter hub, and another embodiment of a catheter dressing according to the invention.
Figure 10B:
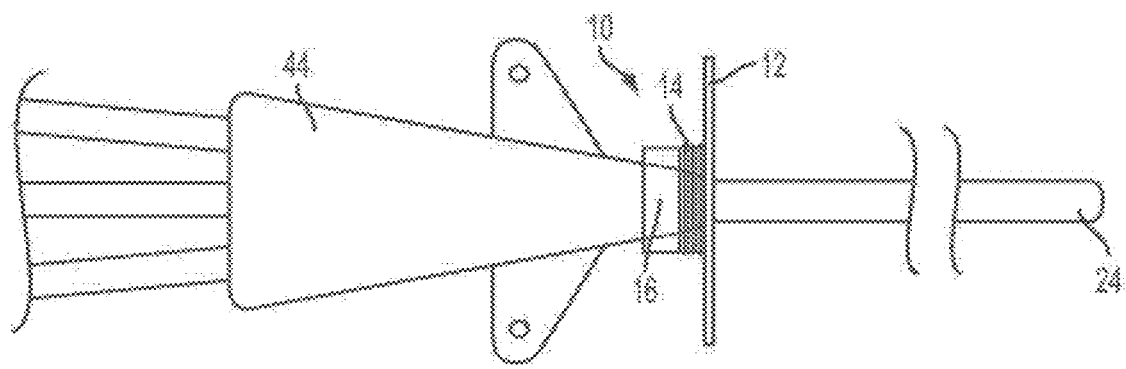
FIG. 10B is a plan view of the catheter dressing of FIG. 10A sealed to the catheter hub of FIG. 10A.
Figure 10C:
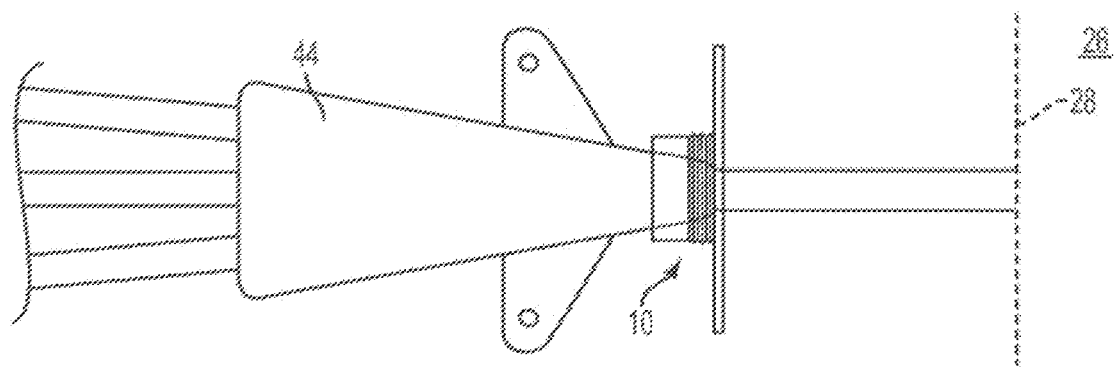
FIG. 10C is a plan view of the catheter, catheter dressing, and catheter hub of FIGS. 10A-10B after the catheter has been partially implanted in a patient.
Figure 10D:
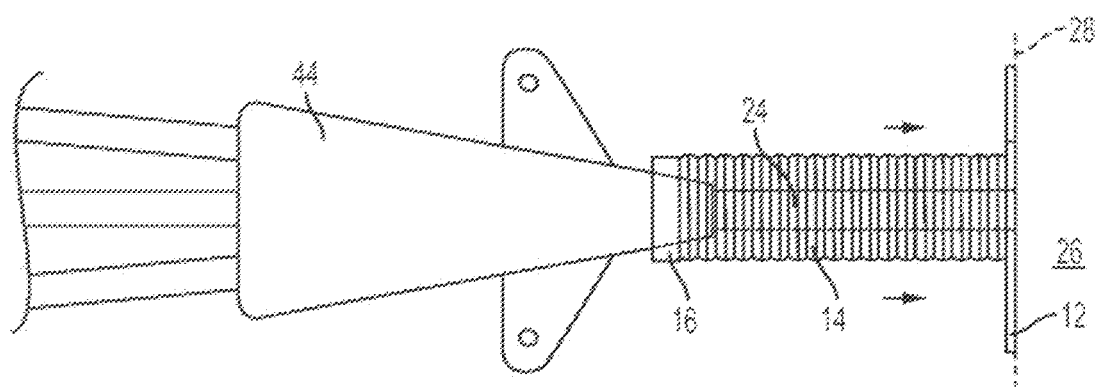
FIG. 10D is a plan view of the catheter dressing of FIGS. 10A-10C sealed to a patient's skin.

Various methods for circumferentially sealing a catheter insertion site are also provided herein, for example by using the catheter dressings and systems described above. FIGS. 9A-9D illustrate one exemplary method for sealing an implantable catheter 24 that is coupled to a catheter hub 50. As shown in FIG. 9A, a catheter dressing 10 is configured with the flexible sheath 14 in a compressed state and a catheter 24 is inserted therethrough. The dressing 10 is advanced proximally along the catheter 24 and the catheter hub 50 until the sealing element 16 of the sheath 14 forms a satisfactorily tight seal with the hub 50, as shown in FIG. 9B. As shown in FIG. 9C, the catheter can then be inserted into a patient 26 at a catheter insertion site. The sheath 14 can then be longitudinally extended along the implanted catheter 24 such that the adhesive plate 12 can be attached to the patient's skin surface 28, thereby forming a sterile circumferential seal around the catheter 24, a portion of the catheter hub 50, and the catheter insertion site.

FIGS. 10A-10D illustrate a similar method wherein a central line catheter hub 44 and an associated catheter insertion site are circumferentially sealed using a catheter dressing 10. As shown, a catheter dressing 10 is advanced proximally over a catheter 24 and the catheter hub 44 until the sealing element 16 of the dressing 10 is stretched sufficiently over the hub 44 to create a sterile seal. The catheter 24 can be partially inserted into a patient 26 and the sheath 14 can be longitudinally extended to a state in which the adhesive plate 12 can be attached and sealed to a skin surface 28 of the patient 26.

Figure 11A:
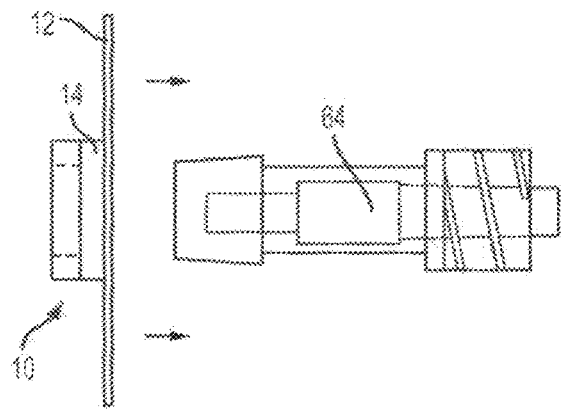
FIG. 11A is a plan view of a coupling member and yet another embodiment of a catheter dressing according to the invention.
Figure 11B:
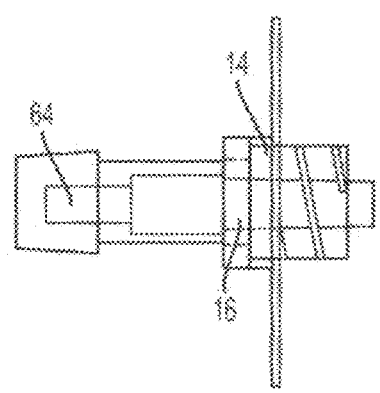
FIG. 11B is a plan view of the catheter dressing of FIG. 11A sealed to the coupling member of FIG. 11A.
Figure 11C:
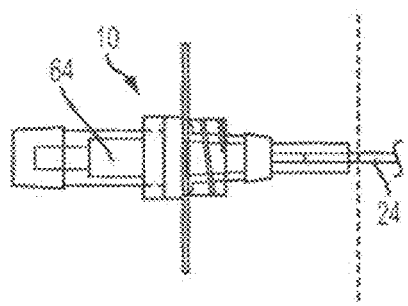
FIG. 11C is a plan view of a catheter coupled to the coupling member of FIGS. 11A-11B and partially implanted in a patient.
Figure 11D:
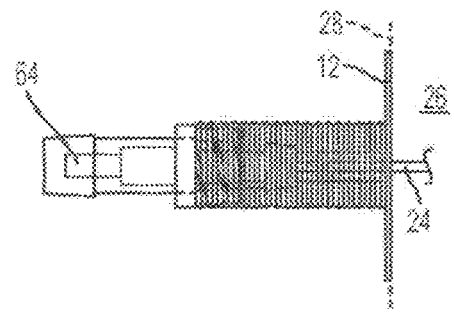
FIG. 11D is a plan view of the catheter dressing of FIGS. 11A-11C sealed to a patient's skin.

FIGS. 11A-11D illustrate an exemplary method for sealing an implanted catheter 24 using a catheter dressing 10 and an intermediate coupling member. As shown in FIG. 11A, one example of an intermediate coupling member—a Luer-type connector 64—can be passed through the sheath 14 and adhesive plate 12 of a catheter dressing 10 while the sheath 14 is in a compressed state, thereby sealing the sheath 14 and/or the sealing element 16 circumferentially around the body of the Luer-type connector 64, as shown in FIG. 11B. The connector 64 can then be coupled to the proximal end of a catheter 24, either before or after the catheter is inserted into a patient, as illustrated in FIG. 11C. The sheath 14 can then be longitudinally extended along the connector 64 and catheter 24 to an extended state in which the adhesive plate 12 can be attached to the skin surface 28 of the patient 26, as shown for example in FIG. 11D. In an alternative embodiment, the adhesive plate 12 can be omitted or formed integrally with the sheath 14 such that the sheath 14 itself is directly attachable to the patient.

After a catheter insertion site is sealed using the methods or devices disclosed herein, it can be desirable to remove and/or replace the catheter dressing. Accordingly, dressings and related methods are provided that include a mechanism for removing and/or replacing the dressing.

Figure 12:
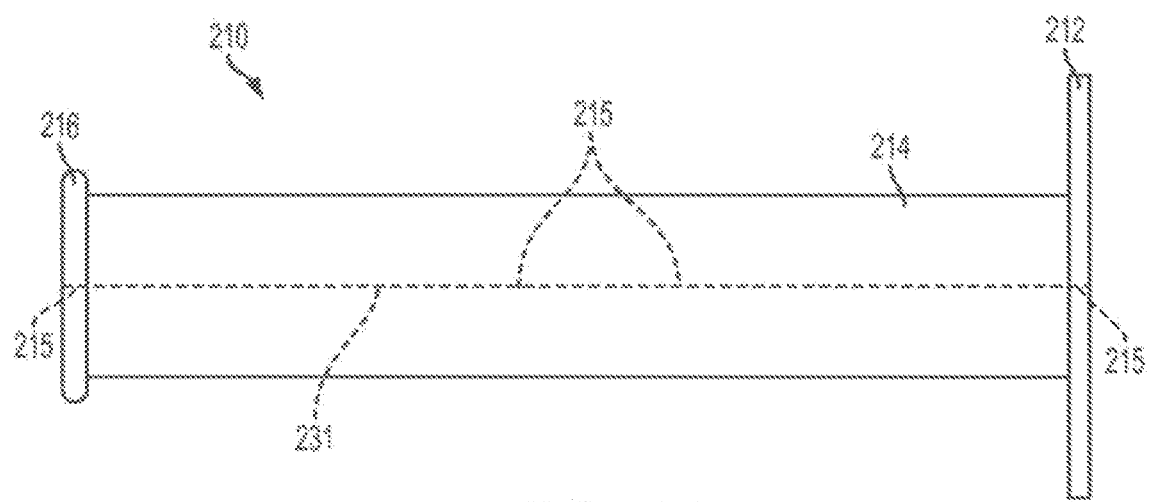
FIG. 12 is a plan view of another embodiment of a catheter dressing according to the invention capable of cleavage for removing the dressing from an installed catheter.

FIG. 12 illustrates one embodiment of a catheter dressing 210 that can be removed from an inserted catheter without requiring the catheter itself to be removed from the patient. As shown, the dressing 210 includes an adhesive plate 212, a sheath 214, and a sealing element 216, each of which have one or more pre-specified break-points 215. Together, the break points 215 define a longitudinal, linear seam 231 or path along which the dressing 210 can be separated when sufficient stress is applied. Thus, when it is desired to remove an installed dressing 210, the plate 212, the sheath 214, and the sealing element 216 can be separated along the seam 231 defined by the break points 215 to create an opening through which the installed catheter can pass as the dressing 210 is removed. Once the dressing 210 is removed, the exposed catheter and skin entrance site can be cleaned and/or sterilized as desired. A new dressing can then be installed, as described below.

An indwelling intravascular catheter that is already in place and has either not had a dressing placed, or has had its dressing removed, can have a new dressing installed. FIGS. 13A-15C and 17A-18E illustrate various exemplary embodiments of catheter dressings that can be installed around a catheter that is already inserted into a patient. These dressings generally have an open configuration in which they can be placed around an inserted catheter or can be removed from an inserted catheter. During installation, the opened dressing is placed around the catheter and reconstituted into a generally tubular shape using one or more of a variety of attachment mechanisms, including without limitation a friction fit, a male-female snap fit, an adhesive coupling, and/or a latch-type closure, thereby establishing a circumferential seal around the catheter.

Figure 13A:
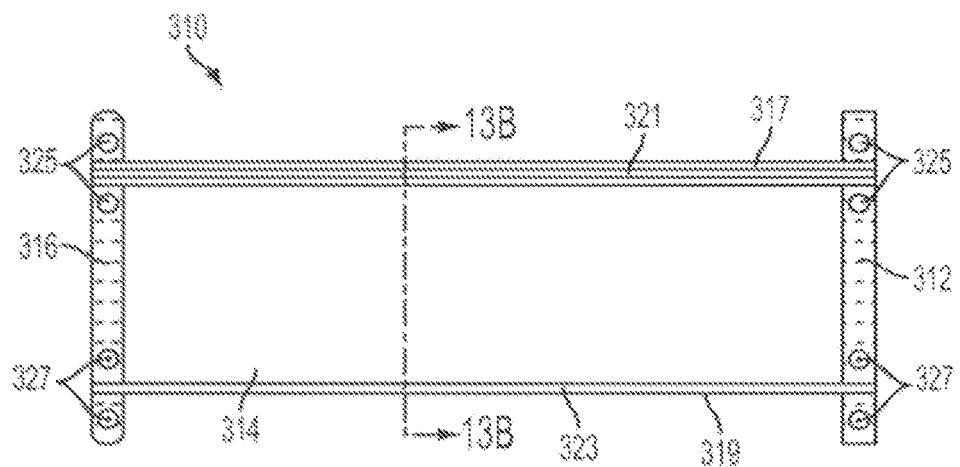
FIG. 13A is a plan view of another embodiment of a catheter dressing according to the invention in an unsealed configuration, the dressing having a friction-fit closure mechanism.
Figure 13B:
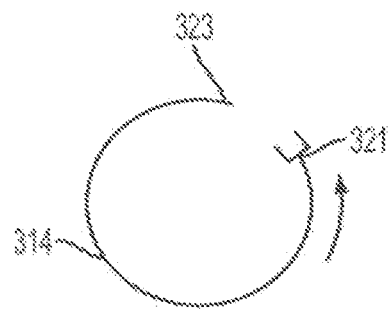
FIG. 13B is a cross-section taken along the line A-A in FIG. 13A.
Figure 13C:
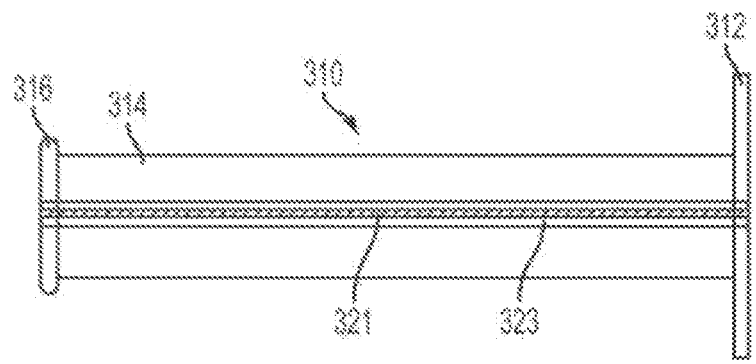
FIG. 13C is a plan view of the catheter dressing of FIG. 13A in a sealed configuration.

In FIG. 13A, a dressing 310 is shown having a plate 312, a sheath 314, and a sealing element 316. The dressing 310 is shown in an opened or unfolded configuration in which the free edges 317, 319 of the sheath 314 are separated such that the sheath 314 does not form a complete tube. A first edge 317 of the sheath 314 is provided with a longitudinal female groove 321. A second edge 319 of the sheath 314 is provided with a longitudinal male tab 323. Together, the female groove 321 and the male tab 323 form a friction-fit seal along the length of the sheath 314. The plate 312 and the sealing element 316 are similarly provided with female receptacles 325 and male projections 327 which can be selectively mated to form a friction-fit seal at the breakpoints of the plate 312 and the sealing element 316. FIG. 13B illustrates a cross-section of the sheath 314. As shown, the female groove 321 and the male tab 323 can be separated such that the sheath 314 can be installed around a catheter that has already been placed. It will thus be appreciated that the male components 319, 327 of the dressing 310 and the female components 317, 325 of the dressing 310 can be mated (as shown in FIG. 13C) to form a circumferential sterile seal around a catheter that has already been placed, or can be separated to facilitate removal of the dressing 310 from such catheters.

Figure 14A:
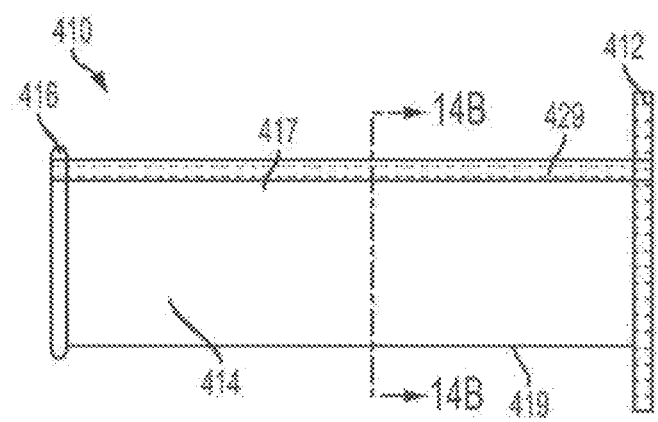
FIG. 14A is a plan view of another embodiment of a catheter dressing according to the invention in an unsealed configuration, the dressing having an adhesive closure mechanism.
Figure 14B:
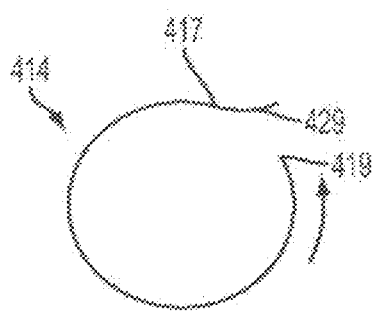
FIG. 14B is a cross-section taken along the line A-A in FIG. 14A.
Figure 14C:
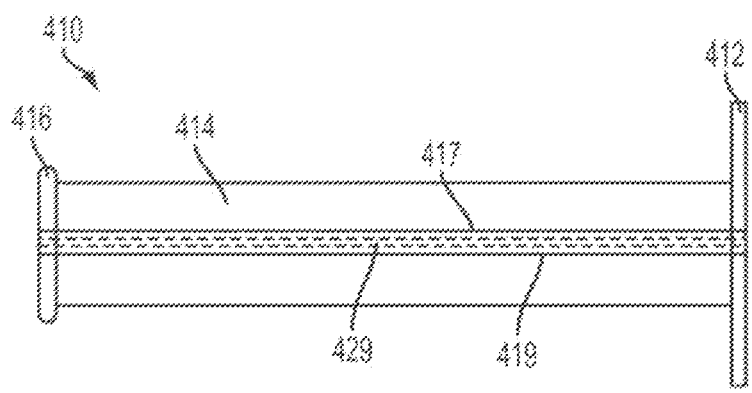
FIG. 14C is a plan view of the catheter dressing of FIG. 14A in a sealed configuration.

FIGS. 14A-14C illustrate another exemplary embodiment of a catheter dressing 410 that can be installed around an already-placed catheter. As shown, the dressing 410 includes a plate 412, a sheath 414, and a sealing element 416. The dressing 410 is shown in an opened or unfolded configuration in which opposed free edges 417, 419 of the dressing 410 are separated such that the dressing 410 does not form a complete tube. A first edge 417 of the dressing 410 is provided with an adhesive flap 429. When installed around a catheter, the first edge 417 can be placed adjacent the second edge 419 and the adhesive flap 429 can be folded across the gap between the edges 417, 419 to form a circumferential sterile seal around the catheter. It will be appreciated that the edges 417, 419 and the adhesive flap 429 extend the full length of the dressing 410 (e.g., across the plate 412 and the sealing member 416 as well). FIG. 14B illustrates a cross-section of the sheath 414. As shown, the first edge 417 and the second edge 419 can be separated such that the sheath 414 can be installed around a catheter that has already been placed. Once placed around the catheter, the edges 417, 419 can be mated as shown in FIG. 14C by folding over and adhering the adhesive flap 429 to form a circumferential sterile seal around a catheter that has already been placed. To facilitate removal of the dressing 410 from an already-placed catheter, the flap 429 can be peeled back and the edges 417, 419 separated to form an opening through which the catheter can pass as the dressing 410 is removed.

Figure 15A:
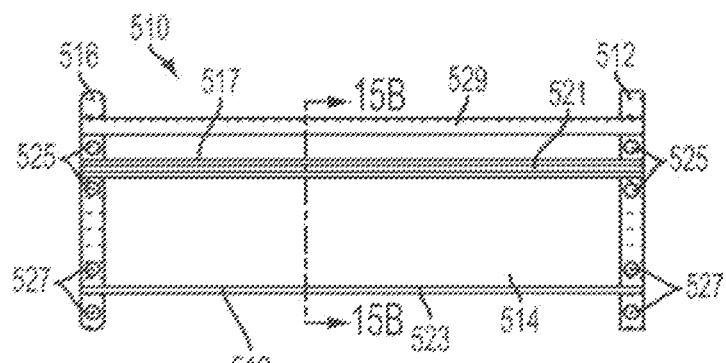
FIG. 15A is a plan view of another embodiment of a catheter dressing according to the invention in an unsealed configuration, the dressing having a friction-fit closure mechanism and an adhesive closure mechanism.
Figure 15B:
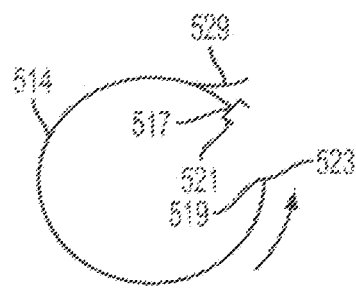
FIG. 15B is a cross-section taken along the line A-A in FIG. 15A.
Figure 15C:
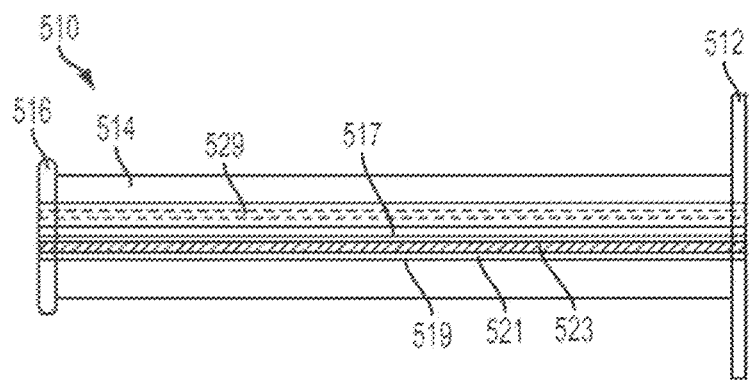
FIG. 15C is a plan view of the catheter dressing of FIG. 15A in a sealed configuration.

FIGS. 15A-15C illustrate another exemplary embodiment of a catheter dressing 510 that can be installed around an already-placed catheter. As shown, the dressing 510 includes a plate 512, a sheath 514, and a sealing element 516 and generally combines the friction-fit features of the catheter dressing 310 of FIGS. 13A-13C and the adhesive flap features of the catheter dressing 410 of FIGS. 14A-14C. The dressing 510 is shown in an opened or unfolded configuration in which opposed free edges 517, 519 of the dressing 510 are separated such that the dressing 510 does not form a complete tube. A first edge 517 of the sheath 514 is provided with an adhesive flap 529 and a longitudinal female groove 521. A second edge 519 of the sheath 514 is provided with a longitudinal male tab 523. When installed around a catheter, the male tab 523 can form a friction-fit seal with the female groove 521. The adhesive flap 529 can be folded over the second edge 519 of the sheath and adhered to an exterior thereof to reinforce the sealing engagement. The plate 512 and the sealing element 516 are similarly provided with female receptacles 525 and male projections 527 which can be selectively mated to form a friction-fit seal at the breakpoints of the plate 512 and the sealing element 516. In addition, the adhesive flap 529 can extend the full length of the dressing 510 (e.g., across the plate 512 and the sealing member 516 as well). FIG. 15B illustrates a cross-section of the sheath 514. As shown, the first edge 517 and the second edge 519 can be separated such that the sheath 514 can be installed around a catheter that has already been placed. Although the adhesive flap 529 is shown as being formed on the same edge 517 of the sheath 514 as the female groove 521, it can also be formed on the opposite edge 519 of the sheath 514 (e.g., adjacent the male tab 523). Once placed around the catheter, the edges 517, 519 can be mated as shown in FIG. 15C by engaging the male tab 523 and the female groove 521 and folding over and adhering the adhesive flap 529 to form a circumferential sterile seal around a catheter that has already been placed. To facilitate removal of the dressing 510 from an already-placed catheter, the flap 529 can be peeled back and the edges 517, 519 separated to form an opening through which the catheter can pass as the dressing 510 is removed.

FIGS. 16A-16E illustrate another embodiment of a catheter dressing 610 that generally includes a flexible sheath 614 that is formed at a non-ninety-degree angle relative to an adhesive plate 612. The angle between the sheath 614 and the plate 612 can advantageously make the dressing 610 easier to install and can reduce forces that tend to separate the plate 612 from the patient's skin 628. An access portal 646 can be provided in a sidewall of the sheath 614 as described above for accessing and manipulating the internal volume and contents of the sheath 614.

Figure 16A:
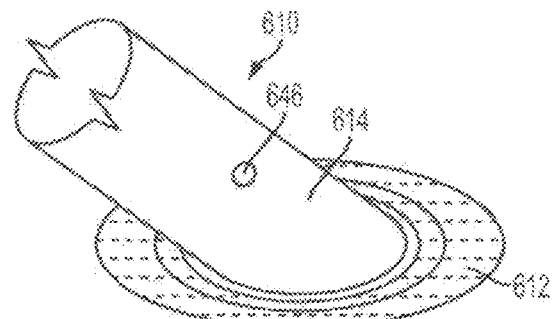
FIG. 16A is a perspective view of another embodiment of a catheter dressing according to the invention having an angled base plate.
Figure 16B:
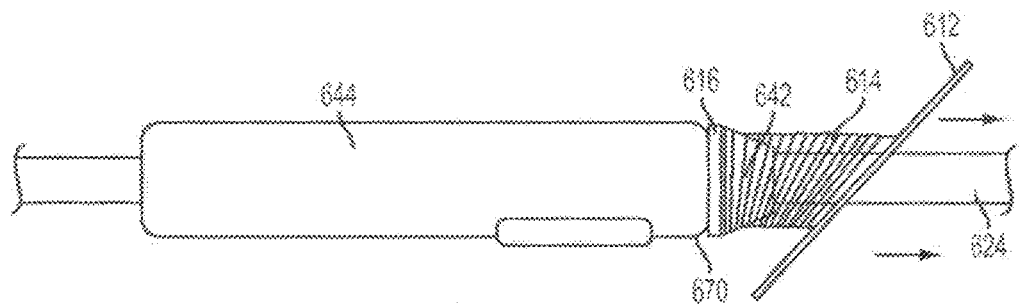
FIG. 16B is a profile view of the dressing of FIG. 16A sealed at its proximal end to a catheter hub.
Figure 16C:
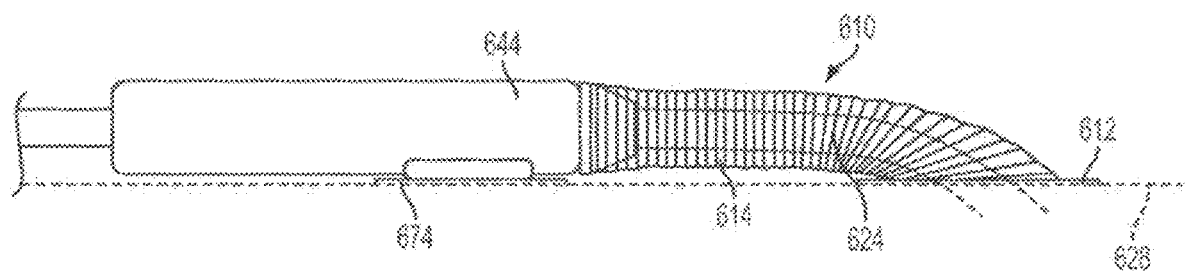
FIG. 16C is a profile view of the dressing of FIG. 16A sealed at its proximal end to a catheter hub and at its distal end to a patient.
Figure 16D:
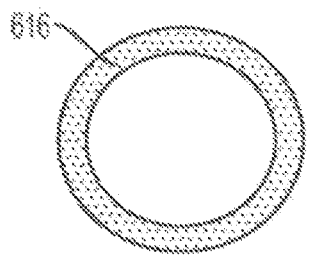
FIG. 16D is a profile view of one embodiment of a sealing element according to the invention.

As shown in FIG. 16B, a sealing element 616 formed at a proximal end of the sheath 614 can be sealably mated to a catheter 624 and/or a specially-designed catheter hub 644. In the illustrated embodiment, the sealing element 616 is advanced proximally over the nose 642 of the catheter hub 644 until it engages an annular groove 670 formed thereon. Once the dressing 610 is mated to the catheter 624 or catheter hub 644 as described above, the sheath 614 can be unfurled or unfolded distally and the adhesive plate 612 can be adhered to the patient's skin 628, as shown in FIG. 16C. It will be appreciated that, when installed as shown, the dressing 610 provides a sterile circumferential seal around the catheter 624, the catheter hub 644, and the catheter-skin insertion site. A variety of techniques can be used to effect a sealing engagement between the sheath 614 and the catheter 624 or catheter hub 644. As shown in FIG. 16D, a sealing element 616 in the form of a stretchable gasket ring can be employed to form a sealing engagement with a corresponding groove 670 formed on an outer surface of the catheter hub 644. The resilient properties of the sealing element 616 can cause it to exert a radially inward force against the groove 670, thereby forming a sterile seal.

Figure 16E:
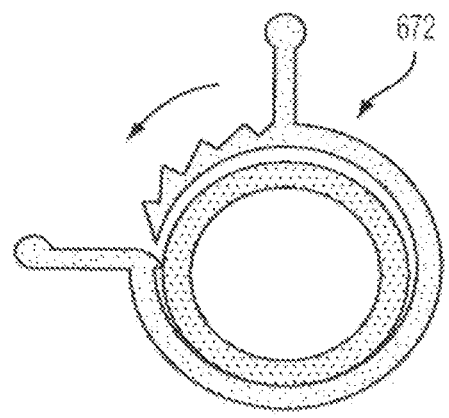
FIG. 16E is a profile view of one embodiment of a securement device according to the invention.

Alternatively, or in addition, a securement device such as a clamp 672 shown in FIG. 16E can be used to hold the sealing element 616 in position around the catheter hub 644 or to reinforce the seal formed therebetween. The clamp 672 operates substantially in the same manner as the clamping portion 88 shown in FIGS. 7A-7D. An adhesive pad 674 can be provided to attach the catheter hub 644 to the patient's skin 628, and the clamp 672 can optionally include a base portion (not shown) which can be coupled to the adhesive pad 674 as described above.

Figure 17A:
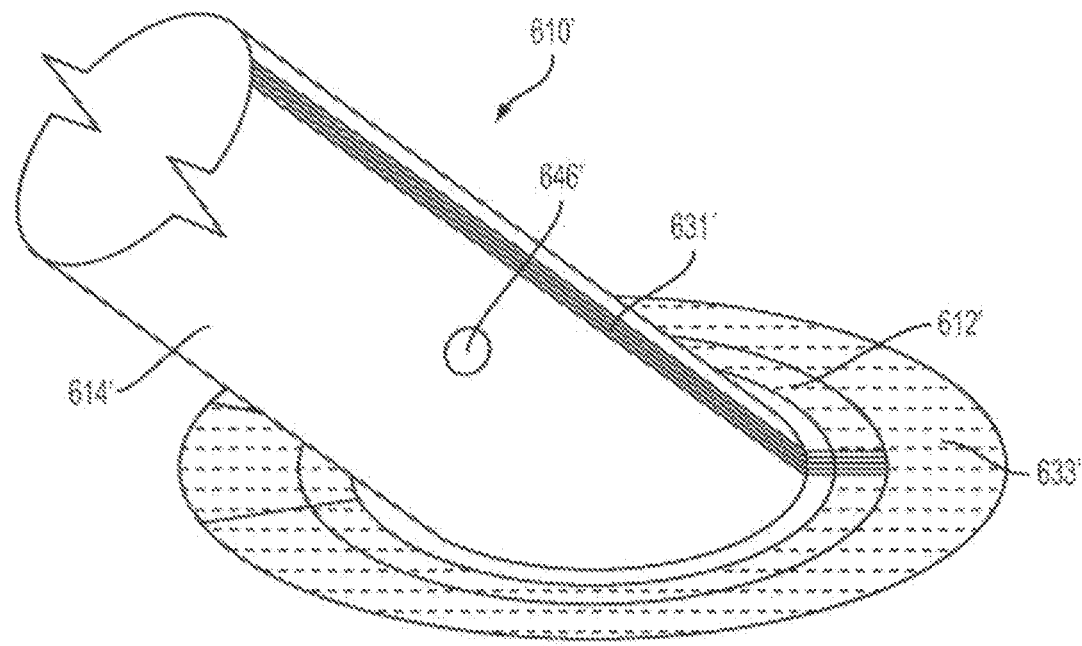
FIG. 17A is a perspective view of another embodiment of a catheter device according to the invention having a re-sealable seam and an angled base plate.
Figure 17B:
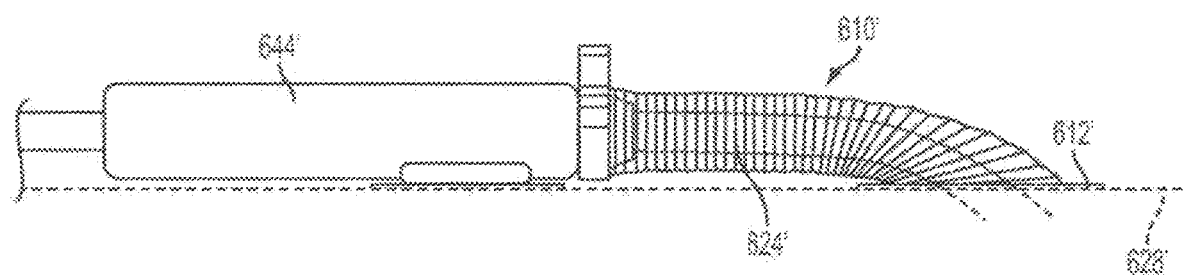
FIG. 17B is a profile view of the dressing of FIG. 17A sealed to a catheter hub and to a patient.
Figure 17C:
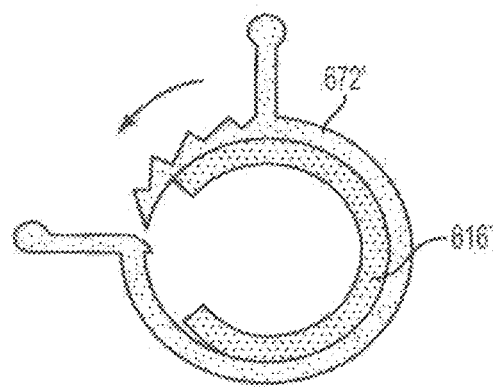
FIG. 17C is a profile view of another embodiment of a securement device according to the invention.

FIGS. 17A-17C illustrate another embodiment of a catheter dressing 610' that is substantially identical to the catheter dressing 610 shown in FIGS. 16A-16C except that it includes features for removing the dressing from, and installing the dressing around, an already-placed catheter. As shown, the dressing 610' includes a sheath 614' coupled to an adhesive plate 612' at a non-ninety-degree angle. The dressing 610' is provided with a longitudinal seam 631' that extends the entire length of the sheath 610', the adhesive plate 612', and a sealing member 616' (shown in FIG. 17C). The dressing 610' can be selectively separated and attached at the seam 631' to facilitate installation of the dressing 610' around a catheter that has already been inserted into a patient or to facilitate removal of the dressing 610' from such catheters. For example, the seam 631' can be formed with a friction-fit arrangement (e.g., as shown in FIGS. 13A-13C), with an adhesive flap arrangement (e.g., as shown in FIGS. 14A-14C), or with a combination thereof (e.g., as shown in FIGS. 15A-15C).

As shown in FIG. 17A, the seam 631' can be formed on a side of the sheath 614' that intersects the plate 612' at an obtuse angle. This can advantageously permit joining of the free edges of the sheath 614', the free edges of the adhesive plate 612', and the free edges of the sealing member 616' to occur almost in a single plane, which can ease installation and removal of the dressing 610'. A plate seal support device 633' can optionally be provided to reinforce and support the seal formed between the adhesive plate 612' and a patient's skin, as discussed in further detail below.

In use, as shown in FIG. 17B, the dressing 610' can be placed around an inserted catheter 624' and catheter hub 644'. The dressing 610' can then be joined along the seam 631' and the adhesive plate 612' can be affixed to the patient's skin 628'. A C-shaped gasket sealing element 616' and an associated clamp 672' as shown in FIG. 17C can then be installed around the hub 644' and the dressing 610' to complete a sterile circumferential seal around the catheter 624', the hub 644', and the catheter-skin insertion site.

FIGS. 18A-18E illustrate another embodiment of a catheter dressing 710 that permits a rigid or semi-rigid snap-fit seal to be formed with a catheter or a catheter hub. The dressing 710 includes a unitary body 700 having an adhesive base portion 712 configured to be adhered to a patient's skin circumferentially around a catheter-skin insertion site. The base portion 712 is generally ring-shaped and defines a distal opening 715 sized to surround the insertion site. The base portion 712 can also include a re-sealable seam 731 to facilitate installation of the dressing 710 around a catheter that is already inserted into a patient.

A rigid or semi-rigid proximal portion 714 extends vertically upward from a surface of the base portion 712 opposite to the surface that is adhered to the patient. The proximal portion 714 defines a proximal opening 713. An inner lumen 717 extends between the proximal opening 713 of the proximal portion 714 and the distal opening 715 of the base portion 712, defining a chamber in which a catheter can be positioned. The re-sealable seam 731 can also extend along the proximal portion 714 to allow the entire body 700 to be selectively separated and reattached in a sealable fashion (e.g., when it is necessary to remove or install the dressing 710 from an already-inserted catheter). The seam 731 can be formed by any of the aforementioned mechanisms, including a friction-fit, an adhesive flap, a latch-type engagement, or any combination thereof. In the illustrated embodiment, the opposed free edges of the sheath 714 are provided with corresponding male tabs 725 and female receptacles (not shown) to facilitate a friction-fit seal therebetween. The proximal portion 714 can also include one or more access portals 746 for accessing and manipulating the interior and contents of the dressing 710.

Figure 18A:
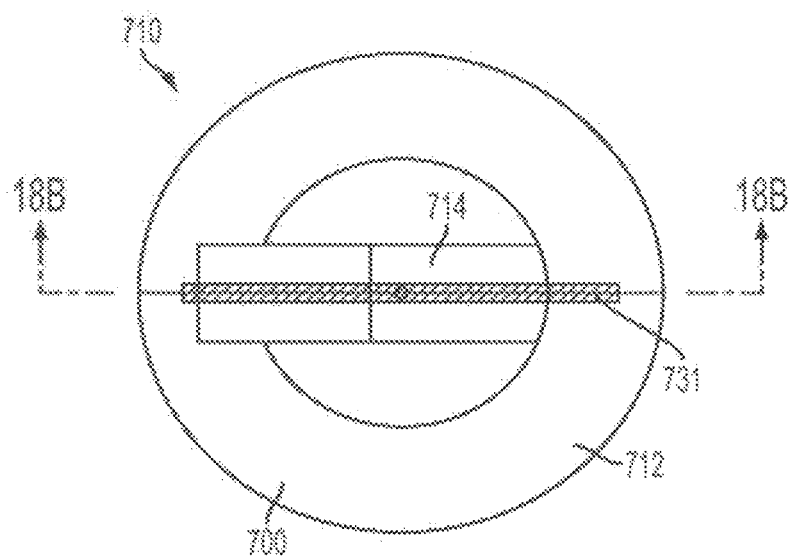
FIG. 18A is a plan view of one embodiment of a rigid or semi-rigid catheter dressing body according to the invention.
Figure 18B:
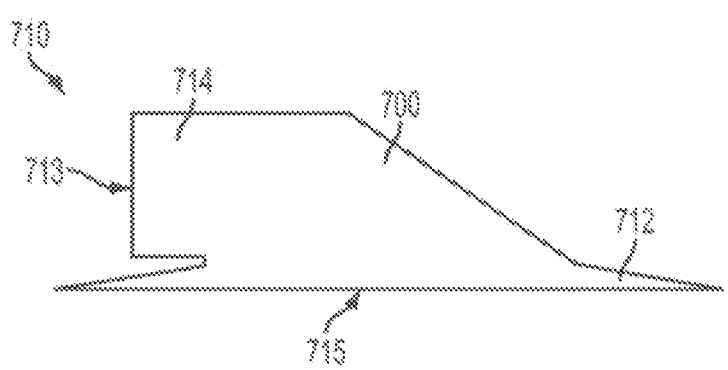
FIG. 18B is a profile view of the dressing body of FIG. 18A.
Figure 18C:
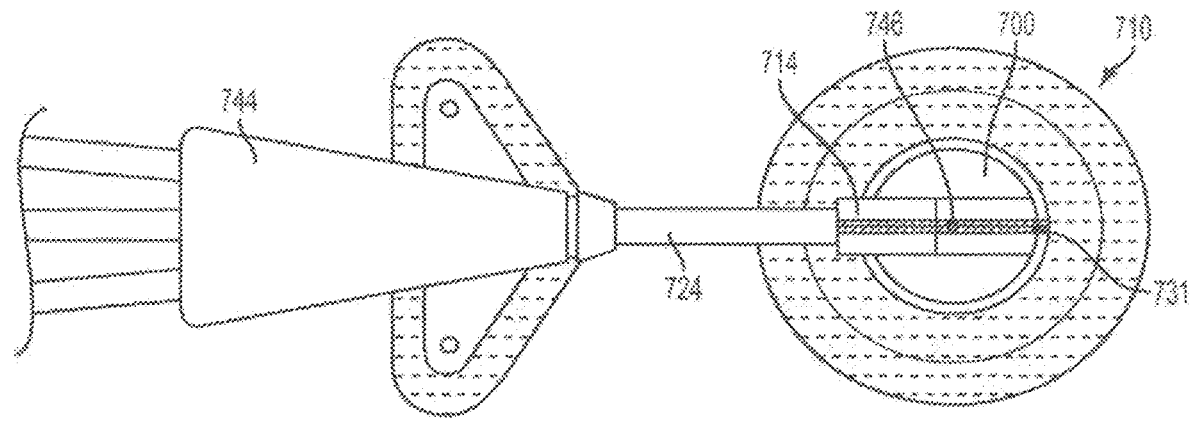
FIG. 18C is a plan view of the dressing body of FIG. 18A sealed to a catheter and a patient.
Figure 18D:
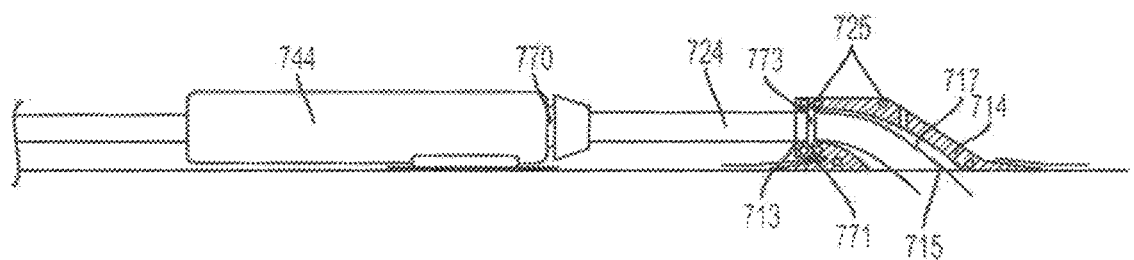
FIG. 18D is a partial cross-sectional profile view of the dressing body of FIG. 18A taken along the line A-A when the dressing is sealed to a catheter and a patient.
Figure 18E:
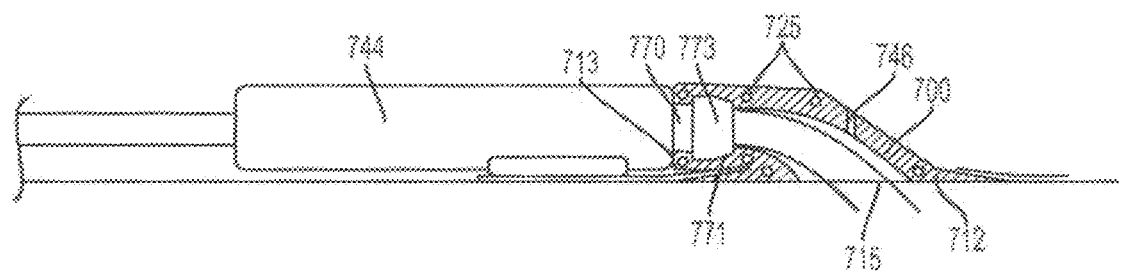
FIG. 18E is a partial cross-sectional profile view of the dressing body of FIG. 18A taken along the line A-A when the dressing is sealed to a catheter hub and a patient.

In addition, the dressing 710 can include an annular groove 771 formed in an interior surface thereof, adjacent to the proximal opening 713, that is configured to receive a corresponding annular projection 773 formed on a catheter line 724 (as shown in FIG. 18D) or on a catheter hub 744 (as shown in FIG. 18E). The annular groove 771 and the proximal opening 713 can also be seen as forming an annular lip which can engage a corresponding slot or groove 770 formed in the catheter hub 744. This groove-projection interface provides a snap-fit sealing engagement between the dressing 710 and the catheter 724 or the hub 744, which can advantageously secure the catheter 724 in position and prevent movement (e.g., longitudinal, lateral, and/or rotational) of the catheter 724 relative to the patient.

Figure 19A:
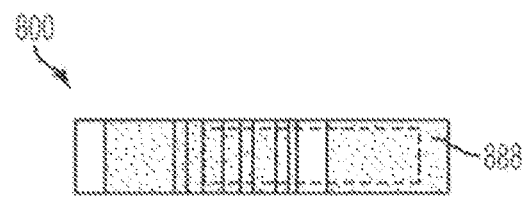
FIG. 19A is a plan view of one embodiment of a catheter seal support device according to the invention.
Figure 19B:
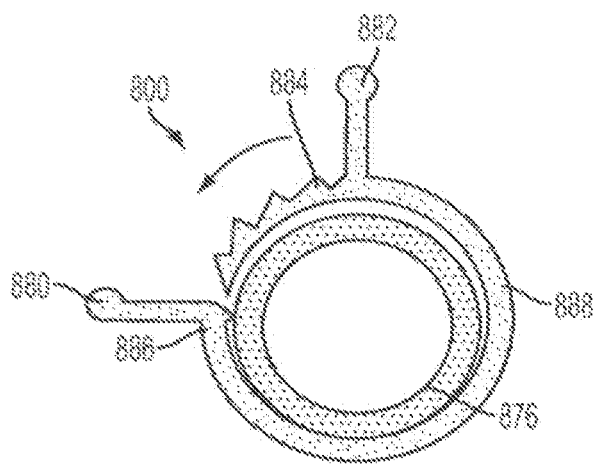
FIG. 19B is a profile view of the catheter seal support device of FIG. 19A.
Figure 19C:
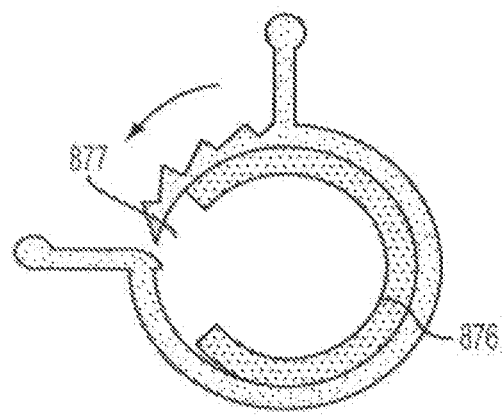
FIG. 19C is a profile view of another embodiment of the catheter seal support device of FIG. 19A.

As noted above, a variety of adjuncts to the dressings disclosed herein can be provided to support, reinforce, and otherwise supplement the sterile seals at the proximal and distal ends of the dressing. FIGS. 19A-19C illustrate one exemplary embodiment of a catheter seal support device 800 for forming or reinforcing a seal at the dressing-catheter junction. The support device 800 is configured to circumferentially surround a catheter having a dressing disposed therearound. The support device 800 can be effective to squeeze and clamp the dressing around the catheter, holding it firmly in place and reinforcing or forming a sterile seal. As shown, the support device 800 generally includes a clamping portion 888 and an inner gasket ring 876.

The clamping portion 888 includes first and second levers 880, 882 and a ratchet and pawl mechanism 884, 886. Squeezing the first and second levers 880, 882 towards each other causes the inner diameter of the clamping portion 888 to decrease as the pawl 886 rides over one or more ratchet teeth 884. As the first and second levers 880, 882 are advanced toward one another, the ratchet and pawl mechanism 884, 886 is effective to prevent movement of the first and second levers 880, 882 away from each other and thus to prevent diametrical expansion of the clamping portion 888. When necessary to release or open the clamp, the first lever 880 can be actuated to disengage the pawl 886 from the ratchet teeth 884, thereby permitting the inner diameter of the clamping portion 888 to expand and ultimately open. To ensure optimal operation of the support device 800, it can be formed from any flexible yet semi-rigid material known in the art.

The gasket ring 876 can be positioned about an inner circumference of the clamping portion 888 and can be configured to prevent abrasion of a dressing around which the clamping portion 888 is placed. The gasket ring 876 can also ensure that the radial force applied by the support device 800 is substantially uniform about the circumference of the dressing. As shown in FIG. 19C, the gasket ring 876 can have an opening 877 such that the gasket ring 876 is substantially C-shaped and thus can be installed around an already-dressed or already-inserted catheter. When used with a dressing having a longitudinal seam formed therein for separating the dressing, it is preferred that the opening 877 in the gasket ring 876 be placed on the opposite side of the dressing (e.g., such that the opening 877 is disposed 180 degrees from the seam in the dressing). This can desirably provide a more stable, reliable seal.

FIGS. 20A-20D show one embodiment of a plate seal support device 900. The support device 900 generally comprises a circular adhesive ring 901. The ring 901 has a break 903 formed therein such that the ring 901 can be opened, placed around an already-installed dressing, and then closed (e.g., reconstituted as a circle). The ring 901 can include an overlap region 905 such that the free ends of the ring overlap one another. In one embodiment, the overlap region 905 can extend between 30 and 60 degrees around the ring 901.

Figure 20A:
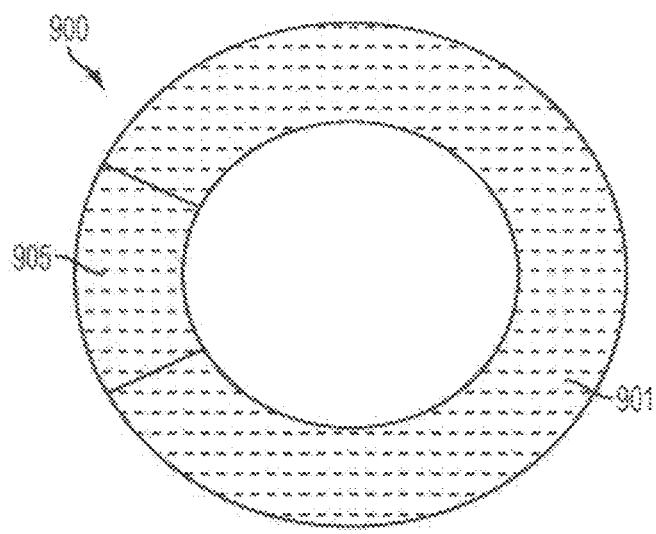
FIG. 20A is a plan view of one embodiment of plate seal support device according to the invention.
Figure 20B:
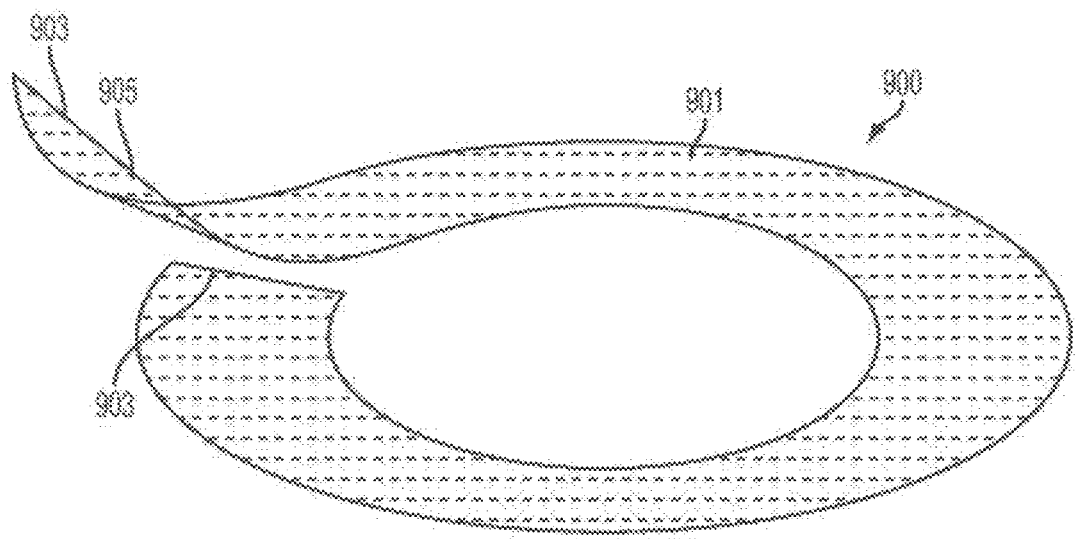
FIG. 20B is a perspective view of the plate seal support device of FIG. 20A.
Figure 20C:
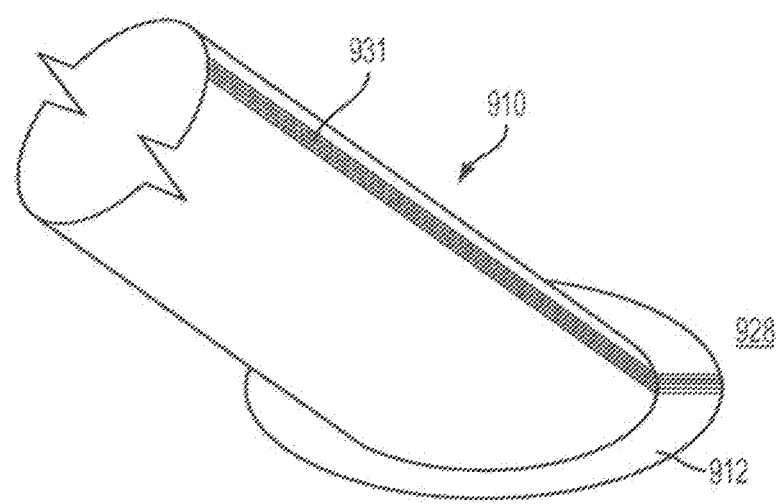
FIG. 20C is a perspective view of one embodiment of a re-sealable catheter dressing according to the invention.
Figure 20D:
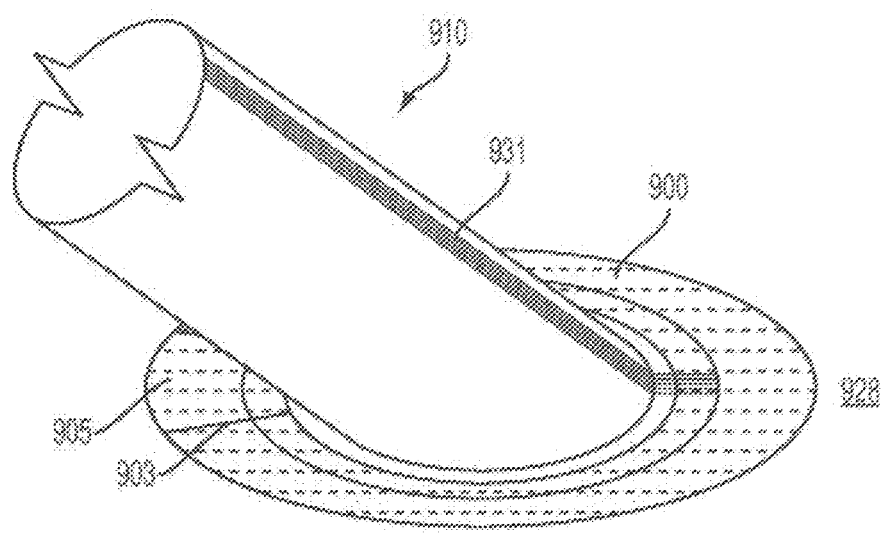
FIG. 20D is a perspective view of the plate seal support device of FIG. 20A installed over the dressing of FIG. 20C.

In use, the support device 900 can be placed to further seal the outer edge of a catheter dressing's adhesive plate to a patient's skin and to prevent the plate of the dressing from inadvertently separating at a re-sealable seam. FIG. 20C illustrates an exemplary catheter dressing 910 with which the support device 900 can be used. The dressing 910 is adhered to a patient's skin 928 via a circular adhesive plate 912. A longitudinal seam 931 is formed in the dressing 910 (including in the plate 912) to allow the dressing to be installed on or removed from an already-placed catheter. As shown in FIG. 20D, the support device 900 can be opened at the break 903, positioned around the dressing 910, and closed such that the overlap portion 905 adheres to a top surface of an opposed free end of the adhesive ring 901. It will be appreciated that the inner diameter of the support device 900 is smaller than the outer diameter of the adhesive plate 912 and the outer diameter of the support device 900 is larger than the outer diameter of the adhesive plate 912. Accordingly, the support device 900 overlaps a portion of the adhesive ring 912 and a portion of the patient's skin 928, thereby reinforcing and/or forming a circumferential seal between the dressing 910 and the skin 928. As shown, the break 903 and overlap portion 905 of the support device 900 can be positioned on a side of the dressing 910 opposite to the seam 931 such that the two do not overlap. For example, the break 903 in the support device 900 can be positioned 180 degrees from the seam 931 in the dressing 910, which can provide a more stable and reliable seal.

The catheter dressings and dressing assemblies described herein can also be packaged in the form of a kit including dressings and/or assemblies of various sizes for use with various sized catheters. Such kits can also include catheters of various sizes and types, including customized or modified catheters designed specifically to interface with the dressings and dressing assemblies described herein.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a caregiver immediately prior to a catheterization procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before use. First, a new or used device is obtained and if necessary cleaned. The device can then be sterilized. In one sterilization technique, the instrument is placed in a closed and sealed container, such as a plastic or TYVEK bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical field.

It is preferred that the device is sterilized. This can be done by any number of ways known to those skilled in the art including beta or gamma radiation, ethylene oxide, steam, and/or a liquid bath (e.g., cold soak).

FIGS. 21A-21I present a series of views that demonstrate the step by step process of two piece catheter hub Seldinger insertion, saline flush/hub cap attachment, saline flushing of the catheter, dressing mounting over the saline syringe mounting handle, removal of the syringe/mounting handle, and then attachment of a fluid line, or optionally, placement of the hub cap sterility preserving protection device. Details of this insertion/dressing placement and use process are as follows (FIGS. 5.1-5.9).

Figure 21A:
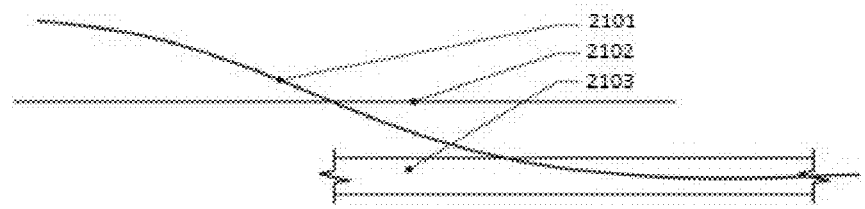
FIGS. 21A-21I are a series of views that demonstrate the step by step process of a two piece catheter hub Seldinger insertion, saline flush/hub cap attachment, saline flushing of the catheter, dressing mounting over the saline syringe mounting handle, removal of the syringe/mounting handle, and then attachment of a fluid line, or optionally, placement of the hub cap sterility preserving protection device.

FIG. 21A depicts percutaneous insertion of the catheter guidewire/insertion wire 2101 into the target blood vessel 2103 under the skin surface 2102.

Figure 21B:
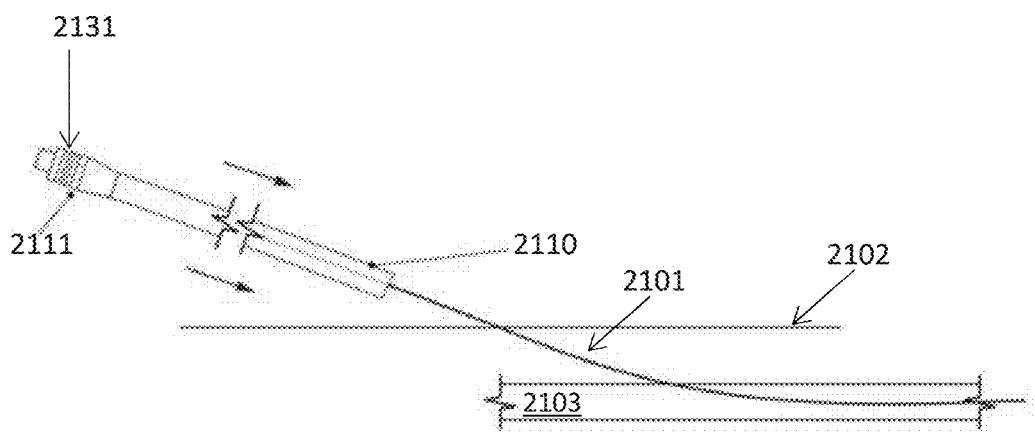

FIG. 21B depicts sliding the one-piece catheter body 2110 and hub base 2111, having an integrated dressing mating point or mating feature 2131, over the guidewire 2103.

Figure 21C:
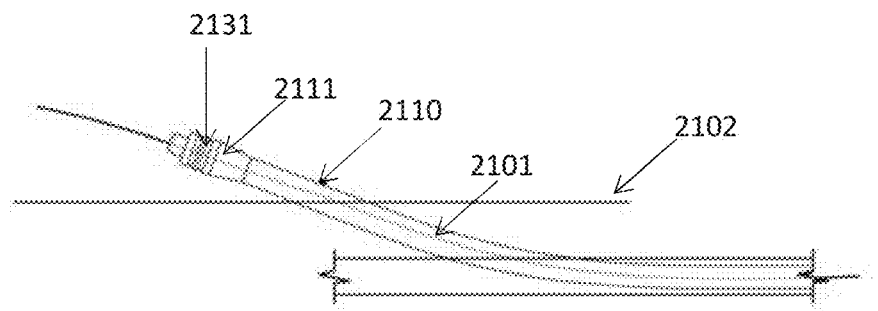

FIG. 21C depicts catheter 2110 inserted to final/desired insertion point/depth over the guidewire/insertion wire 2101. Evident is the insertion wire/guidewire 2101 protruding through the male extension (and its re-sealable membrane) of the hub base 2111.

Figure 21D:
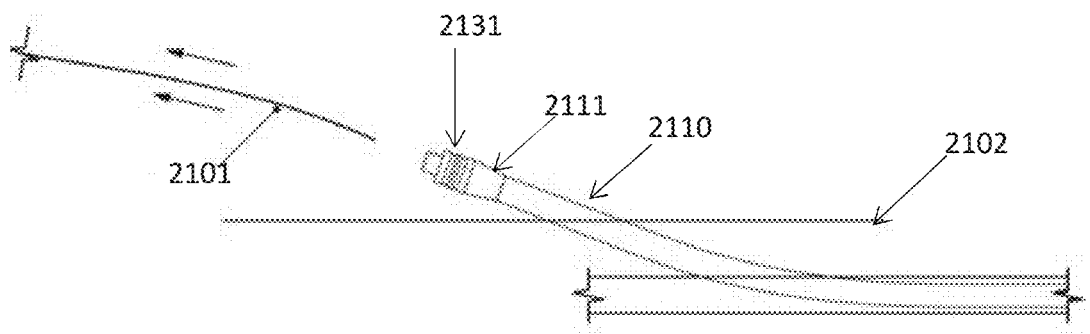

FIG. 21D shows removal of the insertion wire 2101.

Figure 21E:
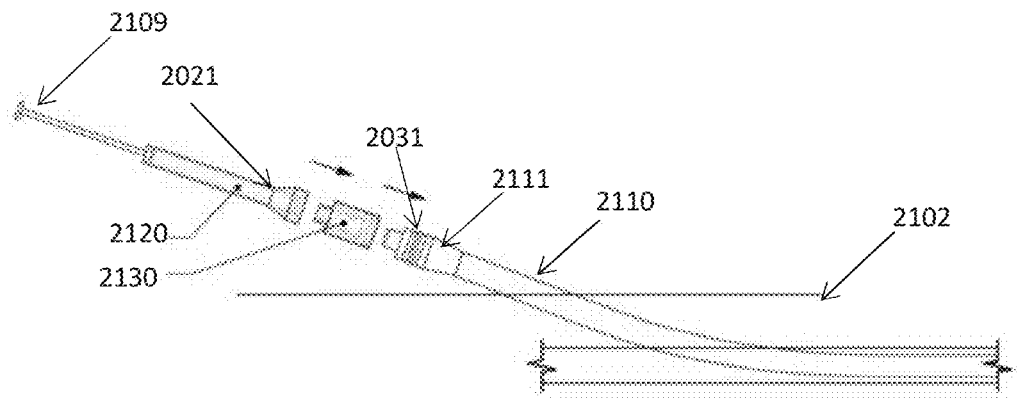

FIG. 21E demonstrates attachment of the saline flush mounting handle 2120 (e.g., saline syringe) and hub cap 2130 (note that these can be packaged as a pre-assembled unit, or they can be joined together on the sterile field) to the catheter hub base 2111.

Figure 21F:
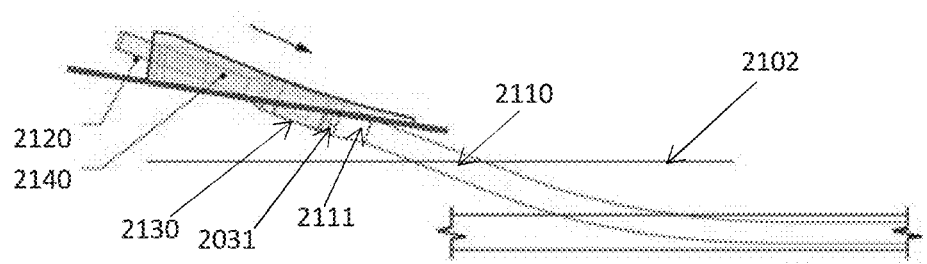

FIG. 21F depicts (1) the flushed catheter (with the plunger 2129 of the syringe 2120 fully depressed), and (2) the integrated sterile sealing dressing 2140 being mounted over the syringe mounting handle 2120. The diameter of the syringe mounting handle 2120 (i.e., less than the catheter hub base stop flange 2031) should be noted, as well as the flaring outward at the distal end 1021 of the syringe/mounting handle 2120 to allow smooth mounting transition from the syringe/mounting handle 2120 to the hub base 2111.

Figure 21G:
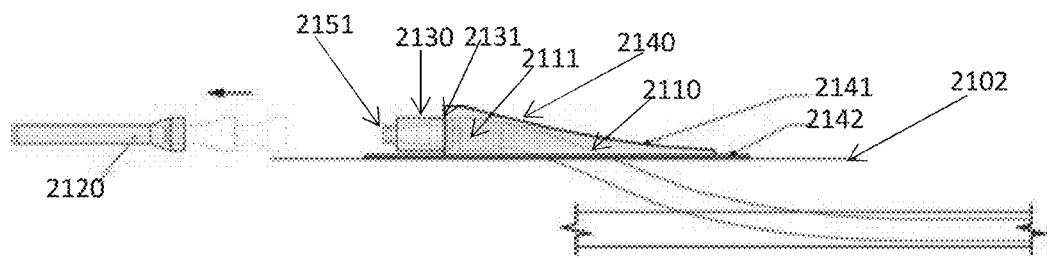

FIG. 21G demonstrates the sterile sealing dressing 2140 in its final mounted position. The syringe mounting handle 2120 has been detached (left side of drawing), leaving the hub cap component 2130 of the 2-piece hub in place, with its protruding needle or needleless connector(s) 2151. The adhesive base plate 2142 has been attached to the skin 2102 circumferentially around the catheter-skin insertion site. The mating seal between the dressing 2140 and the interconnector-cap 2130 (or catheter hub base 2130) has been effected. The stop flange component 2131 of the hub base 2111 has been engaged, preventing withdrawal of the catheter 2110 from the attached dressing. The only way that the catheter 2110 can be removed is to remove the entire adhesive base plate 2142 dressing from the patient's skin 2102.

Note that a version of Seldinger type insertion can be practiced as an alternative, whereby the insertion wire 2101 is passed through a continuous channel that exists in the hub base 2111, hub cap 2130, and attached specially constructed insertion syringe 2120 (wherein the syringe 2120 has a central channel that allows through egress of the insertion wire 2101), so that the entire catheter 2110 and attached mounting handle syringe 2120 are passed over the insertion wire 2101.

Figure 21H:
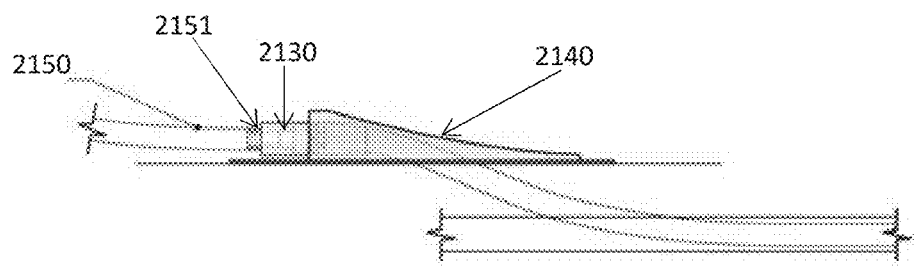

FIG. 21H demonstrates attachment of an IV line 2150 to the needle or needleless connection port 2151.

Figure 21I:
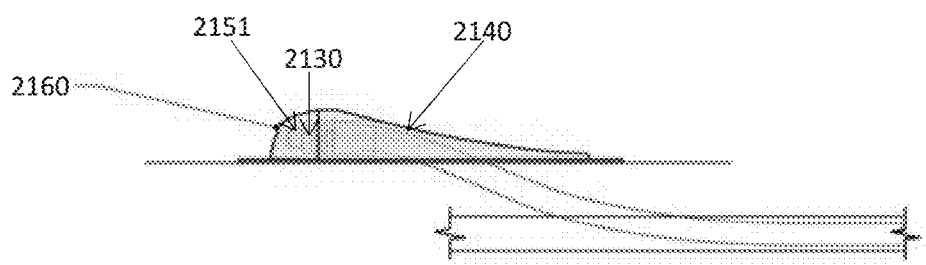

FIG. 21I depicts placement of the sterility preserving ergonomic hub cap 2160 protection device that serves to ergonomically protect the connection point 2151 of the hub cap 2130 (e.g., prevent catching on clothing), and also to maintain it in a continuous sterile ready-to-use state.

Figure 22A:
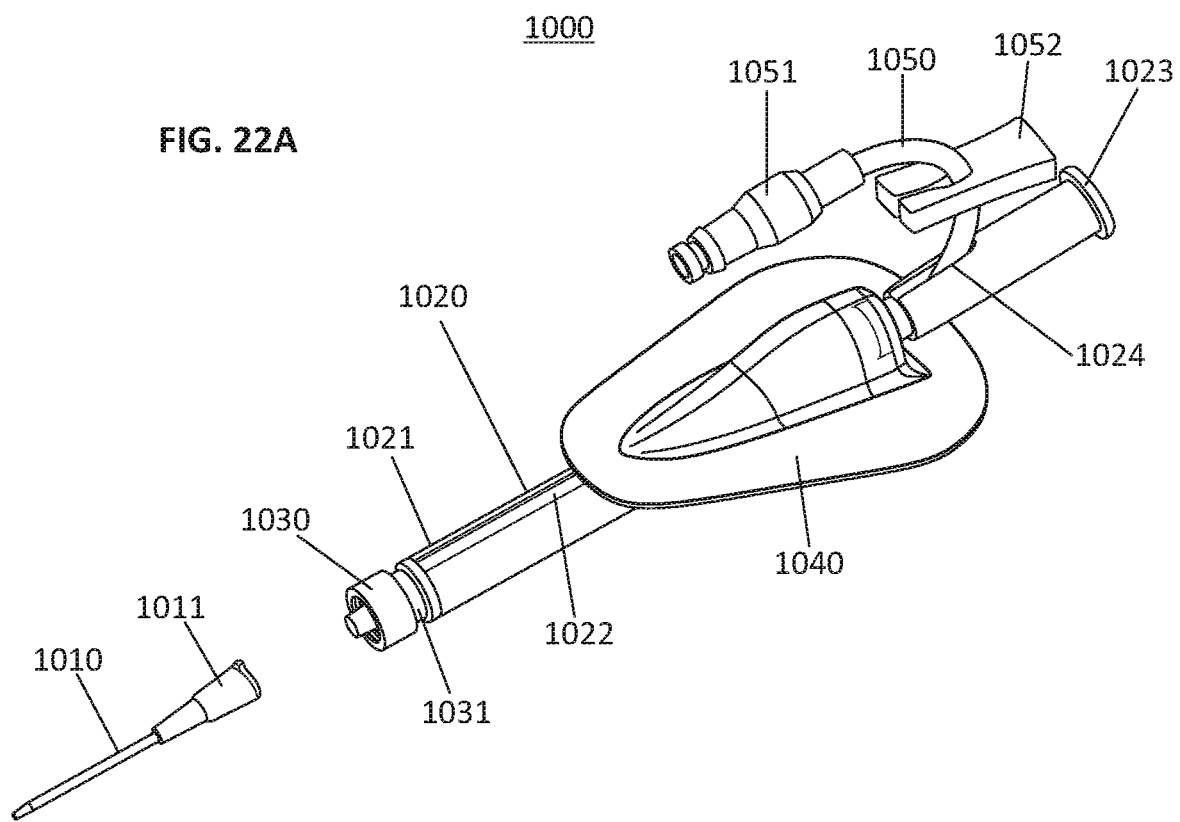
Figure 22B:
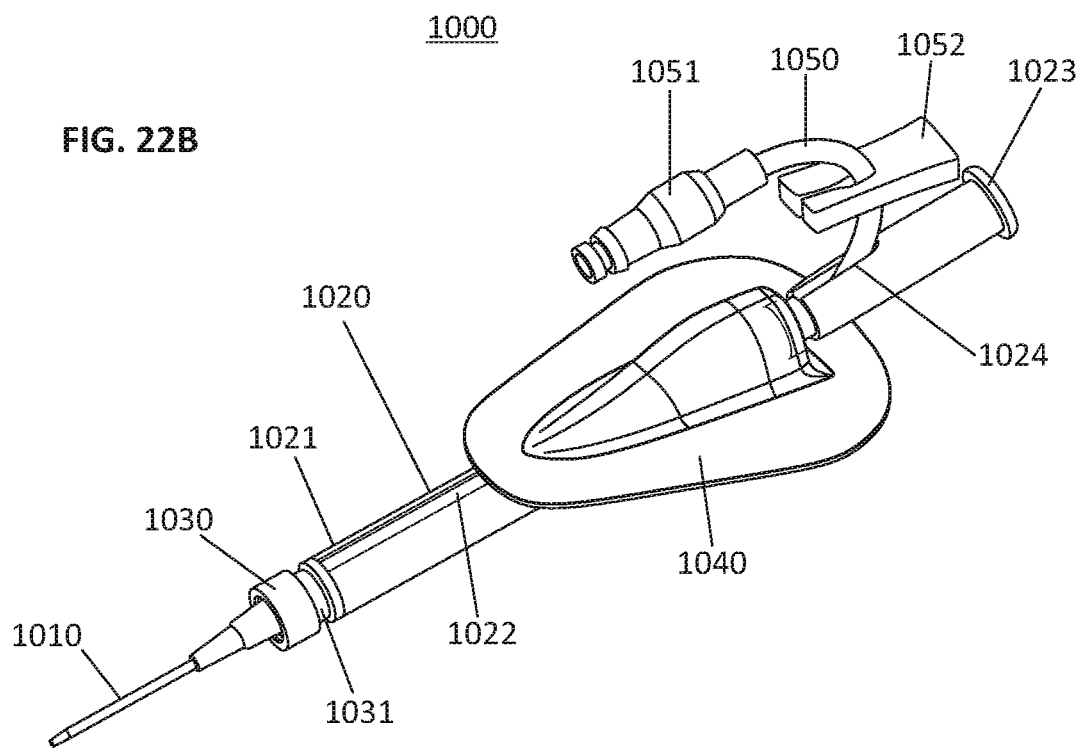

FIGS. 22A-22F show different views of an integrated catheter extension and dressing assembly 1000. In FIG. 22A, the catheter extension system 1000 has a connector 1030 for connection to a catheter or IV needle 1010 at catheter hub 1011. The connector has a mounting point 1031 (e.g., an annular groove, ring, stop flange, or combination thereof). The connector is adapted to mate or couple to a hub 1011 or any conventional IV needle, catheter or catheter assembly at a distal end. The connector is also adapted to mate or couple a mounting handle (i.e., a mounting handle connector) 1020 at a proximal end. The mating to the catheter hub can be performed by any known means, such as any Luer-Lock™ connector, as illustrated in FIG. 22A, a Clave® connector and others. The mating of the connector to the mounting handle can also be performed by known means, such as male and female Luer-Lock™ connectors, snap-fit, bayonet construction, screw thread, twist lock, etc. The connector provides sterility and fluid communication between catheter 1010 and tubing 1050.

The integrated catheter extension system 1000 also has an integrated mounting handle 1020. As illustrated in FIG. 22A, the mounting handle is preassembled and connected to connector 1030. The mounting handle 1020 is generally cylindrical and sized such that a medical dressing 1040 can be disposed thereon. Preferably, the maximum outer diameter of the mounting handle 1020 is less than or equal to the diameter of the specified cap mounting point 1031. This can allow the dressing 1040 to be slid over the mounting handle 1020 so that it can be mounted at the specified connector mounting point 1031. The mounting handle has a distal end 1021 which is adapted to be mated and connected to the connector 1030. The mounting handle also has a proximal end 1023. As illustrated in FIG. 22A, proximal end 1023 of the mounting handle 1020 has a top collar or circumferential flange to allow a user to grip the catheter extension system. A channel or groove 1022 runs along a longitudinal length of the mounting handle 1020. Channel or groove 1022 allows for an extension tubing 1050 to be disposed substantially within the mounting handle 1020. A groove end 1024 is at or near the proximal end 1023 of the mounting handle 1020. (Although groove 1022 is shown as terminating before the proximal end of the handle 1020, it should be clear that the groove 1022 can extend the entire length of the handle.) The extension tubing 1050 loops out of or exits groove 1022 at groove end 1024. The groove is sized so that tubing 1050 fits substantially or entirely within the groove.

In some embodiments, the mounting handle 1020 has a hollow core, sized to receive and house extension tubing 1050. The mounting handle 1020 completely surrounds the extension tubing 1050. The extension tubing 1050 exits the mounting handle at the proximal end 1023.

The extension tubing 1050 can optionally have a slide clamp 1052. Also shown in FIG. 22A, is a needle-free connector 1051 attached at an end of the extension tubing. Other connectors, valves, injection ports, tubing and the like can be mated with tubing 1050.

The mounting handle also has an integrated circumferentially sealing securement dressing 1040. Mounting handle 1020 is sized and configured so that the dressing 1040 slides along the length of the mounting handle 1020. After sliding the dressing 1040 along the mounting handle, the dressing is secured and fitted to the connector 1030 by mating to the annular fitting, 1031, e.g., a groove, ring and/or stop flange, on the connector. Other snap-fit and/or friction fit configurations that provide both longitudinal and circumferential movement of the catheter are contemplated. This mating prevents a catheter 1010 from inadvertently being pulled out of the insertion site. The dressing also provides a sterile seal at and around the injection site. The catheter 1010 is illustrated in FIG. 22A (e.g., in a patient), but not connected to the catheter extension system 1000.

The catheter system 1000 in FIG. 22A can be connected to catheter 1010 illustrated in FIG. 22B-22F using a Luer-type connector 1030. It will be readily apparent that other appropriate Luer-based connectors and fittings can be used to connect the catheter extension system 1000 to catheter 1010.

Figure 22C:
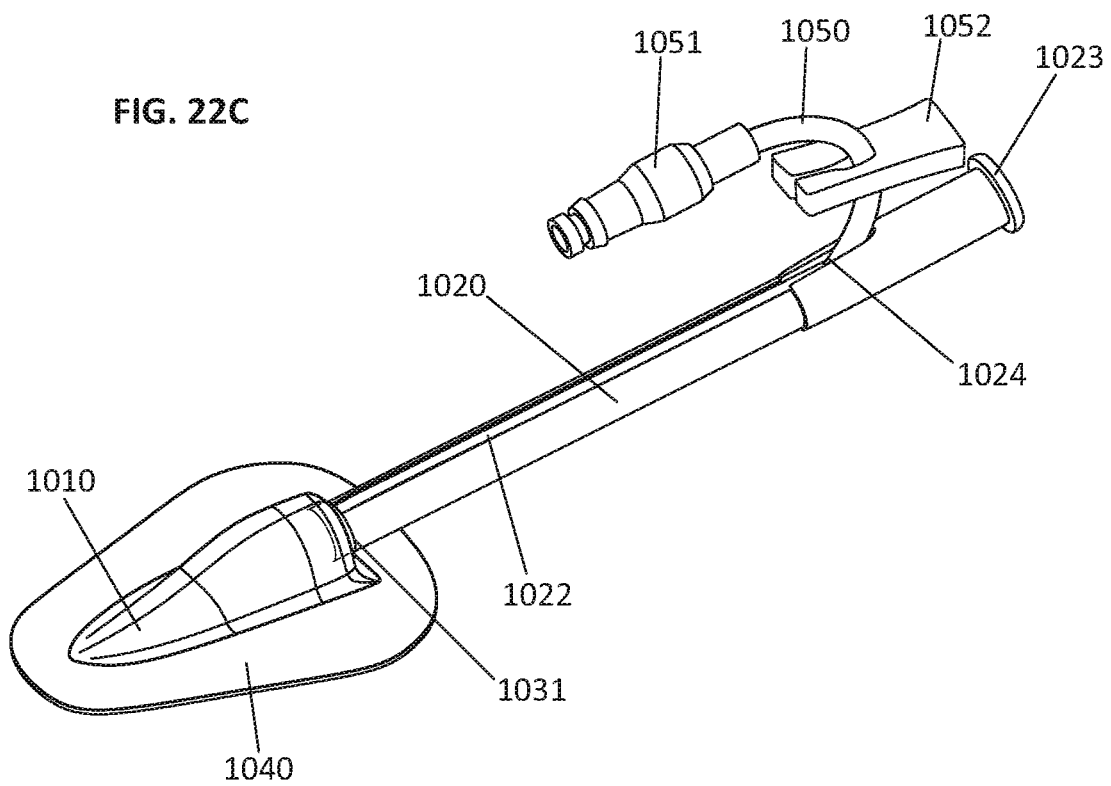
Figure 22D:
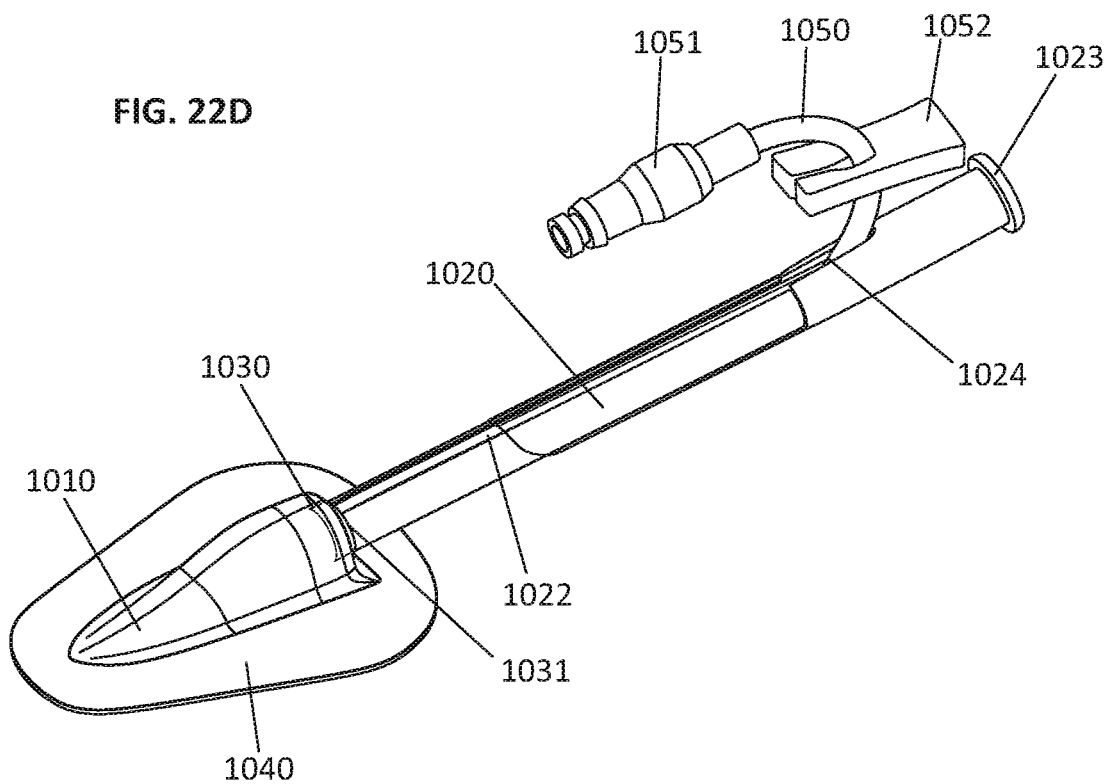

Once connector 1030 is connected and secured to catheter 1010, dressing 1040 slides down and over the mounting handle 1020, as illustrated in FIGS. 22C and 22D. The dressing 1040 attaches to and mates with the mounting point 1031 (e.g., annular groove, ring and/or stop flange) of connector 1030, shown in FIG. 22D. In some embodiments, a peelable backing 1041 is removed from dressing 1040 (see FIG. 22E). After removable of the backing 1041, an adhesive is exposed for securing the dressing 1040 to a patient's skin at a catheter insertion site.

Figure 22E:
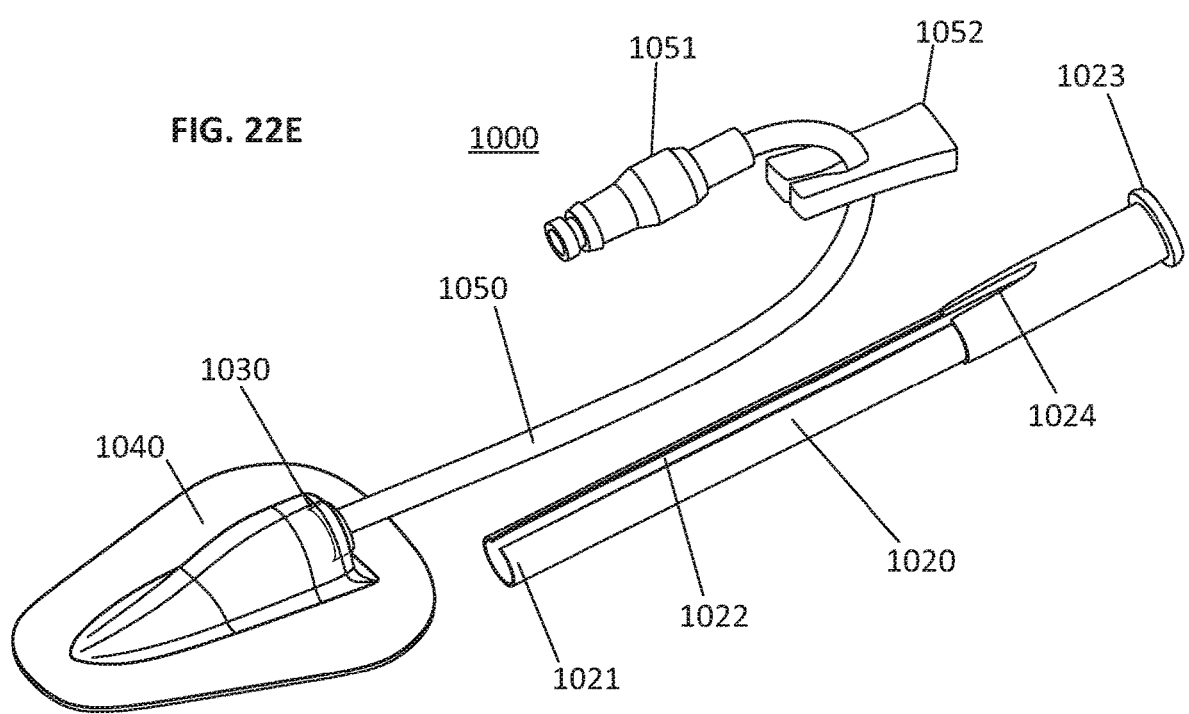

The dressing can further include a bladder, sponge or other reservoir 1042, as shown in FIG. 22E, to deliver an antimicrobial agent to the skin at the insertion site. For example, a bladder 1042 can be filled with an antimicrobial fluid, such as chlorhexidine (CHD) or isopropyl alcohol and a simple squeeze at the time of placement (or during adhesion of the dressing to the skin) can suffice to disinfect the site of any surface pathogens.

In some embodiments, the catheter extension system 1000 includes a single-use or re-fillable bladder. The re-fillable bladder can be filled with chlorhexidine or other sterilizing solution. The chlorhexidine is released from the bladder by squeezing the dressing 1040.

Finally, the mounting handle 1020 is removed from the extension system 1000 by un-mating the distal end 1021 of the mounting handle 1020 from the connector 1030, illustrated in FIG. 22F. In some embodiments, a one half or less rotation of the mounting handle with respect to connector disconnects these elements. Extension tubing 1050 is pulled out from groove 1022 and is separated from the mounting handle 1020.

Figure 22G:
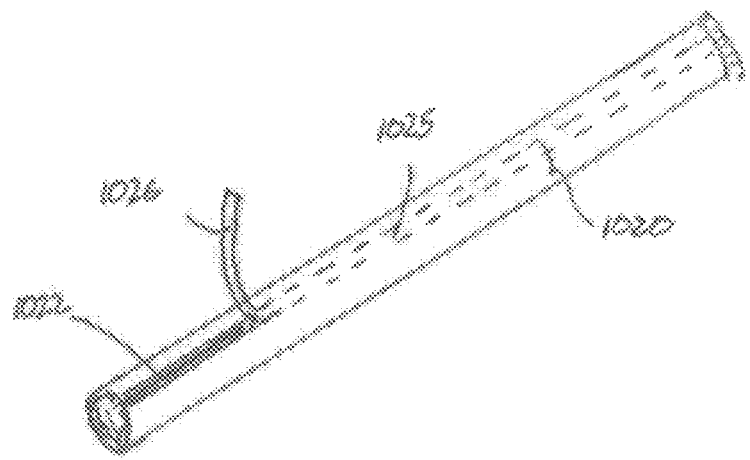
FIGS. 22G-22H are embodiments of a mounting handle from the integrated catheter extension system of FIGS. 22A-22F.
Figure 22H:
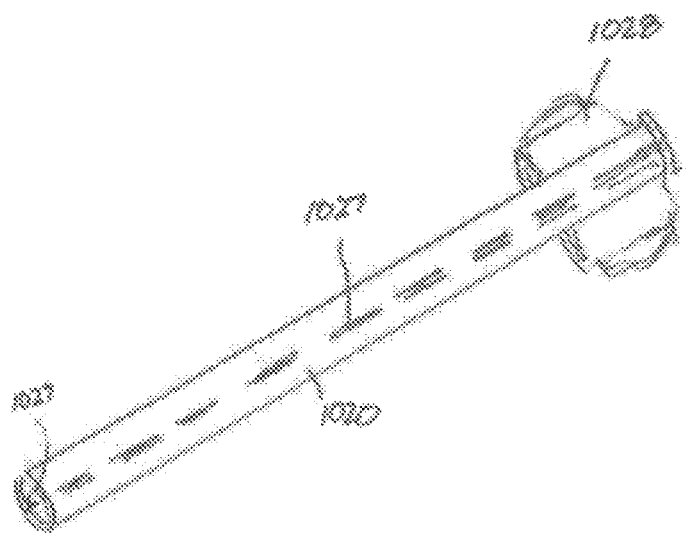

Alternatively, as shown in FIG. 22G, the releasable mounting handle 1020 can be splitable along a longitudinal or axial line 1025 with the aid of a peel-away strip 1026 to create a groove 1022. In yet another embodiment, as shown in FIG. 22H, two split lines 1027 can be formed in the handle 1020 to facilitate splitting the handle into two pieces with the aid of breakaway tabs 1028. Various other designs can be employed to permit release and disposal of the mounting handle.

In some embodiments, a flush assembly (see FIGS. 23A-23B) is connected or mated to a proximal end of tubing. Sterile saline or other injectable agents can be contained within the flush assembly. When the catheter extension system 1000 is ready to be mated to a catheter hub, saline can be flushed through the tubing 1050 and connector 1030, removing air within the system (i.e., in the tubing and connector). Once the connector 1030 is mated with the catheter hub, saline can be flushed through any blood that could clot and clog an inserted catheter. In this embodiment, the tubing 1050 can extend the entire length of the mounting handle 1020 and past the proximal end 1023. The tubing can be connected directly to a saline flush device (See, e.g., saline flush devices disclosed in U.S. application Ser. No. 13/613,509). Connection or mating of the tubing to the saline flush device can be performed by a Luer Lock® type connector. Once the system is flushed, the flush device can be detached from tubing 1050. Also, the mounting handle 1020 can be detached from the connector 1030 and slide over tubing 1050.

For example, FIG. 23A is a side view of a saline flush assembly 34 configured to mate with a standard Luer Lock® type connection device or tubing (e.g., tubing 1050). The assembly 34 is shown as it might look after removal from its sterile packaging, or it can be part of the system illustrated in FIGS. 22A-22F. A plunger 36 is shown in a withdrawn position, ready to inject once a Luer Lock® connector 38 is connected to a extension tubing 1050 of the catheter extension system. Sterile saline or other injectable agents can be contained in a chamber 40 in the flush assembly 34. The proximal "plunger handle" end 44 of the saline flush handle 34 can be uniquely tapered to allow easy mounting of the dressing 30 onto the handle 34. In particular, the proximal end 44 of the handle 34 can have a first diameter that gradually tapers distally into a second diameter that is greater than the first diameter. As noted above, the first and second diameters, and the maximum outer diameter of the handle 34, can all preferably be less than or equal to the outer diameter of a dressing mating point on the catheter, catheter hub, or catheter hub cap.

FIG. 23B is a side view of a saline flush handle 46 configured to mate with a Clave® needleless connection device. The handle 46 is shown as it might look after removal from its sterile packaging. The plunger 48 is shown in a withdrawn position, ready to inject once a Clave® connector 50 is connected to a catheter hub after successful catheter insertion. Sterile saline or other injectable agents can be contained in a chamber 53 in the handle. Like the embodiment shown in FIG. 23A, the saline flush handle 46 of FIG. 23B can include a uniquely tapered proximal end 52 to allow easy mounting of the dressing 30 onto the handle 46. In particular, the proximal end 52 of the handle 46 can have a first diameter that gradually tapers distally into a second diameter that is greater than the first diameter. The first and second diameters, and the maximum outer diameter of the handle 46, can all preferably be less than or equal to the outer diameter of a dressing mating point on the catheter, catheter hub, or catheter hub cap.

Figure 24A:
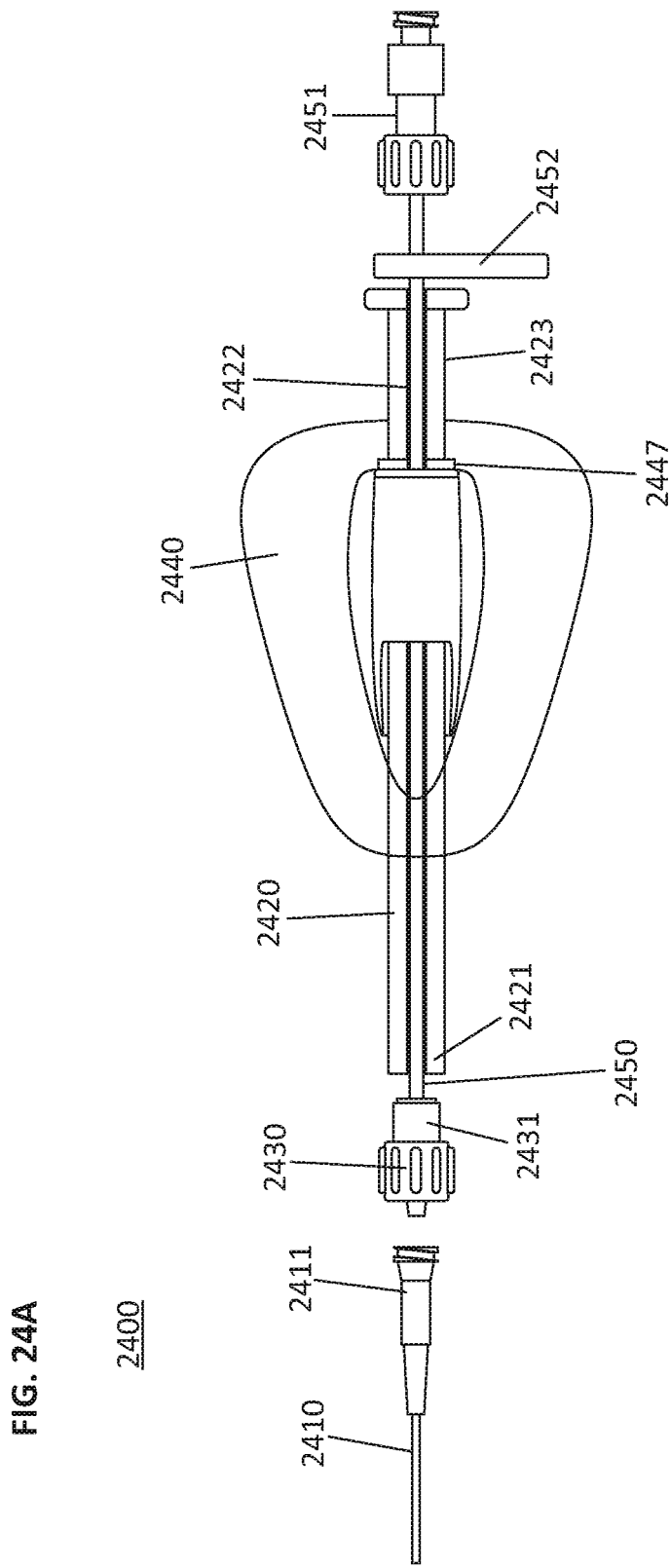
Figure 24B:
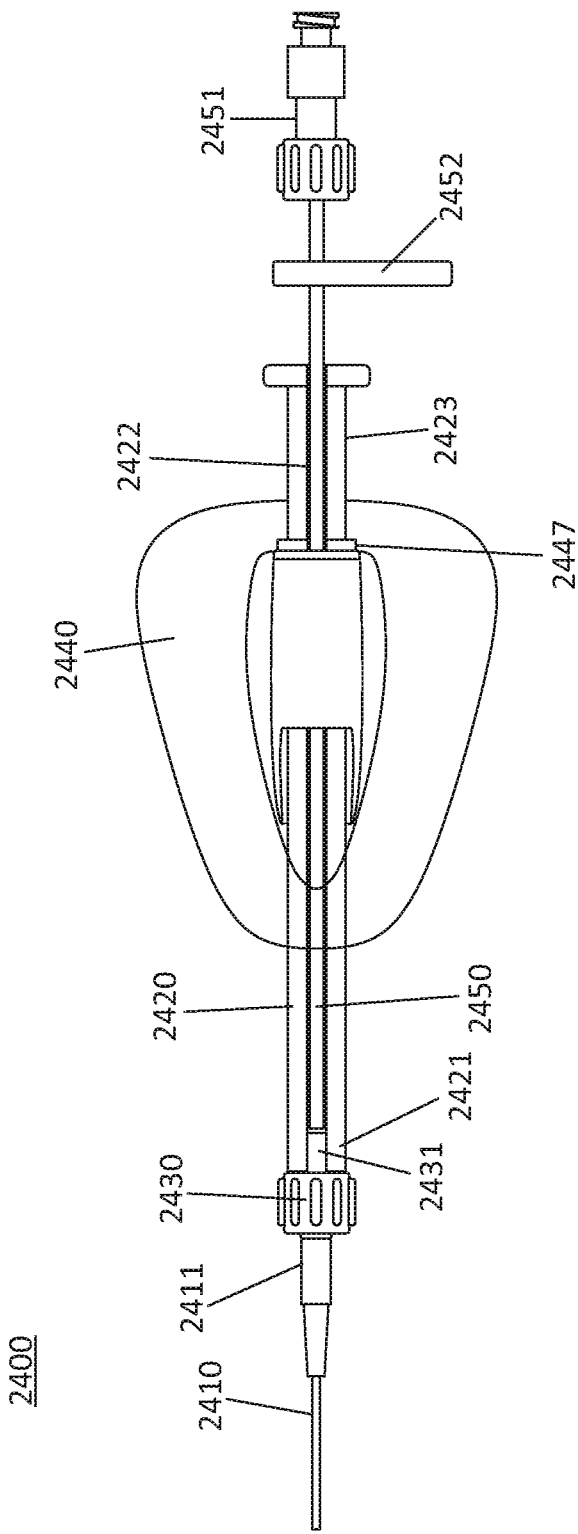
Figure 24F:
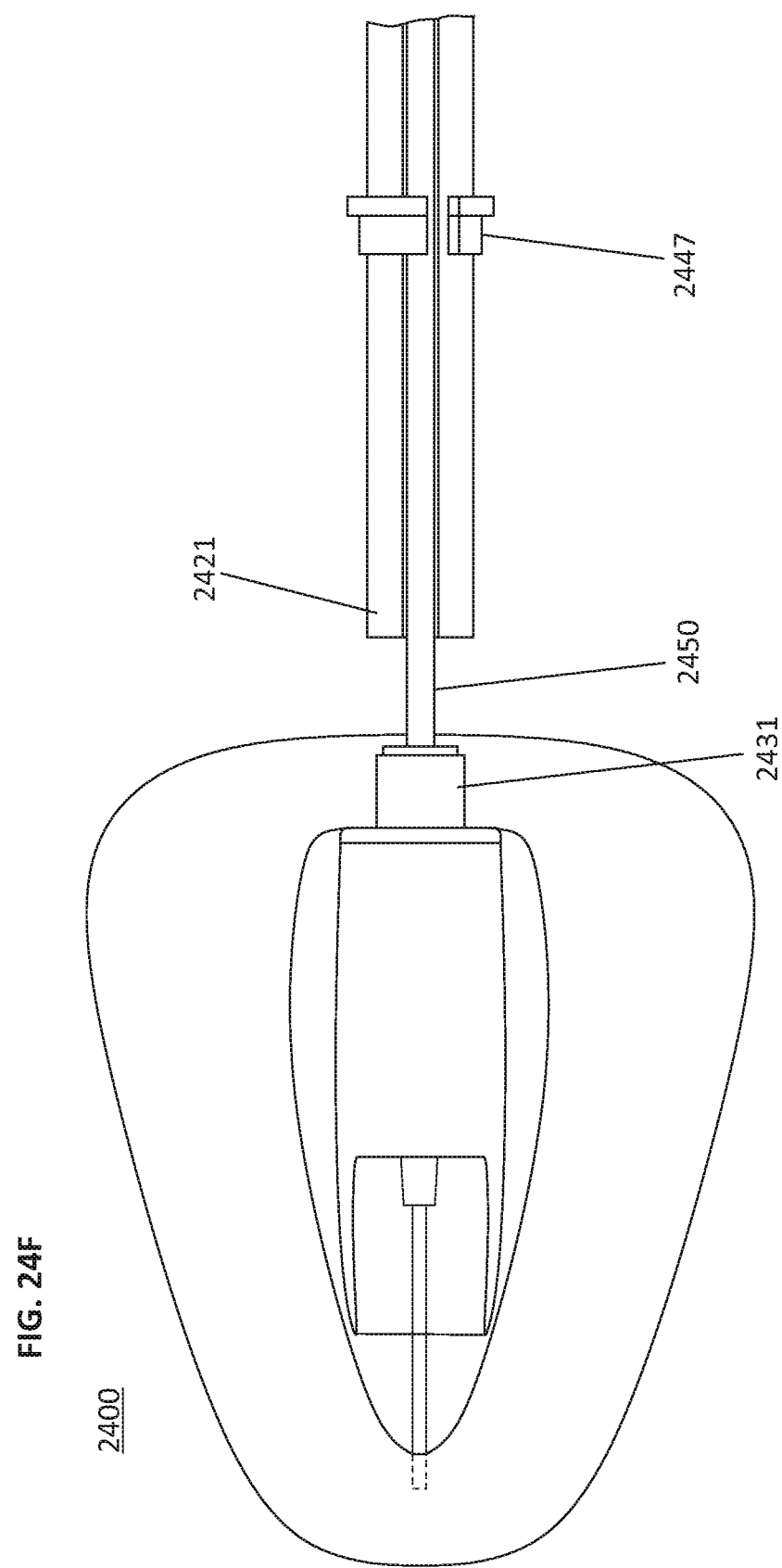
Figure 24G:
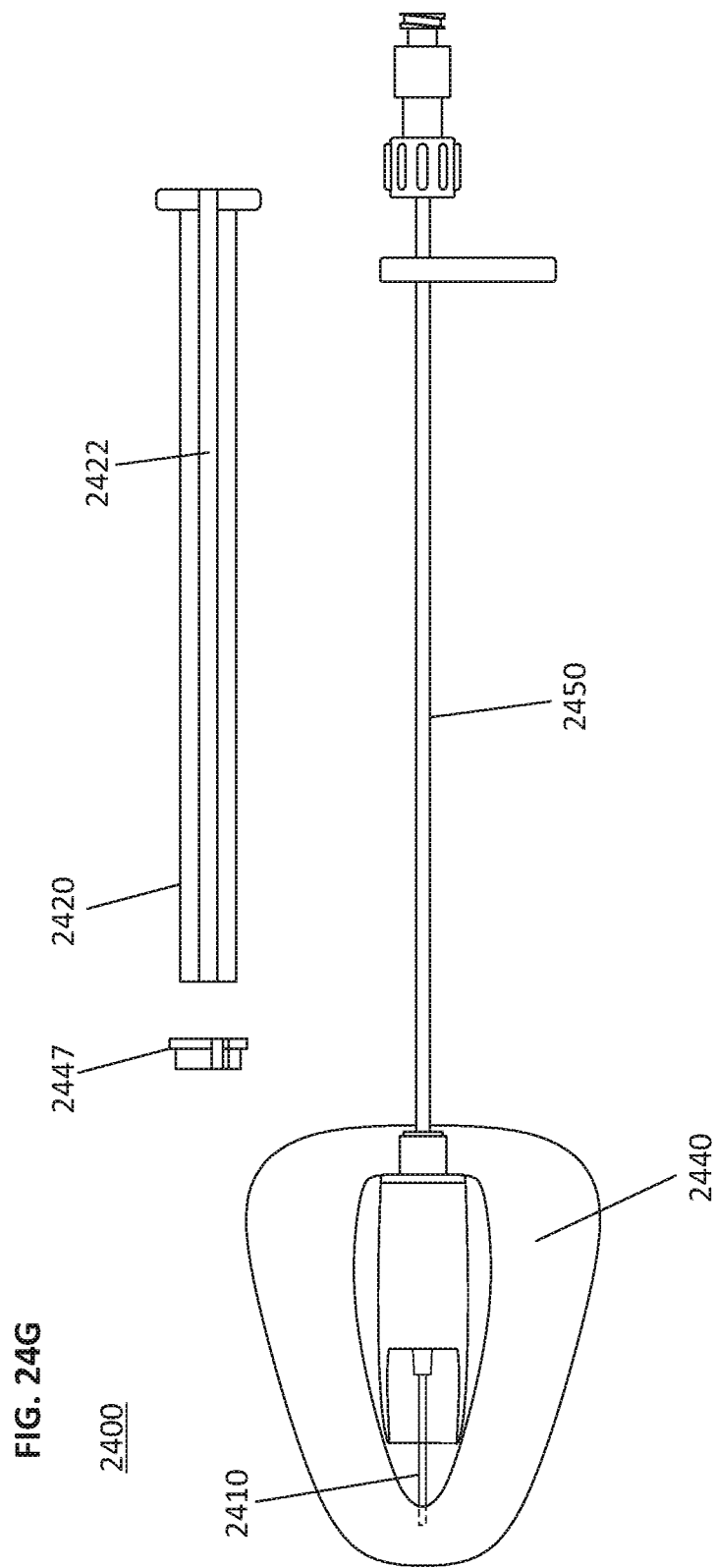

FIGS. 24A-22F show different views of an integrated catheter extension and dressing assembly 2400. In FIG. 24A, the catheter extension system 2400 has a connector 2430 for connection to a catheter or IV needle 2410 at catheter or needle hub 2411. The connector has a mounting point 2431 (e.g., an annular groove, ring, stop flange, or combination thereof). The connector is adapted to mate or couple to a hub 2411 or any conventional IV needle, catheter or catheter assembly at a distal end. The connector is also adapted to mate or couple a mounting handle (i.e., a mounting handle connector) 2420 at a proximal end. The mating to the catheter hub can be performed by any known means, such as any Luer-Lock™ connector, as illustrated in FIG. 24A, a Clave® connector and others. The mating of the connector to the mounting handle can also be performed by known means, such as male and female Luer-Lock™ connectors, snap-fit, bayonet construction, screw thread, twist lock, etc. The connector provides sterility and fluid communication between catheter/needle 4210 and tubing 2450.

The integrated catheter extension system 2400 also has a detachable mounting handle 2420. As illustrated in FIG. 24A, the mounting handle is preassembled and connected to connector 2430. The mounting handle 2420 is generally cylindrical and sized such that a medical dressing 2440 can be disposed thereon (e.g., slidably around the handle). Preferably, the maximum outer diameter of the mounting handle 2420 is less than or equal to the diameter of the specified cap mounting point 2431. This can allow the dressing 2440 to be slid over the mounting handle 2420 so that it can be mounted at the specified connector mounting point 2431. The mounting handle has a distal end 2421, which is adapted to be connected to the connector 2430. The mounting handle also has a proximal end 2423.

As also illustrated in FIG. 24A, proximal end 2423 of the mounting handle 2420 can have a top collar or circumferential flange to allow a user to grip the catheter extension and dressing assembly. A channel or groove 2422 runs along a longitudinal length of the mounting handle 2420. Channel or groove 2422 allows for extension tubing 2450 to be disposed substantially within the mounting handle 2420. The groove 2424 extended to the proximal end 2423 of the mounting handle 1240. The rotatable collar 2447 is also disposed around the mounting handle 2420 behind the dressing 2440 or about the proximal end 2423. In certain embodiments, the collar can slide under the distal lip of the silicone dressing, so that it decreases friction between the silicone dressing and the mountain hand and thereby makes sliding easier.

The extension tubing 2450 exits the mounting handle at proximal end 2420. The groove is sized so that tubing 2450 fits substantially or entirely within the groove. The mounting handle 2420 can have a hollow core, sized to receive and house extension tubing 2450. The mounting handle 2420 completely surrounds the extension tubing 2450. The extension tubing 1050 can optionally have a slide clamp 2452. Also shown in FIG. 24A, is a needle-free connector 2451 attached at a proximal end of the extension tubing. Other connectors, valves, injection ports, tubing and the like can be mated with tubing 2450.

The mounting handle can also include an integrated circumferentially sealing securement dressing 2440. Mounting handle 2420 is sized and configured so that the dressing 2440 slides along the length of the mounting handle 2420. After sliding the dressing 2440 along the mounting handle, the dressing can be secured and fitted to the connector 2430 by mating to the annular fitting, 2431, e.g., a groove, ring and/or stop flange, on the connector. Other snap-fit and/or friction fit configurations that prevent both longitudinal and/or circumferential movement of the IV needle or catheter can also be deployed. This mating prevents the needle/catheter 2410 from inadvertently being pulled out of the insertion site. The dressing also provides a sterile seal at and around the injection site. The needle/catheter 2410 is schematically illustrated in FIG. 24A (e.g., in a patient), but not connected to the catheter extension and integrated dressing assembly 2400.

The catheter system 2400 in FIG. 24A can be connected to needle/catheter 2410 illustrated in FIG. 24B-24G using a Luer-type connector 2430. It will be readily apparent that other appropriate connectors and fittings can be used to connect the catheter extension system 2400 to catheter 2410, depending upon the configuration of the needle or catheter 2410.

Once connector 2430 is connected and secured to needle/catheter 2410, dressing 2440 slides down and over the mounting handle 2420, as illustrated in FIG. 24C. The dressing 2440 attaches to and mates with the mounting point 2431 (e.g., annular groove, ring and/or stop flange) of connector 2430, shown in FIG. 24D. In some embodiments, a peelable backing is removed from dressing). After removable of the backing, an adhesive is exposed for securing the dressing 2440 to a patient's skin at a needle/catheter insertion site.

The dressing can further include a bladder, sponge or other reservoir (similar to that shown in FIG. 22E), to deliver an antimicrobial agent to the skin at the insertion site. For example, a bladder can be filled with an antimicrobial fluid, such as chlorhexidine (CHID) or isopropyl alcohol and a simple squeeze at the time of placement (or during adhesion of the dressing to the skin) can suffice to disinfect the site of any surface pathogens.

In some embodiments, the catheter extension and dressing assembly 2400 includes a single-use or re-fillable bladder. The re-fillable bladder can be filled with chlorhexidine or other sterilizing solution. The chlorhexidine is released from the bladder by squeezing the dressing 2440.

FIGS. 24D and 24E are detailed views of collar element 2447 for use in the catheter extension and integrated dressing assembly of FIGS. 24A-24G. FIG. 24E is another detailed view of the collar element of FIG. 24D, rotated such that the collar groove is aligned with the groove of the mounting handle to permit extraction of the extension tubing 2450 from mounting handle 2420. Finally, the mounting handle 2420 is removed from the assembly 2400 by un-mating the distal end 2421 of the mounting handle 2420 from the connector 2430, illustrated in FIG. 24F. In some embodiments, a one half or less rotation of the mounting handle with respect to connector disconnects these elements. Collar element 2447 is turned such that its opening is aligned with the groove of mounting handle 2420 and extension tubing 2450 is pulled out from groove 2422 and is separated from the mounting handle 2420.

FIGS. 25A-25E illustrates yet another embodiment of an interconnector according to the invention wherein the proximal (away from the patient) end of the interconnector has one or more depressible mounting ridge(s) that are forced downward as the dressing is slid over them, but that then pop back to their original upright position once the dressing is slid past. This mechanism serves to allow easy low friction passage of the dressing, and then also locks the dressing in place once the dressing has slid past into final mating position on the downstream (onward the patient) portion of the interconnector. Furthermore, should the dressing require removal, the depressible mounting ridges can be re-depressed and the dressing removed (in other words while the ridges serve to lock the dressing into position, they also provide a mechanism for easy dressing removal should this be required.

Figure 25A:
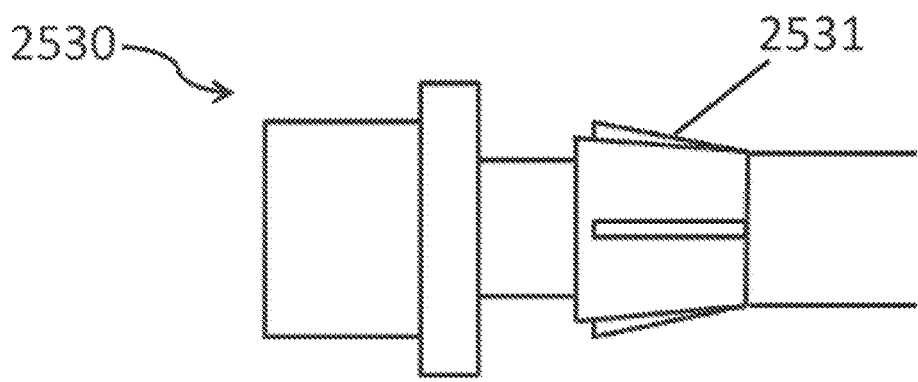
FIGS. 25A-E are illustrations of yet another embodiment of an catheter extension and dressing assembly according to the invention wherein the proximal (away from the patient) end of the interconnector has one or more depressible mounting ridge(s) that are forced downward as the dressing is slid over them.
Figure 25B:
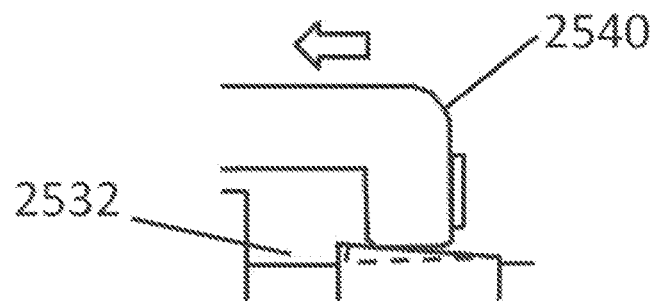
Figure 25C:
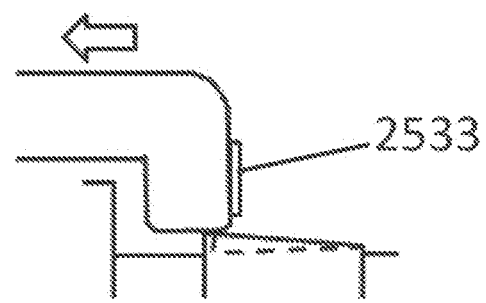
Figure 25D:
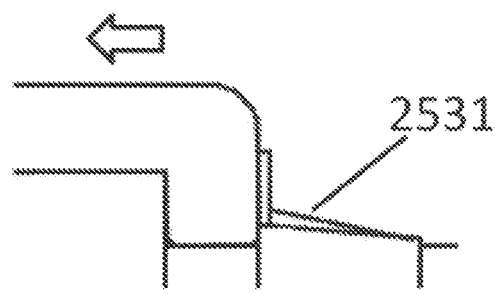
Figure 25E:
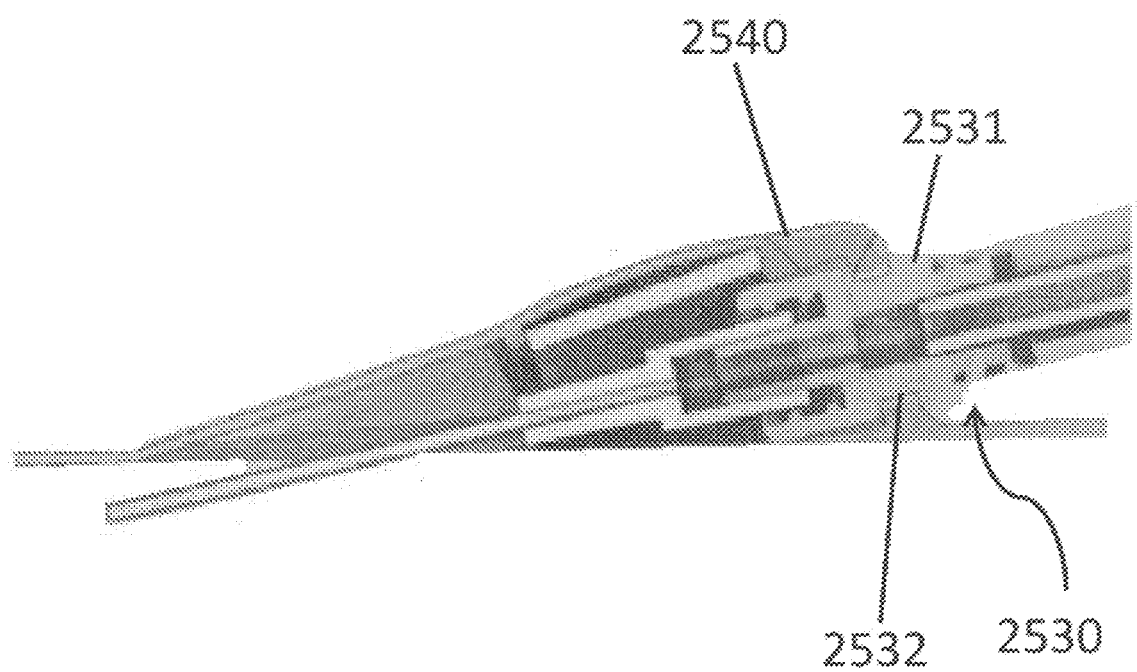

FIG. 25A illustrates an interconnector 2530 according to the invention having a set of peripheral, depressible mount ridges 2531. Although shown with four depressible ridges, it should be clear that fewer or more ridges can be employed. FIG. 25B is a schematic illustration of an initial step in mounting dressing 2540 (shown in part) to interconnector 2530 (also shown in part). The dressing has been slid down over the mounting handle (not shown) and positioned to surround a needle/catheter insertion site. In FIG. 25C the proximal end of the dressing 2540 begins to engage (and depress) the depressible ridges 2531 and begins to slide over them. In FIG. 25D the distal end of dressing has passed over the ridges and is lodged in groove 2532 of the interconnector 2530 so that it can form a sterile seal around the interconnector. A rigid backplate 2533 can be disposed at the proximal end of the interconnector 2530 to mate with the vertical segment of the depressible ridges to ensure a firm connection and prevent dislodgment. Should the dressing 2530 require removal, the depressible mounting ridges 2531 can be re-depressed and the dressing removed.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A catheter system comprising:
   a mounting handle having a proximal end, a distal end, and a groove that runs substantially along a length of said mounting handle;
   a connector coupled to the distal end of the mounting handle and adapted to connect to a catheter at a catheter insertion site, wherein the connector comprises a mating feature;
   a tubing disposed in said groove, and configured to be in fluid communication with the connector; and
   a dressing configured to slide distally along the length of said mounting handle, the dressing being further configured to mate with the mating feature to form a connection,
   wherein the dressing forms a circumferential sterile seal around the catheter insertion site to prevent pathogens from contaminating the catheter insertion site.

2. The catheter system of claim 1, wherein the connection formed between the mating feature of the connector and the dressing is adapted to prevent longitudinal and circumferential movement of the catheter.

3. The catheter system of claim 1, wherein the mating feature is at least one of an annular groove, an annular ring, a stop flange, a depressible ridge or a combination thereof.

4. The catheter system of claim 1, wherein the dressing comprises a distal adhesive plate configured for attachment to a skin region surrounding the catheter insertion site.

5. The catheter system of claim 1, wherein the tubing comprises a needle-free connector at the distal end.

6. The catheter system of claim 5, further comprising a slide clamp disposed on the tubing.

7. The catheter system of claim 1, wherein the groove is created by a peel-away strip, a break-away tab, or a combination thereof.

8. The catheter system of claim 1, wherein the dressing comprises a bladder comprising an antimicrobial agent configured to be delivered to skin at the catheter insertion site.

9. The catheter system of claim 8, wherein the antimicrobial agent comprises chlorhexidine.

10. A method of forming a circumferential sterile seal around a catheter insertion site, comprising:
    obtaining the catheter system of claim 1;
    connecting the connector to a catheter hub of the catheter;
    sliding the dressing along the length of the mounting handle; and
    mating the dressing with the mating feature of the connector, wherein the mating feature comprises at least one of an annular groove, an annular ring, a depressible ridge, a stop flange, or a combination thereof.

11. The method of claim 10, further comprising removing the mounting handle by detaching the mounting handle from the connector.

12. The method of claim 10, further comprising flushing the catheter system with saline prior to connecting the connector with the catheter hub, thereby removing air from the tubing and the connector.

13. The method of claim 10, wherein at least the connector and the tubing of the catheter system is flushed with saline prior to connecting the connector with the catheter hub of the catheter.

* * * * *